US009567307B2

(12) United States Patent
Garg et al.

(10) Patent No.: US 9,567,307 B2
(45) Date of Patent: Feb. 14, 2017

(54) AMINATION OF ARYL ALCOHOL DERIVATIVES

(75) Inventors: Neil K. Garg, Los Angeles, CA (US); Stephen D. Ramgren, Los Angeles, CA (US); Amanda L. Silberstein, Los Angeles, CA (US); Kyle W. Quasdorf, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 393 days.

(21) Appl. No.: 13/978,384

(22) PCT Filed: Jan. 6, 2012

(86) PCT No.: PCT/US2012/020527

§ 371 (c)(1),
(2), (4) Date: Jul. 3, 2013

(87) PCT Pub. No.: WO2012/094622

PCT Pub. Date: Jul. 12, 2012

(65) Prior Publication Data

US 2013/0289270 A1 Oct. 31, 2013

Related U.S. Application Data

(60) Provisional application No. 61/430,749, filed on Jan. 7, 2011.

(51) Int. Cl.

| | |
|---|---|
| ***C07D 263/38*** | (2006.01) |
| ***C07D 295/033*** | (2006.01) |
| ***C07D 295/073*** | (2006.01) |
| ***C07D 295/096*** | (2006.01) |
| ***C07D 209/08*** | (2006.01) |
| ***C07D 211/06*** | (2006.01) |
| ***C07F 7/10*** | (2006.01) |
| ***C07B 37/04*** | (2006.01) |
| ***C07C 209/66*** | (2006.01) |
| ***C07C 269/06*** | (2006.01) |
| ***C07C 303/34*** | (2006.01) |
| ***C07D 209/88*** | (2006.01) |
| ***C07D 213/74*** | (2006.01) |
| ***C07D 263/20*** | (2006.01) |

(52) U.S. Cl.
CPC ............ *C07D 263/38* (2013.01); *C07B 37/04* (2013.01); *C07C 209/66* (2013.01); *C07C 269/06* (2013.01); *C07C 303/34* (2013.01); *C07D 209/08* (2013.01); *C07D 209/88* (2013.01); *C07D 211/06* (2013.01); *C07D 213/74* (2013.01); *C07D 263/20* (2013.01); *C07D 295/033* (2013.01); *C07D 295/073* (2013.01); *C07D 295/096* (2013.01); *C07F 7/10* (2013.01)

(58) Field of Classification Search
CPC ... C07D 263/20; C07D 413/10; C07D 413/12; C07D 295/135; C07D 417/10
USPC .................................. 544/137, 69; 546/192
See application file for complete search history.

(56) References Cited

U.S. PATENT DOCUMENTS

| | | | | |
|---|---|---|---|---|
| 5,837,870 | A * | 11/1998 | Pearlman et al. ............ | 544/137 |
| 2006/0252932 | A1 | 11/2006 | Nidam et al. | |
| 2007/0032472 | A1* | 2/2007 | Mohan Rao et al. ... | 514/211.15 |

OTHER PUBLICATIONS

PCT International Search Report and Written Opinion dated Aug. 14, 2012, International Application No. PCT/US2012/020527.

* cited by examiner

*Primary Examiner* — Alicia L Otton
*Assistant Examiner* — Sagar Patel
(74) *Attorney, Agent, or Firm* — Gates & Cooper LLP

(57) ABSTRACT

Embodiments of the invention provide methods and materials for chemical cross-coupling reactions that utilize aryl alcohol derivatives as cross-coupling partners. Embodiments of the invention include methods for the amination of aryl sulfamates and carbamates, which are attractive cross-coupling partners, particularly for use in multistep synthesis. Illustrative embodiments include versatile means to use simple derivatives of phenol as precursors to polysubstituted aryl amines, as exemplified by a concise synthesis of the antibacterial drug linezolid.

20 Claims, 12 Drawing Sheets

1

2

3 linezolid (4)

linezolid 14 15 16 17 18 19

18

20

21

| Entry | ArOSO2NMe2 | Product | Yield[b] |
|---|---|---|---|
| 1 |  |  | 95% |
| 2 |  |  | 76% |
| 3 |  |  | 77% |
| 4 |  |  | 91% |
| 5[c] |  |  | 80% |
| 6[d] |  |  | 80% |
| 7[e] |  |  | 50% |
| 8[f] |  |  | 64% |
| 9[f] |  |  | 74% |
| 10 |  |  | 96% |
| 11 |  |  | 86% |
| 12[d] |  |  | 72% |
| 13 |  |  | 86% |

TABLE 1. CROSS-COUPLING OF ARYL SULFAMATES WITH MORPHOLINE.

| Entry | Amine | Product | Yield[b] |
|---|---|---|---|
| 1[c] |  |  | 88% |
| 2 |  |  | 93% |
| 3 |  |  | 84% |
| 4[d] |  |  | 77% |
| 5[d] |  |  | 64% |
| 6[e] |  |  | 91% |
| 7[c] |  |  | 90% |
| 8[c] |  |  | 92% |

*TABLE 2.* CROSS-COUPLING OF ARYL SULFAMATES WITH VARIOUS AMINES.[A]

| entry | Ar–OCONEt$_2$ | product | yield[b] |
|---|---|---|---|
| 1 |  |  | 91% |
| 2 |  |  | 92% |
| 3 |  |  | 90% |
| 4[c] |  |  | 74% |
| 5 |  |  | 90% |
| 6[d] |  |  | 77% |
| 7 |  |  | 80% |

TABLE 3: AMINATION OF ARYL CARBAMATES WITH MORPHOLINE.

| entry | Ar–OCONEt$_2$ | product | yield[b] |
| --- | --- | --- | --- |
| 1[c] |  |  | 65% |
| 2[d] |  |  | 53% |
| 3[e] |  |  | 61% |
| 4[d] |  |  | 55% |
| 5[f] |  |  | 84% |
| 6[g] |  |  | 55% |
| 7 |  |  | 78% |

TABLE 4: AMINATION OF *O*-SUBSTITUTED AND HETEROCYCLIC CARBAMATES.[A]

| entry | amine | product | yield[b] |
|---|---|---|---|
| 1[c] |  |  | 96% |
| 2 |  |  | 91% |
| 3 |  |  | 86% |
| 4[d] |  |  | 84% |
| 5[d] |  |  | 70% |
| 6[e] |  |  | 92% |
| 7[c] |  |  | 94% |
| 8[c] |  |  | 93% |

Table 5 Amination of aryl carbamates with various amines

AMINATION OF ARYL ALCOHOL DERIVATIVES

CROSS REFERENCE TO RELATED APPLICATIONS

This application claims the benefit of U.S. provisional patent application No. 61/430,749, filed Jan. 7, 2011, the entire contents of which are incorporated herein by reference.

STATEMENT OF GOVERNMENT SUPPORT

This invention was made with Government support under Grant Nos. GM008496 & GM079922, awarded by the National Institutes of Health. The Government has certain rights in this invention.

BACKGROUND OF THE INVENTION

1. Field of the Invention

The present invention relates to methods and materials for the synthesis of organic compounds.

2. Description of Related Art

Methodologies involving the synthesis of organic molecules play an important role in many technical fields. Materials science, agriculture, biology, and medicine, rely on organic compounds produced by synthetic methods for their ongoing successes and future progress. Consequently, in the past century artisans have devoted significant efforts to the development of new methodologies for the synthesis of various organic compounds. The large number of synthetic methodologies known in the art as a result of these endeavors allows artisans to construct molecules of great complexity. As complex organic molecules become more and more important in a number of scientific disciplines, the ability to prepare key synthetic entities in both a practical and economical fashion becomes increasingly more valuable (see, e.g. Wender et al., *Acc. Chem. Res.* 2008, 41, 40-49).

Of the many synthetic methods used to generate organic compounds, transition metal-catalyzed cross-coupling reactions are known as one of the most effective means of constructing carbon-carbon (C—C) and carbon-heteroatom (C—X such as C—N) bonds (see, e.g. Negishi et al., *Acc. Chem. Res.* 1982, 15, 340-348*; Metal-Catalyzed Cross-Coupling Reactions*; Diedrich, F., Meijere, A., Eds.; Wiley-VCH: Weinheim, 2004; Vol. 2.; Hassan et al., *Chem. Rev.* 2002, 102, 1359-1469*; Topics in Current Chemistry*; Miyaura, N., Ed.; Vol. 219; Springer-Verlag: New York, 2002; Corbet et al., *Rev.* 2006, 106, 2651-2710; Negishi, *Bull. Chem. Soc. Jpn.* 2007, 80, 233-257). Carbon-nitrogen bonds are ubiquitous in medicinal agents and natural products. Transition metal-catalyzed amination reactions, pioneered by Buchwald and Hartwig, are amongst the most powerful methods available for accessing these coveted motifs. Copper- and palladium-mediated aminations of aryl halides and triflates are now well-established and examples of mesylate and tosylate aminations have been reported. Most recent efforts have focused on the amination of classically "inert" phenolic derivatives, i.e., aryl methyl ethers and aryl pivalate esters which could potentially be used in multistep synthesis.

Despite advances in this technology, general methodologies that provide efficient and cost-effective cross-coupling of phenol derivatives have yet to be realized. With the aim of assembling polysubstituted aryl amines, motifs commonly encountered in drug scaffolds, naturally-occurring small molecules, pesticides, ligands for catalysis, and materials chemistry, we worked to discover versatile class of phenol-derived substrates that could undergo transition metal-catalyzed amination.

SUMMARY OF THE INVENTION

As discussed in detail below, we have discovered the first amination reactions of aryl O-sulfamates, which are attractive cross-coupling partners, particularly for use in multistep synthesis. The amination is broad in scope with respect to both the sulfamate and amine coupling partners. The methodology presented herein provides an effective means for accessing polysubstituted aryl amines, as demonstrated by a concise synthesis of the antibacterial drug linezolid. In addition, we have further found that aryl carbamates are also excellent substrates for the nickel-catalyzed amination reaction. The scope of this methodology is broad with respect to both coupling partners, and includes the coupling of electron-rich, heterocyclic, and sterically congested carbamates. For example, we demonstrate that aryl carbamates are outstanding precursors for the synthesis of polysubstituted aryl amines using sequential carbamate functionalization/site-selective coupling processes.

The invention disclosed herein relates to chemical reactions for the synthesis of organic compounds, in particular those that utilize aryl alcohol derivatives as cross-coupling partners. Embodiments of the invention provide efficient and cost-effective cross-coupling reactions that can be used to synthesize a wide variety of cross-coupled compounds including, for example, linezolid. A general embodiment of the invention comprises a method for making a cross-coupled compound by combining together: an amine; an aryl alcohol derivative, wherein the aryl alcohol derivative comprises an aryl carbamate compound or an aryl sulfamate compound, and a transition metal catalyst, wherein the transition metallic catalyst comprises nickel or palladium. In some embodiments, the aryl alcohol derivative comprises an aryl carbamate compound as discussed herein. In other embodiments, the aryl alcohol derivative comprises an aryl sulfamate compound as discussed herein. In such embodiments of the invention, the amine, the aryl alcohol derivative and the transition metal catalyst are combined so as to allow a cross-coupling reaction between the amine, the aryl alcohol derivative and the transition metal catalyst that results in the formation of the cross-coupled compound, typically in a yield of at least 25%. In certain embodiments of the invention, the cross-coupling reaction results in the formation of the cross-coupled compound in a yield of at least 50%.

A related embodiment of the invention is a method for performing a cross-coupling reaction comprising combining together: an amine; an aryl alcohol derivative, wherein the aryl alcohol derivative comprises an aryl carbamate compound or an aryl sulfamate compound; and a transition metal catalyst, wherein the transition metallic catalyst comprises nickel. In other embodiments, the transition metallic catalyst comprises palladium. In such embodiments of the invention, the amine, the aryl alcohol derivative and the transition metal catalyst are combined so as to allow: oxidative addition of the transition metal catalyst and generation of a first organo-transition metal species; reaction between the first organo-transition metal species and the amine and generation of a second organo-transition metal species; and reductive elimination of the second organo-transition metal species, regeneration of the transition metal catalyst and generation of a cross-coupled compound, typically in a yield of at least 25%. In certain embodiments of the invention, the cross-coupling reaction results in the formation of the cross-coupled compound in a yield of at least 50%.

Yet another embodiment of the invention is a cross-coupled compound made by a process comprising combining together: an amine; an aryl alcohol derivative, wherein the aryl alcohol derivative comprises an aryl carbamate compound or, an aryl sulfamate compound; and a transition metal catalyst, wherein the transition metallic catalyst comprises nickel or palladium. In this embodiment, the amine, the aryl alcohol derivative and the transition metal catalyst are combined so as to allow chemical reaction between the amine, the aryl alcohol derivative and the transition metal catalyst, wherein the reaction results in the formation of the cross-coupled compound, typically in a yield of at least 25%. In certain embodiments of the invention, the cross-coupling reaction results in the formation of the cross-coupled compound in a yield of at least 50%.

Embodiments of the invention can employ a variety of methods and materials in order to, for example, control aspects of the cross-coupling reactions. In typical embodiments of the invention, the amine comprises a secondary amine or an aromatic amine (e.g. aniline). In some embodiments of the invention, aryl alcohol derivative comprises a heteroatom. In typical embodiments of the invention, the transition metallic catalyst comprises nickel. In certain embodiments, the transition metal catalyst comprises an air stable Ni(II) precatalyst complex prior to its combination with the amine and the aryl alcohol derivative. In embodiments of the invention, the transition metal catalyst can be regenerated simultaneously with formation of the cross-coupled compound. In certain embodiments of the invention, the cross-coupled compound is formed from a one-pot synthesis and/or the cross-coupling reaction is not performed in a glovebox.

Certain embodiments of the methods for making cross-coupled compounds include further steps to modify and/or purify these compounds. For example, in certain embodiments of the invention, the cross-coupled compound generated by an embodiment of the invention is an intermediate in the synthesis of a target compound (e.g. linezolid). In such embodiments, the further steps can include, for example, performing a base mediated hydrolysis on the cross-coupled compound. Alternatively, the further steps can include, for example, performing an acid or base mediated hydrolysis on the cross-coupled compound. Embodiments of the invention can also include at least one purification step, for example a purification step comprising the chromatographic separation, filtration, extraction, distillation or precipitation of one or more compounds generated by the cross-coupling reaction.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIG. 7A shows Table 1, cross-coupling of aryl sulfamates with morpholine. In Table 1, [a] Conditions unless otherwise stated: $Ni(cod)_2$ (5 mol %), 5 (10 mol %), sulfamate substrate (1 equiv), morpholine (1.2 equiv), NaOtBu (1.4 equiv), dioxane (0.2 M), 80° C. for 3 h. [b] Isolated yields. [c] $Ni(cod)_2$ (10 mol %), 5 (20 mol %), NaOtBu (1.5 equiv). [d] $Ni(cod)_2$ (15 mol %), 5 (30 mol %), morpholine (1.8 equiv), NaOtBu (2.2 equiv). [e] $Ni(cod)_2$ (20 mol %), 5 (40 mol %), NaOtBu (1.7 equiv), 60° C. [f] $Ni(cod)_2$ (15 mol %), 5 (30 mol %), NaOtBu (1.6 equiv). FIG. 7B shows Table 2, cross-coupling of aryl sulfamates with various amines. In Table 2, [a] Conditions unless otherwise stated: $Ni(cod)_2$ (5 mol %), 5 (10 mol %), sulfamate substrate (1 equiv), amine (1.2 equiv), NaOtBu (1.4 equiv), dioxane (0.2 M), 80° C. for 3 h. [b] Isolated yields. [c] $Ni(cod)_2$ (10 mol %), 5 (20 mol %). [d] $Ni(cod)_2$ (15 mol %), 5 (30 mol %), amine (1.8 equiv), NaOtBu (2.2 equiv). [e] $Ni(cod)_2$ (15 mol %), 5 (30 mol %), amine (2.4 equiv), NaOtBu (2.2 equiv). FIG. 7C shows Table 3, amination of aryl carbamates with morpholine. In Table 3, a Conditions unless otherwise stated: $Ni(cod)_2$ (5 mol %), 4 (10 mol %), carbamate substrate (1 equiv), morpholine (1.2 equiv), NaOtBu (1.4 equiv), 3 h. b Isolated yields. c $Ni(cod)_2$ (15 mol %), 4 (30 mol %), morpholine (1.8 equiv), NaOtBu (2.2 equiv). d $Ni(cod)_2$ (10 mol %), 4 (20 mol %). FIG. 7D shows Table 4, amination of o-substituted and heterocyclic carbamates. In Table 4, a Conditions unless otherwise stated: $Ni(cod)_2$ (5 mol %), 4 (10 mol %), carbamate substrate (1 equiv), morpholine (1.2 equiv), NaOtBu (1.4 equiv), 3 h. b Isolated yields. c $Ni(cod)_2$ (15 mol %), 4 (30 mol %), morpholine (1.8 equiv), NaOtBu (2.2 equiv). d $Ni(cod)_2$ (15 mol %), 4 (30 mol %), morpholine (2.4 equiv), NaOtBu (2.2 equiv). e $Ni(cod)_2$ (20 mol %), 4 (40 mol %), morpholine (1.2 equiv), NaOtBu (1.7 equiv), 120° C. f $Ni(cod)_2$ (10 mol %), 4 (20 mol %). g $Ni(cod)_2$ (20 mol %), 4 (40 mol %), morpholine (1.8 equiv), NaOtBu (2.2 equiv). FIG. 7E shows Table 5, amination of aryl carbamates with various amines. In Table 5, a Conditions unless otherwise stated: $Ni(cod)_2$ (5 mol %), 4 (10 mol %), carbamate substrate (1 equiv), amine (1.2 equiv), NaOtBu (1.4 equiv), 3 h. b Isolated yields. c $Ni(cod)_2$ (10 mol %), 4 (20 mol %). d $Ni(cod)_2$ (15 mol %), 4 (30 mol %), amine (1.8 equiv), NaOtBu (2.2 equiv). e $Ni(cod)_2$ (15 mol %), 4 (30 mol %), amine (2.4 equiv), NaOtBu (2.2 equiv).

DETAILED DESCRIPTION OF THE EMBODIMENTS

Figure 1A:
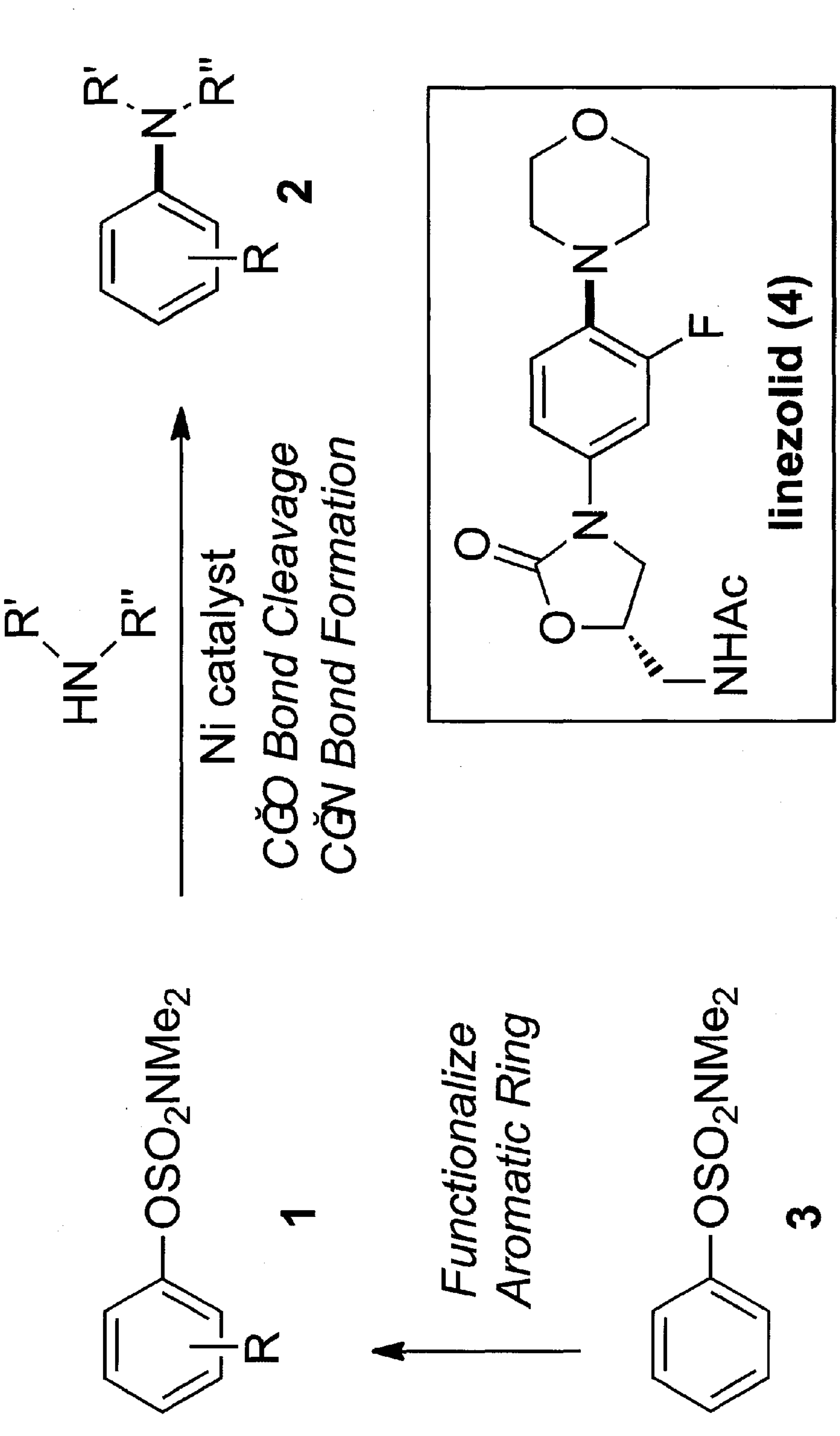
FIGS. 1A and 1B provide schematics showing the amination of aryl sulfamates and linezolid (4).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification. All numbers recited in the specification and associated claims that refer to values that can be numerically characterized can be modified by the term "about".

As is known in the art, "coupling reactions" refers to a range of reactions in organometallic chemistry where two hydrocarbon fragments are coupled with the aid of a metal containing catalyst. Coupling reactions include "cross-coupling reactions" in which two different molecules react to form one new molecule. As used herein, a "cross-coupled compound" is a compound formed by a cross-coupling reaction. As is known in the art, in chemistry a "derivative" (e.g. a "phenol derivative", an "aryl alcohol derivative" etc.) is a compound that is derived from a similar compound or a compound that can be imagined to arise from another compound, if one atom is replaced with another atom or group of atoms. As discussed in detail below, embodiments of this invention relate to methods and materials for making organic compounds through the chemical coupling reactions disclosed herein, for example those that utilize aryl alcohol derivatives as cross-coupling partners.

The invention disclosed herein has a number of embodiments. One illustrative embodiment of the invention comprises a method for making a cross-coupled compound by combining together: an amine; an aryl alcohol derivative, wherein the aryl alcohol derivative comprises an aryl carbamate compound or an aryl sulfamate compound; and a transition metal catalyst, wherein the transition metallic catalyst comprises nickel or palladium. In such embodiments of the invention, the amine, the aryl alcohol derivative and the transition metal catalyst are combined so as to allow a cross-coupling reaction between the amine, the aryl alcohol derivative and the transition metal catalyst that results in the formation of the cross-coupled compound. The resultant cross coupled compound includes a N—C bond where the nitrogen atom in this bond comes from the amine and the carbon atom in this bond comes from the aryl carbamate or aryl sulfamate.

As noted above, the terminology used herein is intended to have the meanings commonly understood by those of skill in the art to which this invention pertains. For example, as is known in the art, "amines" are organic compounds and functional groups that contain a basic nitrogen atom (N) with a lone pair (i.e. a valence electron pair without bonding or sharing with other atom). Primary amines arise when one of three hydrogen atoms in ammonia is replaced by an alkyl. Secondary amines have two alkyl substituents bound to N together with one hydrogen. In tertiary amines, all three hydrogen atoms are replaced by organic substituents. Amines also include derivatives of the various amine types that possess non-alkyl substituents (e.g. aryl substituents, carbonyl substituents, sulfur, nitrogen, oxygen substituents and the like). Aromatic amines have the nitrogen atom connected to an aromatic ring such as anilines. Carbamates are organic compounds derived from carbamic acids, while sulfamates are organic compounds derived from sulfamic acids. A number of illustrative amines, sulfamate moieties and carbamate moieties are disclosed in the Examples below and the associated Figures and Tables.

As used herein, the term "alkyl" refers to a branched or unbranched saturated hydrocarbon group typically although not necessarily containing about 1-24 carbon atoms, unless indicated otherwise. Exemplary alkyl groups include methyl, ethyl, n-propyl, isopropyl, n-butyl, isobutyl, t-butyl, n-amyl, isoamyl, n-hexyl, n-heptyl, n-octyl, n-decyl, hexyloctyl, tetradecyl, hexadecyl, eicosyl, tetracosyl, and the like, as well as cycloalkyl groups such as cyclopropyl, cyclobutyl, cyclopentyl, cyclohexyl, cycloheptyl, cyclooctyl and the like. Generally, although again not necessarily, alkyl groups herein contain about 1-12 carbon atoms. The term "lower alkyl" refers to an alkyl group of 1-6 carbon atoms, e.g. 1-4 carbon atoms. The alkyl group is optionally substituted at one or more positions. Exemplary substituents include but are not limited to hydroxyl, cyano, alkoxy, =O, =S, —$NO_2$, halo, heteroalkyl, amine, thioether, —SH, and aryl. Accordingly, if not otherwise indicated, the terms "alkyl" includes branched, unbranched, unsubstituted, and substituted alkyl groups. The term "cycloalkyl" refers to a cyclic alkyl, as defined above, and is typically a stable 3- to 7 membered monocyclic or 7- to 10-membered polycyclic ring which is saturated or partially unsaturated (e.g., containing one or more double bonds). Similarly, the term "cycloheteroalkyl" is intended to mean a cyclic alkyl group, as defined above, that contains one or more heteroatoms, and is typically a stable 3- to 7 membered monocyclic or 7- to 10-membered polycyclic ring which is saturated or partially unsaturated and contains 1-4 heteroatoms (N, O, S, P or Si). As with alkyl, the terms "cycloalkyl" and "cycloheteroalkyl" are intended to include both unsubstituted and substituted groups. The substitutions can be on a carbon or a heteroatom if the resulting compound is stable. For example, any amino group contained within the heterocycloalkyl group can be a primary, secondary or tertiary amine, as long as the structure is stable. As used herein, the term "alkene" refers to unsaturated hydrocarbons having at least one double bond between two carbon atoms, and the term "alkenyl" refers to a group derived from an alkene.

As used herein, the term "aryl" is intended to mean an aromatic substituent containing a single aromatic ring (e.g., phenyl) or multiple aromatic rings that are fused together (e.g., naphthyl or biphenyl), directly linked, or indirectly linked (such that the different aromatic rings are bound to a common group such as a methylene or ethylene moiety). Typically, the aryl group comprises from 5 14 carbon atoms. Illustrative aryl groups contain one aromatic ring or two fused or linked aromatic rings, e.g., phenyl, naphthyl, biphenyl, diphenylether, diphenylamine, benzophenone, and the like. The aryl moiety may be independently substituted with one or more substituent groups, typically 1 3 substituents, including =O, —OH, —COOH, —$CH_2$—$SO_2$-phenyl, —$C_{1\text{-}6alkyl}$, —O—$C_{1\text{-}6alkyl}$, —C(O)—$C_{1\text{-}4alkyl}$, —$(CH_2)_{0-2}$—C(O)—O—$C_{1-4alkyl}$, cycloalkyl, —$C_{1-6alkoxy}$, halo, nitro, amino, alkylamino, dialkylamino, —C(O)—N$(C_{1-4alkyl})_2$, —NH—C(O)$C_{1-4alkyl}$, —C(O)—$NH_2$, —$SO_2$—$NH_2$, trifluoromethyl, cyano, aryl, benzyl, —O-aryl and —S-aryl. Thus, the term "aryl" includes unsubstituted and substituted aryl groups. The term "heteroaryl" refer to aryl, as defined above, in which at least one carbon atom, typically 1-3 carbon atoms, is replaced with a heteroatom N, O, S, P or Si). The heteroaryl can have the heteroatoms within a single ring, (e.g., such as pyridyl, imidazolyl, thiazolyl, pyrimidine, oxazolyl, and the like), or within two rings (e.g., indolyl, quinolinyl, benzofuranyl, and the like). As with aryl, the term "heteroaryl" is intended to include both unsubstituted and substituted heteroaryl groups. The substitutions can be on a carbon or a heteroatom if the resulting compound is stable. For example, any amino group contained within the heteroaryl group can be a primary, secondary or tertiary amine, as long as the structure is stable.

As shown by the variety of illustrative embodiments of the invention disclosed in Examples 1 and 2 below, the methodologies disclosed herein successfully achieve the cross-coupling of aryl sulfamates and aryl carbamates to produce cross-coupled products in highly efficient yields, thereby overcoming problems observed in this art. Typically, a method for producing a cross-coupled compound as disclosed herein produces a cross-coupled compound in a yield of at least 25%. In certain embodiments of the invention, the cross-coupling reaction results in the formation of the cross-coupled compound in a yield of at least 30%, 40%, 50%, 60%, 70%, 80%, 90% or higher. As is known in the art, in chemistry, "yield", also referred to as chemical yield and reaction yield, is the amount of product obtained in a chemical reaction (see, e.g. Vogel, A. I., Tatchell, A. R., Furnis, B. S., Hannaford, A. J. and P. W. G. Smith. Vogel's Textbook of Practical Organic Chemistry, 5th Edition. Prentice Hall, 1996). The absolute yield can be given as the weight in grams or in moles (molar yield). The fractional yield, relative yield, or percentage yield, which serve to measure the effectiveness of a synthetic procedure, can be calculated by dividing the amount of the obtained product in moles by the theoretical yield in moles. To obtain the percentage yield, one can multiply the fractional yield by 100 (e.g., 0.673=67.3%). In one exemplary method for calculating yields, one can start with x moles (a defined amount) of a carbamate (or a sulfamate, an amine etc.), with the consequential expectation of getting x moles of cross-coupled product following the cross-coupling reaction. Following the cross-coupling reaction, the pure product can be isolated and its weight determined. Using this determined weight, one can then convert to moles of cross-coupled produced, and then use this value to calculate yield. In such reactions, the amounts of the individual reactants can be manipulated to control, for example, stoichiometric parameters in these processes. For example, in such reactions one can use a reactant such as an amine in excess, or alternatively, as a limiting reagent.

Embodiments of the invention can employ a variety of methods and materials in order to, for example, control aspects of the cross-coupling reactions. In certain embodiments of the invention, the amine is a secondary amine, or an aromatic amine such as an aniline, or a derivative of one of the various amine types that possess non-alkyl substituents (e.g. aryl substituents, carbonyl substituents, sulfur, nitrogen, oxygen substituents and the like). In certain embodiments of the invention, the carbamate moiety is of the type found in N,N-dialkylcarbamates and the like. In certain embodiments of the invention, the sulfamate moiety is of the type found in N,N-dialkylsulfamates and the like. For both carbamates and sulfamates, in some embodiments of the invention the compound comprises another type of N,N-substitution such as N,N-diaryl, N-alkyl-N-aryl, N-acyl-N-alkyl, N-acyl-N-aryl, N-acyl-N-acyl, N-sulonyl-aryl, N-sulonyl-alkyl, N-sulfonyl-N-acyl and the like. In some embodiments of the invention, aryl alcohol derivative comprises a heteroatom. As is known in the art, a "heteroatom" is: any atom in a heterocyclic ring (or other structure normally built of carbon atoms) that is not a carbon atom. Typical heteroatoms include nitrogen, oxygen, sulfur, phosphorus, boron, chlorine, bromine, or iodine.

As is known in the art, a "transition metal" is an element whose atom has an incomplete d sub-shell, or which can give rise to cations with an incomplete d sub-shell. In typical embodiments of the invention, the transition metallic catalyst comprises nickel. Optionally, the transition metallic catalyst comprises $Ni(COD)_2$. As is known in the art, metallic catalysts comprise ligands and can be used with other ligands present (e.g., N-heterocyclic carbene ligands are used in the illustrative embodiments of the invention that are disclosed herein). Those of skill in the art will understand that other ligand scaffolds such as phosphines, n-heterocyclic carbenes, amines, and the like can be used in embodiments of the invention. As is known in this art, often the active catalyst in a reaction is not the same as the initial catalyst introduced into the reaction (e.g. in situations where an initial catalyst is exposed to one or more reagents and/or reaction conditions in order to form the active catalyst). In certain embodiments, the transition metal catalyst comprises an air stable Ni(II) precatalyst complex prior to its combination with the amine and the aryl alcohol derivative. In embodiments of the invention, the transition metal catalyst can be regenerated simultaneously with formation of the cross-coupled compound.

Embodiments of the invention utilize a variety of reaction parameters. For example, reactions can be carried out at a range of temperatures (e.g. from 20° C. to 200° C.). Typically however, the reactions disclosed herein are keep at a temperature ranging from 80° C. to 130° C. Similarly, reactions can be carried out in the presence of a variety of organic solvents such as toluene, xylenes, dioxane, dimethoxyethane, benzene, tetrahydrofuran, dimethylformamide, dimethylacetamide, N-methylpyrrolidinone (and combinations of such solvents). In some embodiments of the invention, the cross-coupled compound is formed from a cross-coupling reaction that is performed in a glovebox. In other embodiments of the invention, the cross-coupled compound is formed from a cross-coupling reaction that is not performed in a glovebox. In some embodiments of the invention, the cross-coupled compound is formed from a one-pot synthesis. As is known in the art, a "one-pot synthesis" is a strategy to improve the efficiency of a chemical reaction whereby a reactant is subjected to successive chemical reactions in just one reactor. This is much desired by artisans in this technology because avoiding a lengthy separation process and purification of the intermediate chemical compounds saves time and resources while increasing chemical yield. In some embodiments of the invention where the cross-coupled compound is formed from a one-pot synthesis, the reactants can be premade and added into the reaction vessel. In other embodiments of the invention where the cross-coupled compound is formed from a one-pot synthesis, the reactants can be themselves synthesized in the reaction vessel in which the cross-coupled compound is subsequently formed.

In certain embodiments of the invention, the cross-coupled compound generated by an embodiment of the invention is an intermediate in the synthesis of a target compound such as linezolid. Such embodiments of the methods for making cross-coupled compounds can include additional steps to further modify and/or purify these compounds. In such embodiments, the further steps can include, for example, performing an acid mediated hydrolysis on the cross-coupled compound. Alternatively, the further steps can include, for example, performing a base mediated hydrolysis on the cross-coupled compound. Embodiments of the invention can also include at least one purification step, for example a purification step comprising the chromatographic separation, filtration, extraction, distillation or precipitation of one or more compounds generated by the cross-coupling reaction.

Further aspects and embodiments of the invention are disclosed in the following examples.

EXAMPLES

Methods and materials for practicing embodiments of the invention as discussed below have also been published in journals within this field of technology. These publications include: Ramgren et al., *Angewandte Chemie*, Volume 123, Issue 9, pages 2219-2221, (2011); and Tehetena et al., *Chem. Sci.,* 2011, 2, 1766-1771, the entire contents of which (e.g. including supplementary materials which are available online) are incorporated herein in their entirety.

Example 1

Nickel-Catalyzed Amination of Aryl Sulfamates

Carbon-nitrogen bonds are ubiquitous in medicinal agents and natural products (see, e.g. J. P. Wolfe et al., *Acc. Chem. Res.* 1998, 31, 805-818; J. F. Hartwig, *Angew. Chem. Int. Ed.* 1998, 37, 2046-2067; *Angew. Chem.* 1998, 110, 2154-2177; A. R. Muci et al., In *Topics in Current Chemistry*, Vol. 219 (Ed: N. Miyaura), Springer-Verlag, Berlin, 2001; p. 131; M. Kienle et al., *Eur. J. Org. Chem.* 2007, 4166-4176). Transition metal-catalyzed amination reactions, pioneered by Buchwald and Hartwig, are amongst the most powerful methods available for accessing these coveted motifs (see, e.g. J. P. Wolfe et al., *Acc. Chem. Res.* 1998, 31, 805-818; J. F. Hartwig, *Angew. Chem. Int. Ed.* 1998, 37, 2046-2067; *Angew. Chem.* 1998, 110, 2154-2177; A. R. Muci et al., In *Topics in Current Chemistry, Vol.* 219 (Ed: N. Miyaura), Springer-Verlag, Berlin, 2001; p. 131; d) M. Kienle et al., *Eur. J. Org. Chem.* 2007, 4166-4176). Copper- and palladium-mediated aminations of aryl halides and triflates are now well-established (see, e.g. J. P. Wolfe et al., *Acc. Chem. Res.* 1998, 31, 805-818; J. F. Hartwig, *Angew. Chem. Int. Ed.* 1998, 37, 2046-2067; Angew. Chem. 1998, 110, 2154-2177; A. R. Muci et al., In *Topics in Current Chemistry*, Vol. 219 (Ed: N. Miyaura), Springer-Verlag, Berlin, 2001; p. 131; M. Kienle et al., *Eur. J. Org. Chem.* 2007, 4166-4176) and examples of mesylate (B. P. Fors et al., *J. Am. Chem. Soc.* 2008, 130, 13552-13554; C. M. So et al., *Angew. Chem. Int. Ed.* 2008, 47, 6402-6406; *Angew. Chem.* 2008, 120, 6502-6506) and tosylate, (B. C. Hamann et al., *J. Am. Chem. Soc.* 1998, 120, 7369-7370; A. H. Roy et al., *J. Am. Chem. Soc.* 2003, 125, 8704-8705; T. Ogata et al., *J. Am. Chem. Soc.* 2008, 130, 13848-13849; C.-Y. Gao et al., *J. Org. Chem.* 2008, 73, 1624-1627) aminations have been reported. Most recent efforts have focused on the amination of classically "inert" phenolic derivatives, i.e., aryl methyl ethers (the amination of aryl methyl ethers proceeds most efficiently using 2-methoxynaphthalene and cyclic secondary amines; see: M. Tobisu et al., *Chem. Lett.* 2009, 38, 710-711) and aryl pivalate esters (T. Shimasaki et al., *Angew. Chem. Int. Ed.* 2010, 49, 2929-2932; Angew. Chem. 2010, 122, 2991-2994), which could potentially be used in multistep synthesis. A single example of an aryl carbamate undergoing amination has been described in the literature using N,N-diethylphenylcarbamate (see T. Shimasaki et al., *Angew. Chem.* 2010, 122, 2991-2994). With the aim of assembling polysubstituted aryl amines, motifs commonly encountered in drug scaffolds, naturally-occurring small molecules, pesticides, ligands for catalysis, and materials chemistry, we sought to uncover a versatile class of phenol-derived substrates that could undergo transition metal-catalyzed amination.

Figure 1B:
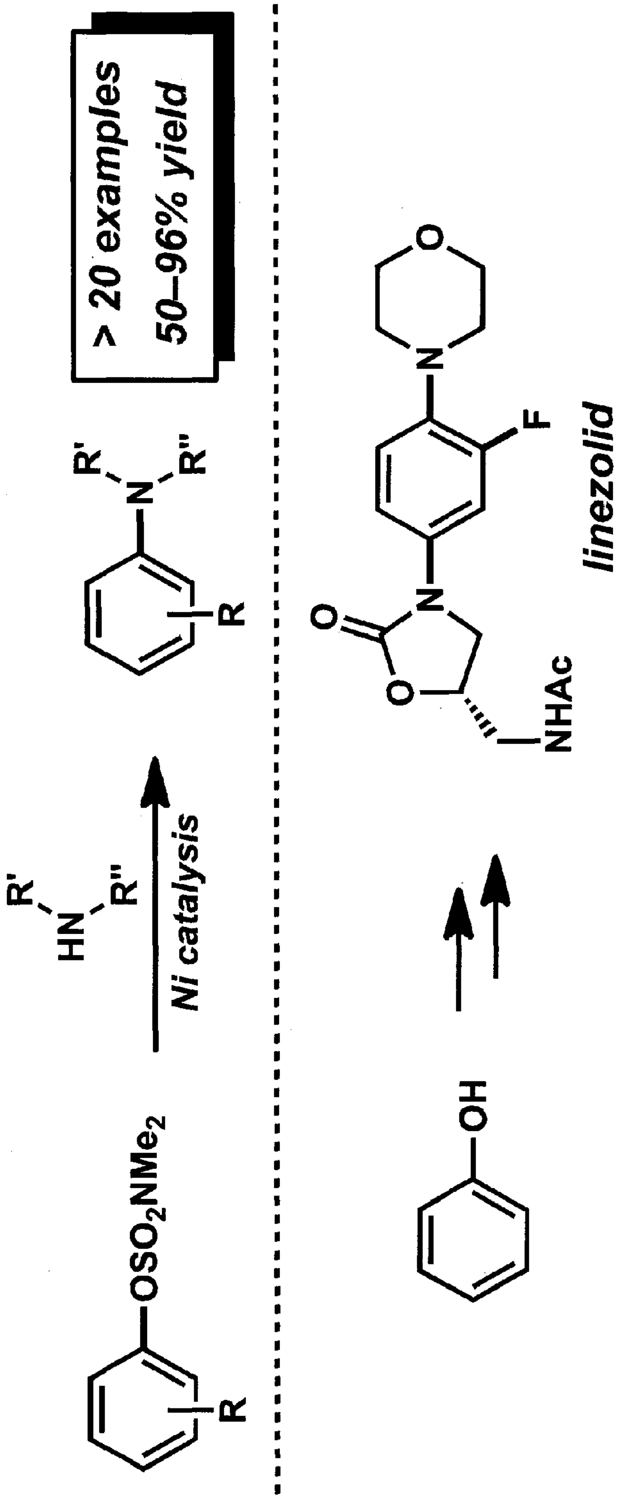

Although relatively unexplored, N,N-dialkyl aryl O-sulfamates (e.g., 1, FIG. 1) are extremely attractive electrophiles for cross-coupling reactions. They are easy to prepare, (aryl N,N-dimethylsulfamates are readily prepared from aryl alcohols and commercially available N,N-dimethylsulfamoyl chloride (approximate cost $0.80 per gram from Aldrich Chemical Co., Inc.) stable to a variety of reaction conditions, and exhibit low reactivity toward Pd(0) (for Kumada couplings, see: T. K. Macklin et al., *Org. Lett.* 2005, 7, 2519-2522; P. M. Wehn et al., *Org. Lett.* 2005, 7, 4685-4688; for the use of aryl sulfamates in directed metallation, electrophilic aromatic substitution, multistep synthesis, and the Suzuki-Miyaura couplings, see: K. W. Quasdorf et al., *J. Am. Chem. Soc.* 2009, 131, 17748-17749). Moreover, the sulfamate moiety can be used to functionalize an arene at both the ortho or para positions, prior to carrying out a cross-coupling event. See, e.g. T. K. Macklin et al., *Org. Lett.* 2005, 7, 2519-2522; for the use of aryl sulfamates in directed metallation, electrophilic aromatic substitution, multistep synthesis, and the Suzuki-Miyaura couplings, see: K. W. Quasdorf et al., *J. Am. Chem. Soc.* 2009, 131, 17748-17749). Other phenol-based amination partners cannot be used effectively for directed metallation/functionalization. Specifically, aryl sulfonates and pivalates are not suitable substrates, whereas aryl methyl ethers are poor metalation substrates. For reviews see: V. Snieckus, *Chem. Rev.* 1990, 90, 879-933; C. G. Hartung et al., In *Modern Arene Chemistry* (Ed.: D. Astruc), Wiley-VCH, New York, 2002, pp. 330-367; T. Macklin et al., In *Handbook of C—H Transformations*, (Ed.: G. Dyker), Wiley-VCH: New York, 2005, pp. 106-119). Despite that aryl O-sulfamates have been employed in carbon-carbon bond forming reactions, their use in carbon-nitrogen bond construction has remained undiscovered (although an initial oxidative addition step would be common to both C—C and C—N bond-forming reactions of aryl sulfamate substrates, the remaining steps of the presumed catalytic cycles are quite different). See, e.g. J. P. Wolfe et al., *Acc. Chem. Res.* 1998, 31, 805-818; and J. F. Hartwig, *Angew. Chem. Int. Ed.* 1998, 37, 2046-2067). Herein, we report the first amination of aryl O-sulfamates (1→2) and the application of this methodology to a concise synthesis of the antibacterial drug linezolid (4) (Linezolid, marketed by Pfizer Inc. under the name Zyvox®, is used to treat a variety of infections. In recent years, worldwide sales of Zyvox® have been approximately 1.1 billion dollars per year.

Figure 7A:
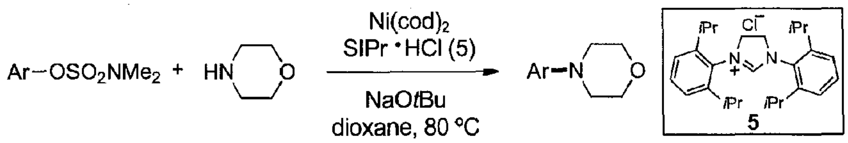
FIGS. 7A-7E provides tables showing various reactants and products relating to embodiments of the invention disclosed herein.
Figure 7A:
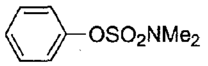
Figure 7A:
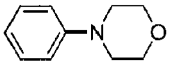
Figure 7A:
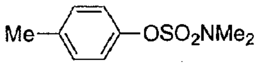
Figure 7A:
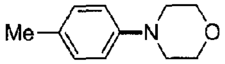
Figure 7A:
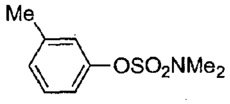
Figure 7A:
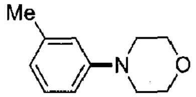
Figure 7A:
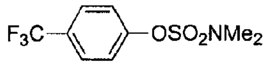
Figure 7A:
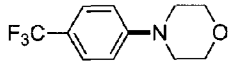
Figure 7A:
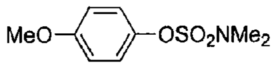
Figure 7A:
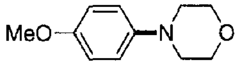
Figure 7A:
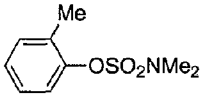
Figure 7A:
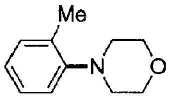
Figure 7A:
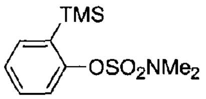
Figure 7A:
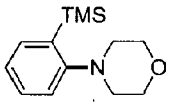
Figure 7A:
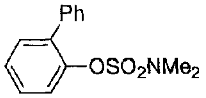
Figure 7A:
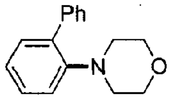
Figure 7A:
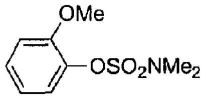
Figure 7A:
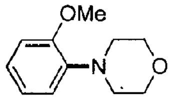
Figure 7A:
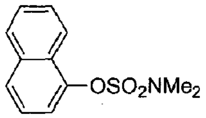
Figure 7A:
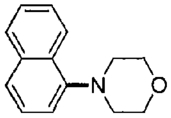
Figure 7A:
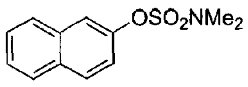
Figure 7A:
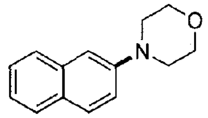
Figure 7A:
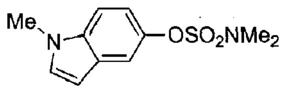
Figure 7A:
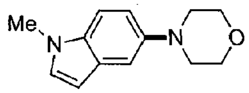
Figure 7A:
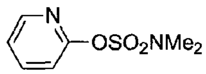
Figure 7A:
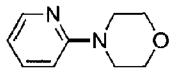

Initial studies were aimed at promoting the amination of dimethylsulfamate derivatives of phenol and 1-naphthol. Although catalytic systems based on nickel and $PCy_3$ have been the cornerstone of several recent nickel-catalyzed cross-couplings involving carbon-oxygen bonds, including the Suzuki-Miyaura coupling of aryl O-sulfamates, this metal/ligand combination was ineffective in our amination studies (although an initial oxidative addition step would be common to both C—C and C—N bond-forming reactions of aryl sulfamate substrates, the remaining steps of the presumed catalytic cycles are quite different). For phenolic ester couplings, see K. W. Quasdorf et al., *J. Am. Chem. Soc.* 2008, 130, 14422-14423; B.-T. Guan et al., *J. Am. Chem. Soc.* 2008, 130, 14468-14470; B.-J. Li et al., *Angew. Chem. Int. Ed.* 2008, 47, 10124-10127; *Angew. Chem.* 2008, 120, 10278-10281; for methyl ether couplings, see: M. Tobisu et al., *Angew. Chem. Int. Ed.* 2008, 47, 4866-4869; Angew. Chem. 2008, 120, 4944-4947; J. W. Dankwardt, *Angew. Chem. Int. Ed.* 2004, 43, 2428-2432; *Angew. Chem.* 2004, 116, 2482-2486; for carbamate couplings, see: A. Antoft-Finch et al., *Am. Chem. Soc.* 2009, 131, 17750-17752; L. Xi et al., *Org. Lett.* 2010, 12, 884-887). For the use of aryl sulfamates in directed metallation, electrophilic aromatic substitution, multistep synthesis, and the Suzuki-Miyaura couplings, see: K. W. Quasdorf et al., *J. Am. Chem. Soc.* 2009, 131, 17748-17749. After conducting an extensive survey of reaction parameters (e.g., nickel catalysts, ligands, solvents, bases, temperature, etc.) it was observed that N-heterocyclic carbene ligands facilitated the desired amination. Under optimal conditions, treatment of sulfamate 3 with morpholine in the presence of catalytic $Ni(cod)_2$, SIPr.HCl (5), and NaOtBu, in dioxane at 80° C. for 3 h afforded the aminated product in 95% yield (FIG. 7A, Table 1, Entry 1). Although other N-heterocyclic carbene ligands could be used to achieve this exact coupling, commercially available SIPr.HCl (5, CAS#258278-25-0) proved most generally useful, particularly for the amination of ortho-substituted substrates.

A variety of sulfamate substrates were examined in the nickel-catalyzed amination process (Table 1). Methyl substituents at the para and meta positions were tolerated (entries 2 and 3), in addition to the electron-withdrawing trifluoromethyl group and the electron-donating methoxy group (entries 4 and 5, respectively). Given the utility of the sulfamate in directed metalation chemistry, we examined the amination of several ortho-substituted substrates bearing a methyl, trimethylsilyl, phenyl, or methoxy substituent. See, e.g. T. K. Macklin et al., *Org. Lett.* 2005, 7, 2519-2522; for the use of aryl sulfamates in directed metallation, electrophilic aromatic substitution, multistep synthesis, and the Suzuki-Miyaura couplings, see: K. W. Quasdorf et al., *J. Am. Chem. Soc.* 2009, 131, 17748-17749. In all cases, amination proceeded smoothly (entries 6-9). Naphthyl-based substrates were found to be excellent amination substrates (entries 10 and 11). Furthermore, heterocycles, such as indole and pyridine, were tolerated in this methodology (entries 12 and 13).

Figure 7B:
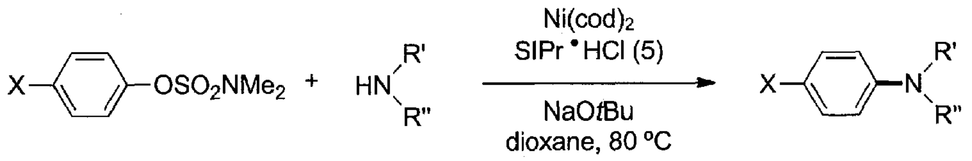
Figure 7B:
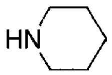
Figure 7B:
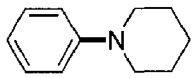
Figure 7B:
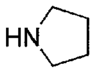
Figure 7B:
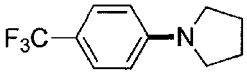
Figure 7B:
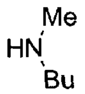
Figure 7B:
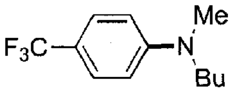
Figure 7B:
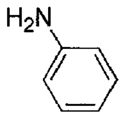
Figure 7B:
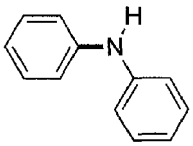
Figure 7B:
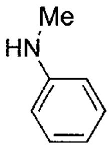
Figure 7B:
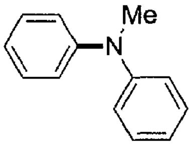
Figure 7B:
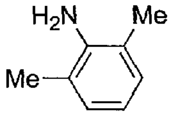
Figure 7B:
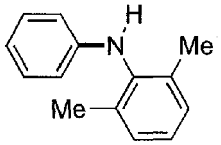
Figure 7B:
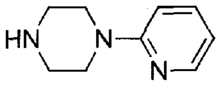
Figure 7B:
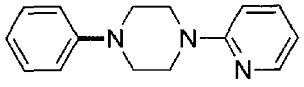
Figure 7B:
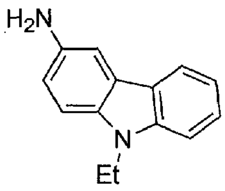
Figure 7B:
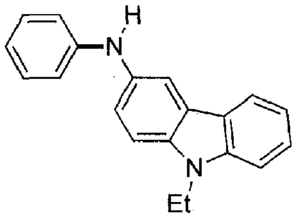

As shown in Table 2 (FIG. 7B), the scope of aryl O-sulfamate amination is also broad with respect to the amine coupling partner. Both cyclic and acyclic secondary amines were found to be suitable substrates (entries 1-3). In addition, anilines could be employed (entries 4-6), including 2,6-dimethylaniline (entry 6). The methodology also allows for the coupling of amines with appended heterocycles, as demonstrated by the coupling of pyridine- and carbazole-containing substrates (entries 7 and 8).

Figure 2:
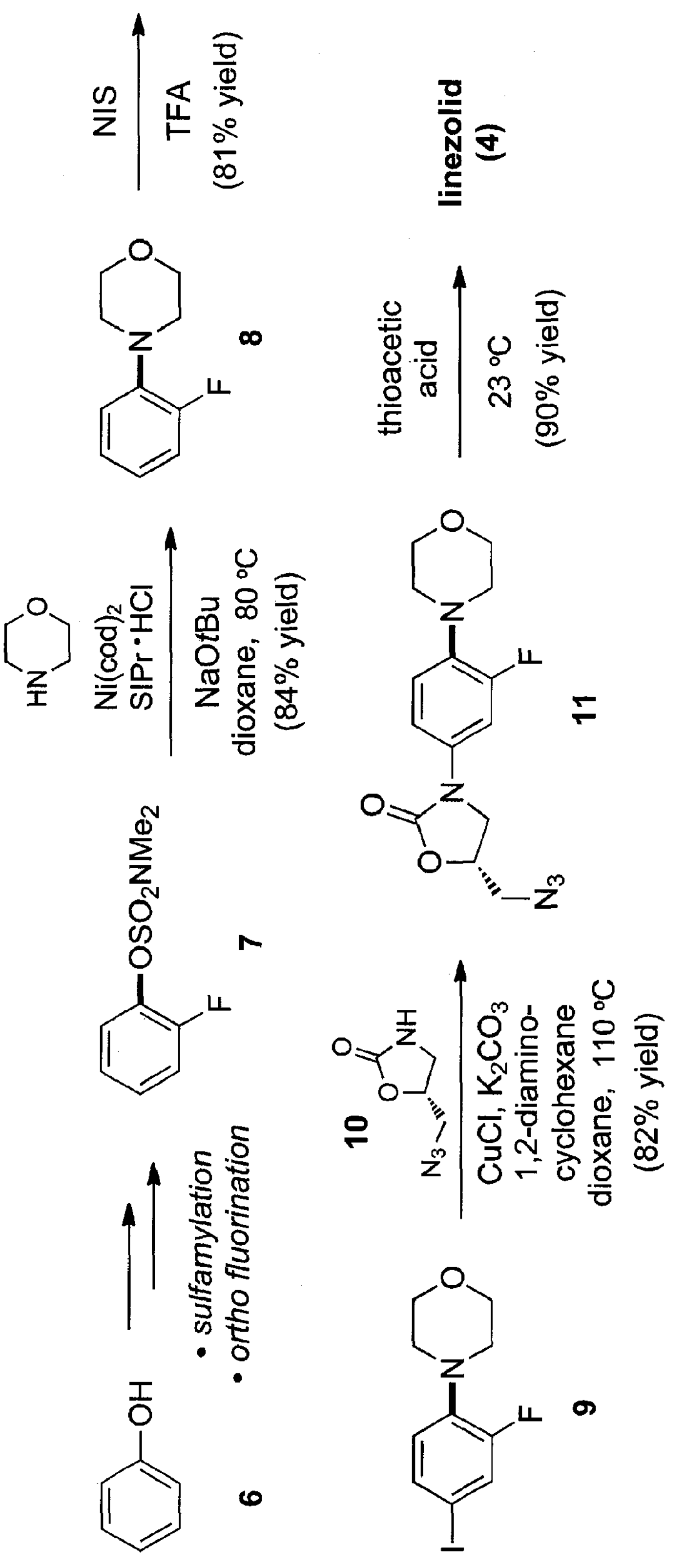
FIG. 2 provides a schematic showing the synthesis of linezolid (4) using Ni-catalyzed amination.

To further probe the scope and utility of the sulfamate amination methodology, a concise synthesis of the antibacterial drug linezolid (4) was performed (FIG. 2). Linezolid, marketed by Pfizer Inc. under the name Zyvox®, is used to treat a variety of infections. In recent years, worldwide sales of Zyvox® have been approximately 1.1 billion dollars per year; (search, for example: "www.pfizer.com/investors/financial_reports/annual_reports/key_medicinesjsp"). Beginning from phenol (6), fluorosulfamate 7 was readily prepared using our previously reported sequence. This conversion proceeds by sulfamylation, followed by ortho-fluorination (two-steps), and showcases the sulfamate's directing ability. Nickel-catalyzed sulfamate amination proceeded smoothly to deliver intermediate 8, without interference from the fluoro substituent (for nickel-catalyzed Kumada and Suzuki-Miyaura couplings of aryl fluorides, see: N. Yoshikai et al., *J. Am. Chem. Soc.* 2005, 127, 17978-17979; J. W. Dankwardt, *J. Organomet. Chem.* 2005, 690, 932-938; T. Schaub et al., *J. Am. Chem. Soc.* 2006, 128, 15964-15965). Subsequent iodination furnished trisubstituted arene 9, which in turn, underwent copper-catalyzed coupling with oxazolidinone 10 to afford arylated oxazolidinone 11 in good yield. In the final step, reductive acetylation of azide 11 furnished linezolid (4). Overall, our synthesis illustrates the merits of sulfamate-directed arene functionalization and coupling methodology in a complex setting.

In summary, we have discovered the first amination reactions of aryl O-sulfamates, which are attractive cross-coupling partners, particularly for use in multistep synthesis. The amination is broad in scope with respect to both the sulfamate and amine coupling partners. The methodology presented herein provides an effective means for accessing polysubstituted aryl amines, as demonstrated by a concise synthesis of the antibacterial drug linezolid.

Illustrative Embodiments

A large number of working examples are provides as follows in order to illustrate the versatility and scope of embodiments of the instant invention.

Materials and Methods.

Unless stated otherwise, reactions were conducted in flame-dried glassware under an atmosphere of nitrogen using anhydrous solvents (either freshly distilled or passed through activated alumina columns). Unless otherwise stated, commercially obtained reagents were used as received. Amines were purified by filtration over basic Brockman Grade 158 Å $Al_2O_3$ (Activity 1), followed by distillation over calcium hydride, prior to use. $Ni(cod)_2$ was obtained from Strem Chemicals and SIPr.HCl was obtained from Sigma Aldrich. Dioxane was purified by distillation over sodium benzophenone ketyl radical and degassed by the freeze-pump-thaw method. Reaction temperatures were controlled using an IKAmag temperature modulator, and unless stated otherwise, reactions were performed at room temperature (rt, approximately 23° C.). Thin-layer chromatography (TLC) was conducted with EMD gel 60 F254 pre-coated plates (0.25 mm) and visualized using a combination of UV, anisaldehyde, ceric ammonium molybdate, iodine, vanillin, and potassium permanganate staining Silicycle Siliaflash P60 (particle size 0.040-0.063 mm) was used for flash column chromatography. $^{1}H$ NMR spectra were recorded on Bruker spectrometers (at 300, 400, 500, 600 MHz) and are reported relative to deuterated solvent signals. Data for $^{1}H$ NMR spectra are reported as follows: chemical shift (δ ppm), multiplicity, coupling constant (Hz) and integration. $^{13}C$ NMR spectra were recorded on Bruker Spectrometers (at 125 MHz). Data for $^{13}C$ NMR spectra are reported in terms of chemical shift. $^{19}F$ NMR (at 300, 400 MHz) spectra are reported in terms of chemical shift. IR spectra were recorded on a Perkin-Elmer 100 spectrometer and are reported in terms of frequency of absorption ($cm^{-1}$).

Melting points are uncorrected and were obtained on a Laboratory Devices MeI-Temp II instrument. High resolution mass spectra were obtained from the UC Irvine Mass Spectrometry Facility.

Illustrative Experimental Procedures.

Please note that the "SI" designations that follow are specific to Example 1.

A. Synthesis of Aryl Sulfamate Substrates

Note: information for the synthesis of the aryl sulfamates shown in Tables 1 and 2 have previously been reported, (King et al., *Can. J. Chem.* 1981, 59, 356-361; Quasdorf et al., *J. Am. Chem. Soc.* 2009, 131, 17748-17749) with the exception of the pyridyl sulfamate SI-2 and naphthyl sulfamate SI-4 shown below.

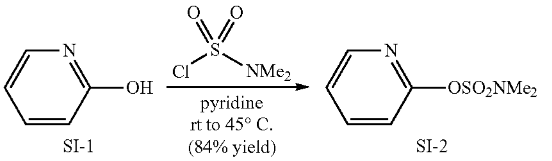

SI-1 SI-2

SI-2 (Table 1, Entry 13).

To a solution of hydroxypyridine SI—I (2.00 g, 21.05 mmol, 1 equiv) in pyridine (21.1 mL) was added dimethylsulfamoyl chloride (2.7 mL, 25.26 mmol, 1.2 equiv) dropwise via syringe. The resulting orange solution was heated to 45° C. and allowed to stir for 24 h. After cooling to 23° C., the solution was diluted with $Et_2O$ (40 mL) and 1 M KOH (15 mL), and the layers were separated. The aqueous layer was extracted with $Et_2O$ (2×40 mL), followed by EtOAc (1×60 mL). The combined organic layers were then washed successively with aqueous $CuSO_4$ (60 mL) and brine (10 mL), dried over $MgSO_4$, and concentrated under reduced pressure. The crude residue was purified by flash chromatography (3:2 Hexanes:EtOAc) to yield SI-2 as a pale yellow oil (3.57 g, 84% yield). $R_f$ 0.29 (2:1 Hexanes: EtOAc); $^1$HNMR (500 MHz, $CDCl_3$): δ 8.26-8.24 (m, 1H), 7.72-7.69 (m, 1H), 7.16 (m, 1H), 7.06 (d, J=2.0, 1H), 2.92 (s, 6H); $^{13}$CNMR (125 MHz, $CDCl_3$): δ 157.1, 147.9, 140.0, 122.1, 115.0, 38.3; IR (film): 2941, 1591, 1430, 1375, 1162 $cm^{-1}$; HRMS-ESI (m/z) $[M+Na]^+$ calcd for $C_7H_{10}N_2O_3SNa$, 225.0310. found, 225.0305.

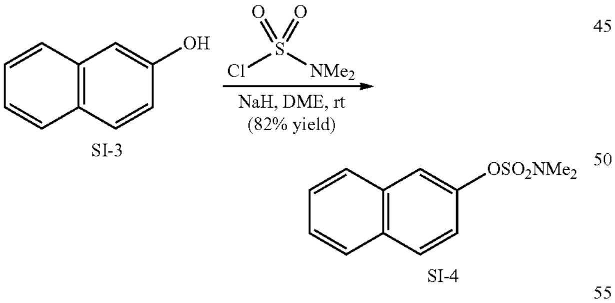

SI-3

SI-4

SI-4 (Table 1, Entry 11).

A round bottom flask was charged with NaH (0.60 g, 15.12 mmol, 1.2 equiv, 60% dispersion in oil). A solution of 2-naphthol (SI-3) (1.82 g, 12.60 mmol, 1 equiv) in DME (32 mL) was added dropwise via cannula to the NaH. A solution of dimethylsulfamoyl chloride (1.30 mL, 11.97 mmol, 0.95 equiv) in DME (10 mL) was then added dropwise via cannula to the reaction vessel. The reaction was allowed to stir for 22 h, and then quenched with $H_2O$ (5 mL). The volatiles were removed under reduced pressure, and then $Et_2O$ (100 mL) and $H_2O$ (70 mL) were added. The layers were separated, and the organic layer was washed successively with 1 M KOH (70 mL) and $H_2O$ (40 mL). The combined aqueous layers were extracted with $Et_2O$ (3×75 mL). The combined organic layers were then washed with brine (2×20 mL), dried over $MgSO_4$, and concentrated under reduced pressure. The crude residue was purified by flash chromatography (4:1 Benzene:Hexanes) to yield 2-naphthylsulfamate SI-4 as a white solid (2.48 g, 82% yield). $R_f$ 0.62 (100% Benzene); $^1$H NMR (500 MHz, $CDCl_3$): δ 7.90-7.82 (m, 3H), 7.76 (d, J=2.3, 1H), 7.55-7.48 (m, 2H), 7.42 (dd, J=8.9, 2.4, 1H), 3.01 (s, 6H); $^{13}$C NMR (125 MHz, $CDCl_3$): δ 147.9, 133.8, 131.9, 130.1, 128.0, 127.9, 127.0, 126.3, 120.9, 119.2, 39.0; IR (film): 2933, 1599, 1457, 1358, 1179 $cm^{-1}$; HRMS-ESI (m/z) $[M+Na]^+$ calcd for $C_{12}H_{13}NO_3SNa$, 274.0514. found, 274.0515.

B. Aminations of Aryl Sulfamates

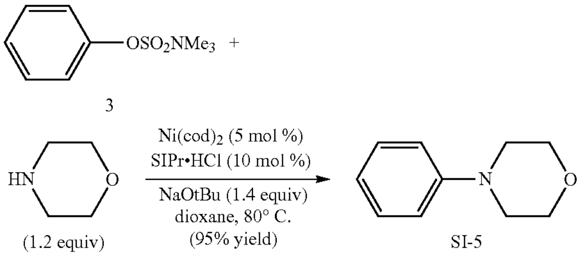

3

(1.2 equiv)

SI-5

Representative Procedure (coupling of phenylsulfamate 3, Table 1, Entry 1) is used as an example). SI-3. A 20-mL reaction vial was charged with $Ni(cod)_2$ (6.8 mg, 0.025 mmol, 5 mol %), SIPr.HCl (21.2 mg, 0.05 mmol, 10 mol %), anhydrous powdered NaOtBu (67.2 mg, 0.7 mmol, 1.4 equiv), and a magnetic stir bar, all in a glove box. Subsequently, a solution of sulfamate substrate 3 (100.5 mg, 0.50 mmol, 1 equiv) and morpholine (52.4 μL, 0.60 mmol, 1.2 equiv) in dioxane (2.5 mL) was added. The vessel was removed from the glove box, and then heated to 80° C. for 3 h. After cooling the reaction vessel to 23° C. and concentrating under reduced pressure, the crude residue was loaded onto a silica gel column (2.5×10 cm) and purified by flash chromatography (9:1 Hexanes:Ethyl acetate) to yield aminated product SI-5 (78.1 mg, 95% yield) as a white solid. $R_f$ 0.29 (9:1 Hexanes:EtOAc). Spectral data match those previously reported (Barker et al., *J. Am. Chem. Soc.* 2009, 131, 15598-15599).

Any modifications of the conditions shown in this representative procedure are specified in the following schemes, which depict all of the results shown in Tables 1 and 2.

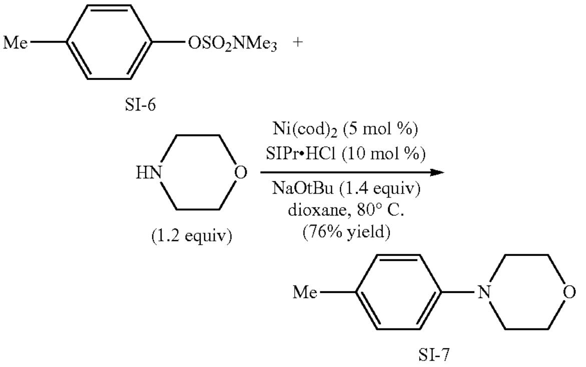

SI-6

(1.2 equiv)

SI-7

SI-7 (Table 1, Entry 2).

Purification by flash chromatography (19:1 Benzene: $Et_2O$) afforded aminated product SI-7 (76% yield) as a white solid. $R_f$ 0.53 (19:1 Benzene:$Et_2O$). Spectral data match those previously reported (Desmarets et al., *J. Org. Chem.* 2002, 67, 3029-3036).

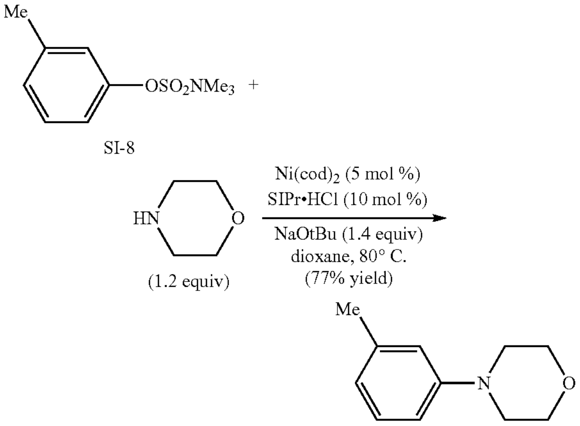

SI-8

SI-9

SI-9 (Table 1, Entry 3).

Purification by flash chromatography (19:1 Benzene: $Et_2O$) afforded aminated product SI-9 (77% yield) as a yellow oil. $R_f$ 0.49 (19:1 Benzene:$Et_2O$). Spectral data match those previously reported (Desmarets et al., *J. Org. Chem.* 2002, 67, 3029-3036).

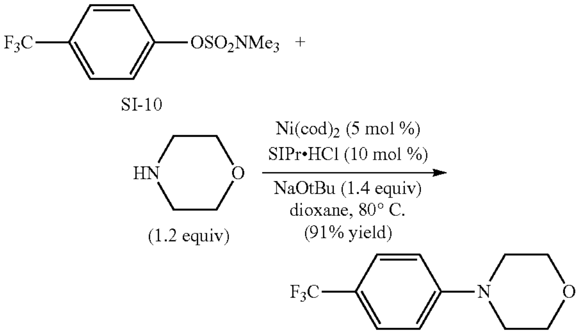

SI-10

SI-11

SI-11 (Table 1, Entry 4).

Purification by flash chromatography (19:1 Benzene: $Et_2O$) afforded aminated product SI-11 (91% yield) as a white solid. $R_f$ 0.63 (19:1 Benzene:$Et_2O$). Spectral data match those previously reported (Guo et al., *Org. Lett.* 2008, 10, 4513-4516).

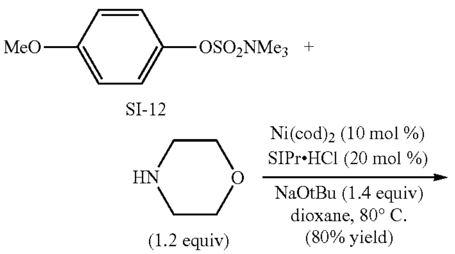

SI-12

-continued

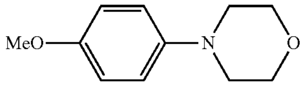

SI-13

SI-13 (Table 1, Entry 5).

Purification by flash chromatography (20:1 Hexanes:Acetone) afforded aminated product SI-13 (80% yield) as a white solid. $R_f$ 0.22 (20:1 Hexanes:Acetone). Spectral data match those previously reported (Wolfe et al., *J. Org. Chem.* 1996, 61, 1133-1135).

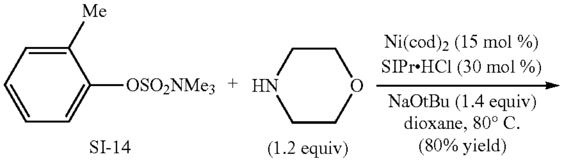

SI-14

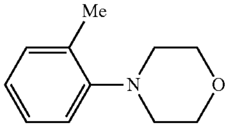

SI-15

SI-15 (Table 1, Entry 6).

Purification by flash chromatography (19:1 Hexanes:EtOAc) afforded aminated product SI-15 (80% yield) as a yellow oil. $R_f$ 0.37 (9:1 Hexanes:EtOAc). Spectral data match those previously reported (Desmarets et al., *J. Org. Chem.* 2002, 67, 3029-3036).

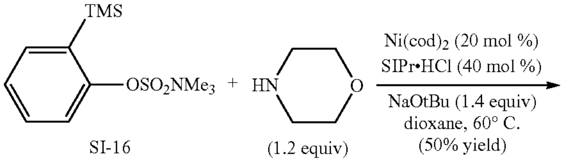

SI-16

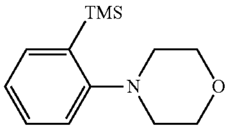

SI-17

SI-17 (Table 1, Entry 7).

Purification by flash chromatography (5:1 Benzene: Hexanes) afforded aminated product SI-17 (50% yield) as a white solid. $R_f$ 0.31 (100% Benzene); $^1$HNMR (500 MHz, $CDCl_3$): δ 7.50 (d, J=7.3, 1H), 7.41 (t, J=7.1, 1H), 7.33 (d, J=7.9, 1H), 7.22 (t, J=7.2, 1H), 3.85 (t, J=4.3, 4H), 2.89 (bs, 4H), 0.31 (s, 9H); $^{13}$CNMR (125 MHz, $CDCl_3$): δ 159.5, 138.8, 135.6, 130.5, 125.9, 122.8, 67.4, 54.5, 0.17; IR (film): 2852, 1583, 1473, 1258, 1109 $cm^{-1}$; HRMS-ESI (m/z) $[M+H]^+$ calcd for $C_{13}H_{21}NOSiH$, 236.1471. found, 236.1466.

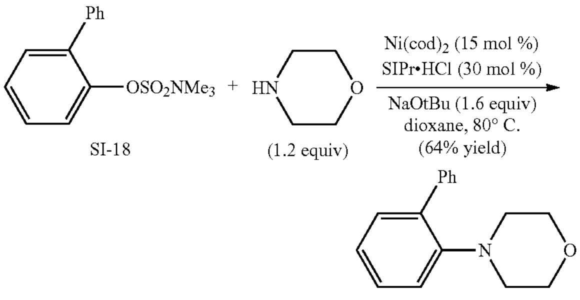

SI-18 (1.2 equiv)

SI-19

SI-19 (Table 1, Entry 8).

Purification by flash chromatography (100% Benzene) afforded aminated product SI-19 (64% yield) as an off-white solid. $R_f$ 0.53 (100% Benzene); $^1$HNMR (500 MHz, $CDCl_3$): δ 7.66 (dd, J=8.2, 1.2, 2H), 7.42 (t, J=7.6, 2H), 7.35-7.30 (m, 2H), 7.28 (dd, J=7.6, 1.6, 1H), 7.12 (td, J=7.5, 1.1, 1H), 7.05 (dd, J=8.1, 0.8, 1H), 3.62 (t, J=4.6, 4H), 2.84 (t, J=4.6, 4H); $^{13}$CNMR (125 MHz, $CDCl_3$): δ 150.1, 141.1, 135.1, 131.7, 128.9, 128.5, 128.3, 127.0, 123.0, 118.1, 67.1, 51.6; IR (film): 2950, 2815, 1593, 1480, 1439, 1221, 1110 $cm^{-1}$; HRMS-ESI (m/z) $[M+H]^+$ calcd for $C_{16}H_{17}NOH$, 240.1388. found, 240.1394.

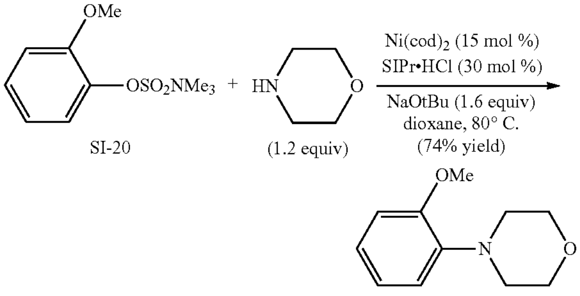

SI-20 (1.2 equiv)

SI-21

SI-21 (Table 1, Entry 9).

Purification by flash chromatography (20:1 Hexanes:Acetone) afforded aminated product SI-21 (74% yield) as a yellow oil. $R_f$ 0.16 (20:1 Hexanes:Acetone). Spectral data match those previously reported (Li et al., *J. Organomet. Chem.* 2007, 692, 3732-3742).

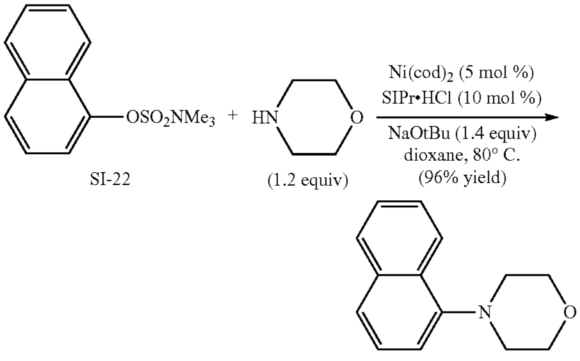

SI-22 (1.2 equiv)

SI-23

SI-23 (Table 1, Entry 10).

Purification by flash chromatography (9:1 Hexanes:EtOAc) afforded aminated product SI-23 (96% yield) as a white solid. $R_f$ 0.38 (9:1 Hexanes:EtOAc). Spectral data match those previously reported (Desmarets et al., *J. Org. Chem.* 2006, 71, 1351-1361).

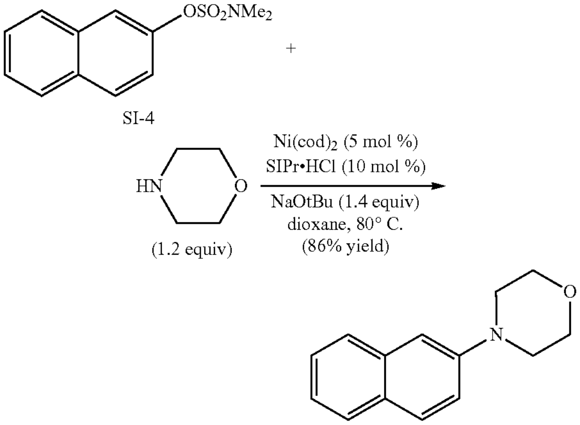

SI-4

(1.2 equiv)

SI-24

SI-24 (Table 1, Entry 11).

Purification by flash chromatography (9:1 Hexanes:EtOAc) afforded aminated product SI-24 (86% yield) as a white solid. $R_f$ 0.32 (9:1 Hexanes:EtOAc). Spectral data match those previously reported (Gao et al., *J. Org. Chem.* 2008, 73, 1624-1627).

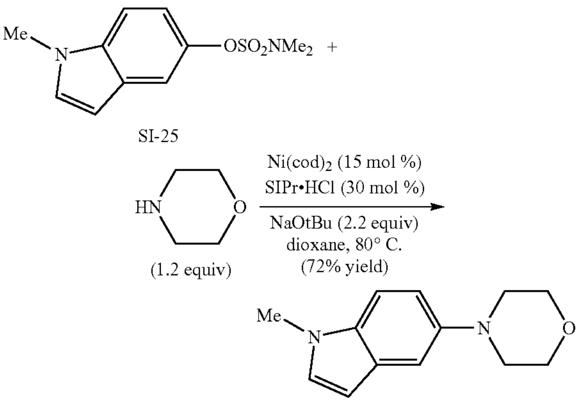

SI-25

(1.2 equiv)

SI-26

SI-26 (Table 1, Entry 12).

Purification by flash chromatography (4:1 Hexanes:Acetone) afforded aminated product SI-25 (72% yield) as a off-white solid. $R_f$ 0.31 (4:1 Hexanes:Acetone); $^1$HNMR (500 MHz, $CDCl_3$): δ 7.25 (d, J=8.8, 1H), 7.16 (d, J=2.2, 1H), 7.03-6.97 (m, 2H), 6.41 (d, J=3.0, 1H), 3.91 (t, J=4.7, 4H), 3.76 (s, 3H), 3.13 (t, J=4.7, 4H); $^{13}$CNMR (125 MHz, $CDCl_3$): δ 145.9, 132.9, 129.5, 129.2, 115.2, 110.1, 108.0, 100.8, 67.6, 52.4, 33.2; IR (film): 3093, 2968, 1616, 1490, 1231, 1115 $cm^{-1}$; HRMS-ESI (m/z) $[M+H]^+$ calcd for $C_{13}H_{16}N_2OH$, 217.1341. found, 217.1342.

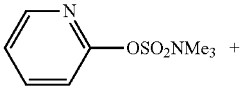

SI-2

-continued

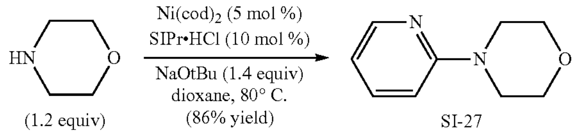

(1.2 equiv)

SI-27

SI-27 (Table 1, Entry 13).

Purification by flash chromatography (2:1 Hexanes:EtOAc) afforded aminated product SI-27 (86% yield) as a pale yellow oil. $R_f$ 0.28 (9:1 Benzene:$Et_2O$). Spectral data match those previously reported (Wagaw et al., *J. Org. Chem.* 1996, 61, 7240-7241).

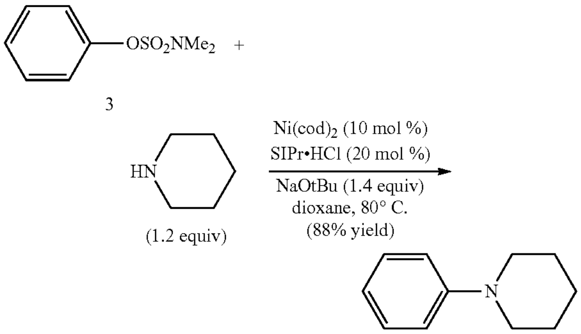

3

(1.2 equiv)

SI-28

SI-28 (Table 2, Entry 1).

Purification by flash chromatography (50:1 Hexanes:EtOAc) afforded aminated product SI-28 (88% yield) as a clear oil. $R_f$ 0.29 (50:1 Hexanes:EtOAc). Spectral data match those previously reported (Shimasaki et al., *Angew. Chem. Int. Ed.* 2010, 49, 2929-2932).

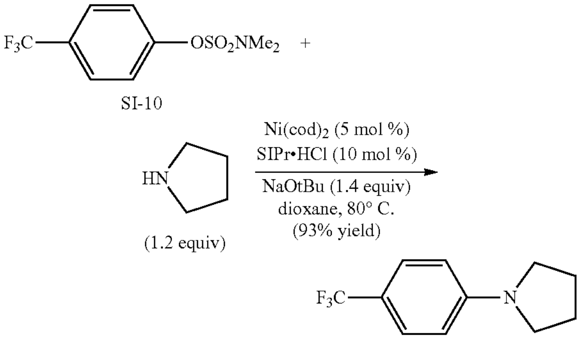

SI-10

(1.2 equiv)

SI-29

SI-29 (Table 2, Entry 2).

Purification by flash chromatography (20:1 Hexanes: $Et_2O$) afforded aminated product SI-29 (93% yield) as a white solid. Spectral data match those previously reported (Brenner, E.; Schneider, R.; Fort, Y. *Tetrahedron* 1999, 55, 12829-12842).

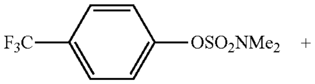

SI-10

-continued

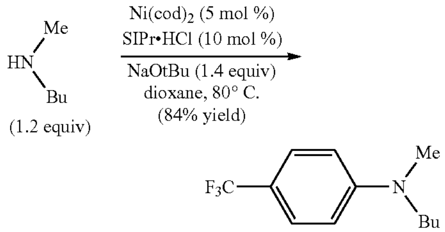

(1.2 equiv)

SI-30

SI-30 (Table 2, Entry 3).

Purification by flash chromatography (20:1 Hexanes: $Et_2O$) afforded aminated product SI-30 (84% yield) as a clear oil. $R_f$ 0.59 (20:1 Hexanes:$Et_2O$). $^1$HNMR (300 MHz, $CDCl_3$): δ 7.42 (d, J=9.0, 2H), 6.66 (d, J=8.7, 2H), 3.35 (t, J=7.3, 2H), 2.97 (s, 3H), 1.62-1.52 (m, 2H), 1.35 (sextet, J=7.2, 2H), 0.95 (t, J=7.4, 3H), $^{13}$CNMR (125 MHz, $CDCl_3$): δ 151.4, 126.6 (q, J=7.4, 3.7), 125.4 (q, J=536.4, 268.3), 117.0 (q, J=64.4, 32.0), 110.9, 52.9, 38.4, 28.9, 20.4, 14.0; $^{19}$FNMR (300 MHz, $CDCl_3$): −60.8; IR (film): 2960, 2933, 2876, 1616, 1533, 1322, 1197, 1100, 1068 $cm^{-1}$; HRMS-ESI (m/z) $[M+H]^+$ calcd for $C_{12}H_{16}F_3$, 232.1313. found 232.1307.

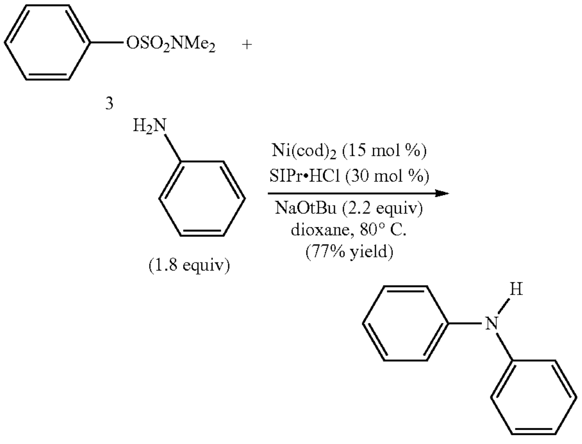

3

(1.8 equiv)

SI-31

SI-31 (Table 2, Entry 4).

Purification by flash chromatography (4:1 Hexanes: $CH_2Cl_2$) afforded aminated product SI-31 (77% yield) as a yellow solid. $R_f$ 0.28 (4:1 Hexanes:$CH_2Cl_2$). Spectral data match those previously reported (Desmarets et al., *J. Org. Chem.* 2002, 67, 3029-3036).

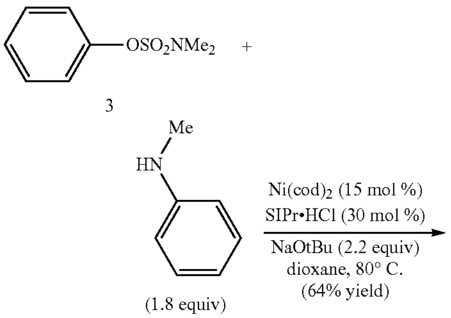

3

(1.8 equiv)

-continued

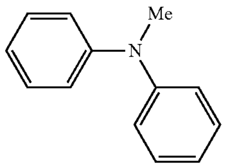

SI-32

SI-32 (Table 2, Entry 5).

Purification by flash chromatography (100% Hexanes) afforded aminated product SI-32 (64% yield) as a yellow oil. $R_f$ 0.25 (100% Hexanes). Spectral data match those previously reported (Desmarets et al., *J. Org. Chem.* 2002, 67, 3029-3036).

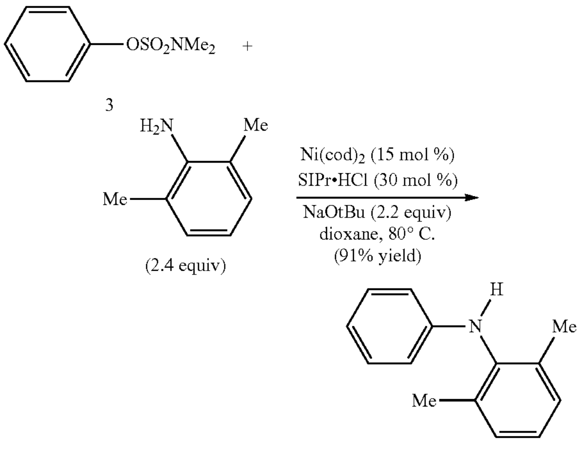

SI-33

SI-33 (Table 2, Entry 6).

Purification by flash chromatography (20:1 Hexanes: $Et_2O$) afforded aminated product SI-33 (91% yield) as a clear oil. $R_f$ 0.41 (20:1 Hexanes:$Et_2O$). Spectral data match those previously reported (Desmarets et al., *J. Org. Chem.* 2002, 67, 3029-3036).

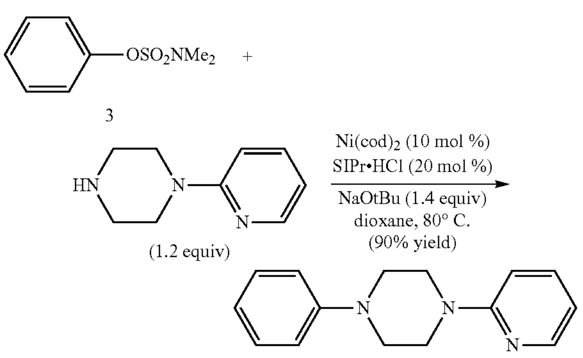

SI-34

SI-34 (Table 2, Entry 7).

Purification by flash chromatography (8:1 Hexanes:EtOAc) afforded aminated product SI-34 (90% yield) as a white solid. $R_f$ 0.30 (8:1 Hexanes:EtOAc). Spectral data match those previously reported (Shimasaki et al., *Angew. Chem. Int. Ed.* 2010, 49, 2929-2932).

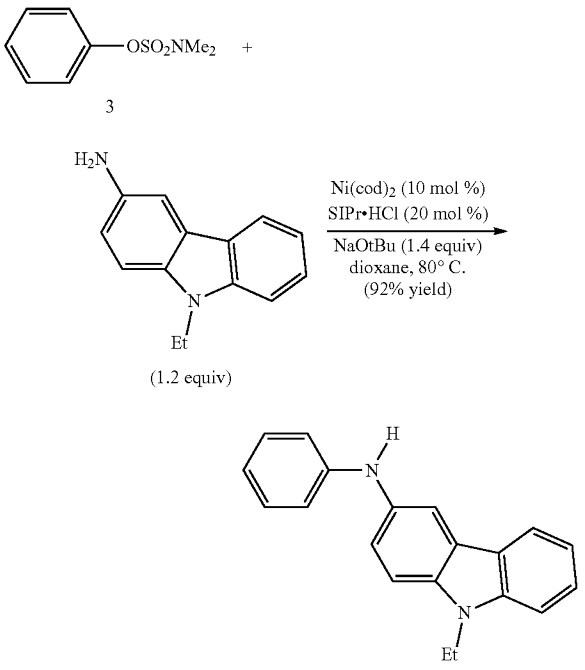

SI-35

SI-35 (Table 2, Entry 8).

Purification by flash chromatography (300:150:1 Hexanes:$CH_2Cl_2$:$Et_3N$) afforded aminated product SI-35 (92% yield) as a white solid. $R_f$ 0.30 (2:1 Hexanes:$CH_2Cl_2$). $^1$HNMR (500 MHz, $C_6D_6$): δ 7.94 (d, J=6.7, 1H), 7.74 (d, J=1.7, 1H), 7.39 (t, J=7.6, 1H), 7.21-7.16 (m, 4H), 7.07 (d, J=8.2, 1H), 6.95 (d, J=8.5, 1H), 6.91 (d, J=8.4, 2H), 6.82, (td, J=7.4, 0.8, 1H), 5.15 (s, 1H), 3.69 (q, J=7.2, 2H), 0.92 (t, J=7.3, 3H); $^{13}$CNMR (125 MHz, $C_6D_6$): δ 146.9, 140.8, 137.0, 134.9, 129.7, 128.3, 128.3, 128.2, 128.1, 127.9, 126.0, 124.2, 123.3, 121.9, 121.0, 119.4, 119.1, 115.6, 114.4, 109.2, 108.8, 37.4, 13.6; IR (film): 3383, 3048, 2974, 1598, 1504, 1489, 1470, 1299, 1229, 1150 $cm^{-1}$; HRMS-ESI (m/z) $[M+H]^+$ calcd for $C_{20}H_{18}N_2$, 287.1548. found 287.1551.

C. Synthesis of Linezolid

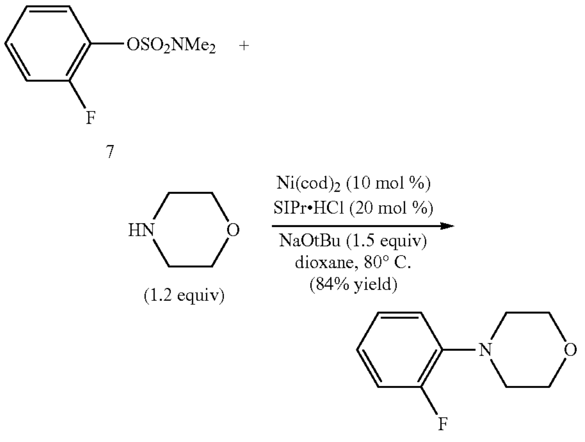

8

Amine 8.

A 20-mL reaction vial was charged with $Ni(cod)_2$ (82.2 mg, 0.30 mmol, 10 mol %), SIPr.HCl (255.8 mg, 0.60 mmol, 20 mol %), anhydrous powdered NaOtBu (432.3 mg, 4.5 mmol, 1.5 equiv), and a magnetic stir bar, all in a glove box. Subsequently, a solution of sulfamate 7 (658 mg, 3.0 mmol, 1 equiv) and morpholine (310 μL, 3.6 mmol, 1.2 equiv) in dioxane (15 mL) was added. The vessel was sealed and removed from the glove box, then heated to 80° C. for 3 h. After cooling the reaction vessel to 23° C. and concentrating under reduced pressure, the crude residue was purified by flash chromatography (19:1 Benzene:$Et_2O$) to yield aminated product 8 (457 mg, 84% yield) as an off-white solid. $R_f$ 0.28 (19:1 Benzene:$Et_2O$). Spectral data match those previously reported (Fasani et al., *Org. Biomol. Chem.* 2008, 6, 4634-4642).

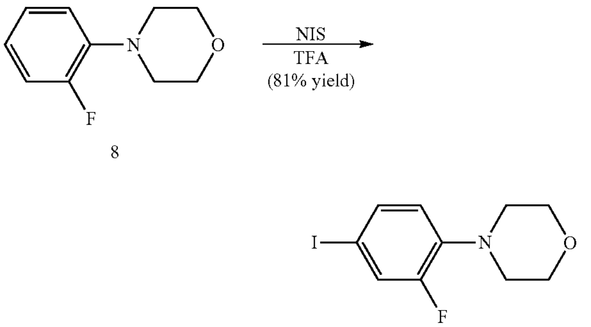

8

9

Iodide 9.

A 20-mL reaction vial was charged with amine 8 (402 mg, 2.12 mmol, 1 equiv) and N-iodosuccinimide (574 mg, 2.55 mmol, 1.2 equiv). TFA (2.2 mL) was added, and the reaction vessel was flushed $N_2$ and sealed with a Teflon-lined cap. After stirring at 23° C. for 14 h, the reaction was quenched successively with solutions of saturated aqueous sodium thiosulfate (5 mL) and saturated aqueous sodium carbonate (5 mL). The aqueous layer was extracted with $Et_2O$ (3×20 mL) The combined organic layers were then dried over $MgSO_4$, and concentrated under reduced pressure. The crude product was purified by flash chromatography (17:2:1 Benzene:Hexanes:$Et_2O$) to yield iodide 9 as a white solid (676 mg, 81% yield). $^1$HNMR (600 MHz, $CDCl_3$): δ 7.34-7.32 (m, 2H), 6.64 (t, J=9.0, 1H), 3.83 (t, J=5.0, 4H), 3.03 (t, J=5.0, 4H), $^{13}$CNMR (125 MHz, $CDCl_3$): δ 155.3 (d, J=252.0), 140.7 (d, J=9.0), 133.7 (d, J=5.0), 125.3 (d, J=23.0), 120.3 (d, J=3.0), 83.2 (d, J=8.0), 66.9, 50.7 (d, J=3.0); $^{19}$FNMR (400 MHz, $CDCl_3$) −120.5; IR (film): 2962, 2856, 1598, 1491, 1116 $cm^{-1}$. HRMS-ESI (m/z) $[M+H]^+$ calcd for $C_{10}H_{18}FINO$, 307.9948. found 307.9940.

10

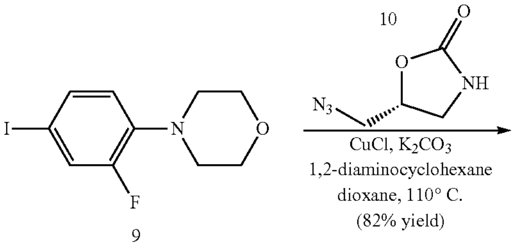

9

-continued

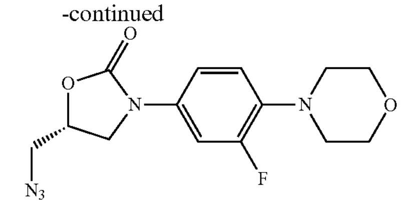

11

Azide 11.

A 1-dram vial was charged with $K_2CO_3$ (359 mg, 2.60 mmol, 2 equiv) and a magnetic stir bar. The vial and contents were flame-dried under reduced pressure, then allowed to cool under $N_2$. Iodide 9 (400 mg, 1.30 mmol, 1 equiv) and oxazolidinone 10 (Zhang et al., *J. Comb. Chem.* 2007, 9, 17-19) (185 mg, 1.30 mmol, 1 equiv) were added. The vial was then evacuated and backfilled with $N_2$ three times and brought into a glove box. CuCl (12.7 mg, 0.13 mmol, 10 mol %) was added and the reaction vessel was removed from the glove box and placed under an atmosphere of $N_2$. (±)-trans-1,2-diaminocyclohexane (31.2 μL, 0.26 mmol, 20 mol %) was then added, followed by anhydrous dioxane (720 μL). The reaction vessel was shielded from light, sealed with a Teflon-coated cap, and heated to 110° C. After 15 h, the reaction was allowed to cool to 23° C. The residue was diluted in EtOAc (10 mL) and filtered over a pad of celite (EtOAc eluent, 30 mL). Concentrated under reduced pressure afforded the crude product, which was further purified by flash chromatography (1:1 Benzene:$Et_2O$) to yield azide 11 as a yellow solid (344 mg, 82% yield). $R_f$ 0.25 (1:1 Benzene:$Et_2O$). Spectral data match those previously reported (Brickner et al., *J. Med. Chem.* 1996, 39, 673-679).

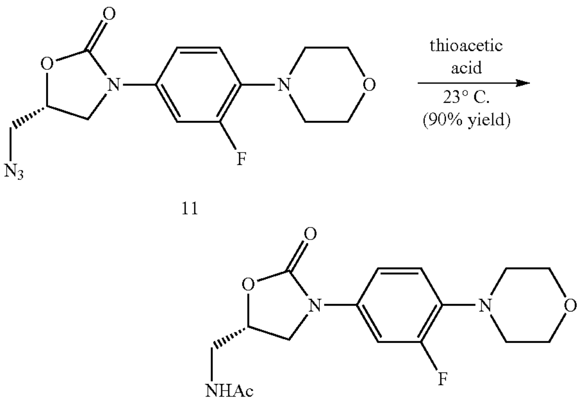

11 linezolid (4)

Linezolid (4).

A solution of azide 11 (87.0 mg, 0.247 mmol, 1 equiv) in thioacetic acid (0.17 mL, 2.487 mmol, 10 equiv) was stirred at 23° C. After 7 h, the reaction was quenched by the addition of a KOH solution (5.0 mL, 1 M aqueous). The aqueous layer was saturated by the addition of NaCl, and then extracted sequentially with EtOAc (3×5 mL), $CH_2Cl_2$ (3×5 mL), and $CHCl_3$ (3×5 mL) at pH=14. The aqueous layer was then acidified with HCl (1 M aqueous) to pH=5 and extracted with EtOAc (3×5 mL). The combined organic layers were dried over $Na_2SO_4$, and then concentrated under reduced pressure. The crude product was purified by flash chromatography (100% EtOAc→9:1 EtOAc:MeOH) to afford linezolid (4) as an off-white solid (75.3 mg, 90% yield). $R_f$ 0.38 (100% EtOAc). $^{19}F$ NMR (400 MHz, $CDCl_3$): δ −120.7. Spectral data match those previously reported (Mallesham et al., *Org. Lett.* 2003, 5, 963-965).

NMR spectra for above-noted compounds was published as supplemental information in S. D. Ramgren et al., *Angew. Chem. Int. Ed.,* 2011, 50, 2171-2173, is available online, see: angewandte.org.

Example 2

Nickel-Catalyzed Amination of Aryl Carbamates and Sequential Site-Selective Cross-Couplings In this Example, we report the amination of aryl carbamates using nickel-catalysis. The methodology is broad in scope with respect to both coupling partners and delivers aminated products in synthetically useful yields. Computational studies provide the full catalytic cycle of this transformation, and suggest that reductive elimination is the rate-determining step. Given that carbamates are easy to prepare, robust, inert to Pd-catalysis, and useful for arene functionalization, these substrates are particularly attractive partners for use in synthesis. The sequential use of carbamate functionalization/site-selective cross-couplings processes highlights the utility of this methodology.

Introduction

As noted above, the discovery of methods for the assembly of carbon-nitrogen bonds continues to be an active area of research. Among the numerous tactics available for C—N bond formation, transition metal-catalyzed processes, led by Buchwald and Hartwig, have become some of the most widely used methods in chemical synthesis (see, e.g. J. P. Wolfe et al., *Acc. Chem. Res.,* 1998, 31, 805-818; J. F. Hartwig, *Angew. Chem. Int. Ed.,* 1998, 37, 2046-2067; A. R. Muci and S. L. Buchwald, Practical Palladium Catalysts for C—N and C—O Bond Formation, in *Topics in Current Chemistry, Vol.* 219 (Ed: N. Miyaura), Springer-Verlag, Berlin, 2001, p 131; M. Kienle et al., *Eur. J. Org. Chem.,* 2007, 4166-4176; J. F. Hartwig, Nature, 2008, 455, 314-322; D. S. Surry et al., *Chem. Sci.,* 2011, 2, 27-50). Recent efforts have focused on the catalytic amination of phenol derivatives, as phenols are readily available, with certain analogs being ideally poised for the synthesis of polysubstituted arenes. For examples of tosylate and mesylate amination, see: B. C. Hamann and J. F. Hartwig, *J. Am. Chem. Soc.,* 1998, 120, 7369-7370; A. H. Roy and J. F. Hartwig, *J. Am. Chem. Soc.,* 2003, 125, 8704-8705; T. Ogata and J. F. Hartwig, J. Am. Chem. Soc., 2008, 130, 13848-13849; C.-Y. Gao and L.-M. Yang, *J. Org. Chem.,* 2008, 73, 1624-1627; B. P. Fors et al., *J. Am. Chem. Soc.,* 2008, 130, 13552-13554; C. M. So et al., *Angew. Chem. Int. Ed* 2008, 47, 6402-6406. For the amination of aryl pivalates, see: T. Shimasaki et al., *Angew. Chem. Int. Ed.,* 2010, 49, 2929-2932. For sulfamate amination, see: S. D. Ramgren et al., *Angew. Chem. Int. Ed.,* 2011, 50, 2171-2173; L. Ackermann, R. Sandmann and W. Song, *Org. Lett.,* 2011, 13, 1784-1786). For recent reviews and highlights regarding the cross-coupling of phenolic derivatives, see: B. M. Rosen et al., *Chem. Rev.,* 2011, 111, 1346-1416; B.-J. Li, D.-G. Yu, C.-L. Sun, and Z.-J. Shi, *Chem. Eur. J.,* 2011, 17, 1728-1759; D.-G. Yu, B.-J. Li and Z.-J. Shi, *Acc. Chem. Res.,* 2010, 43, 1486-1495; C. E. I. Knappke, A. Jacobi von Wangelin, *Angew. Chem. Int. Ed.,* 2010, 49, 3568-3570; L. J. Goossen, K. Goossen and C. Stanciu, *Angew. Chem. Int. Ed.,* 2009, 48, 3569-3571).

Figure 3:
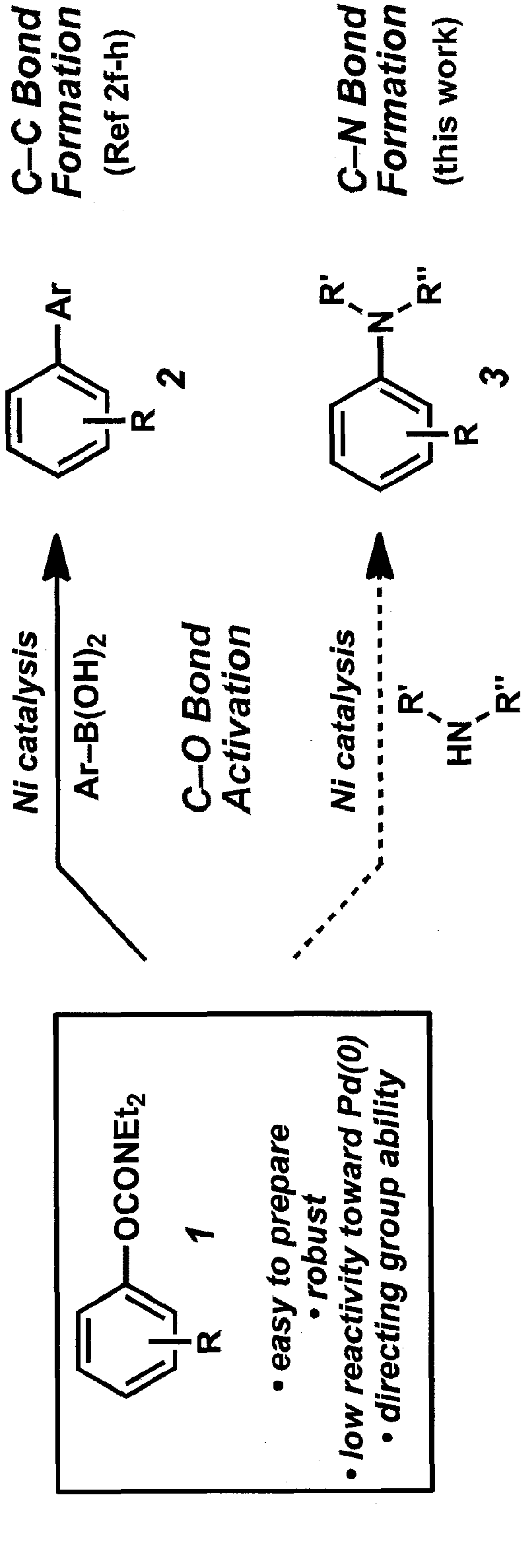
FIG. 3 provides a schematic showing known C—C and proposed C—N bond formation reactions using aryl carbamates as substrates.

One particularly attractive class of electrophilies are the N,N-dialkyl aryl O-carbamates (1, FIG. 3). Features of these substrates include their ease of preparation, pronounced stability, and low reactivity toward Pd(0). For example, Aryl N,N-diethylcarbamates are readily prepared from aryl alcohols and commercially available N,N-diethylcarbamoyl chloride. The latter reagent costs approximately $20-25 per mol ($0.15-$0.20 per gram) from common chemical suppliers, such as Alfa Aesar and Aldrich Chemical Co., Inc. Furthermore, aryl carbamates can be used for arene functionalization, prior to a cross-coupling event, using either electrophilic aromatic substitution, (M. B. Smith and J. March, in *March's Advanced Organic Chemistry,* 6th ed., John Wiley & Sons, Inc., New Jersey, 2007, p 670) directed o-metallation, (V. Snieckus, *Chem. Rev.,* 1990, 90, 879-933; C. G. Hartung and V. Snieckus, in *Modern Arene Chemistry* (Ed.: D. Astruc), Wiley-VCH, New York, 2002, pp 330-367; T. Macklin and V. Snieckus, in *Handbook of C—H Transformations* (Ed.: G. Dyker), Wiley-VCH, New York, 2005, pp 106-119) or recently described Pd- or Ir-catalyzed methods (R. B. Bedford et al., *Org. Biomol. Chem.,* 2009, 7, 4853-4857; X. Zhao et al., *J. Am. Chem. Soc.,* 2010, 132, 5837-5844; T. Nishikata et al., *J. Am. Chem. Soc.,* 2010, 132, 4978-4979; K. Yamazaki et al., *Org. Lett.,* 2010, 12, 3978-3981). Other phenol-based amination partners cannot be used effectively for directed metallation/functionalization. Specifically, aryl sulfonates and pivalates are not suitable substrates, whereas aryl methyl ethers are poor metalation substrates. Aryl sulfamates can be used in ortho-lithiation, but the sulfamate directing group ability is approximately 20× less compared to carbamates.

Although aryl carbamates have been employed in C—C bond forming processes (FIG. 3, 1→2), their use in amination reactions (1→3), has been less explored. For the use of aryl carbamates in C—C bond forming processes, see: K. W. Quasdorf et al., *Am. Chem. Soc.,* 2009, 131, 17748-17749; A. Antoft-Finch et al., *J. Am. Chem. Soc.,* 2009, 131, 17750-17752; L. Xi et al., *Org. Lett.,* 2010, 12, 884-887). For C—C bond forming processes involving aryl pivalates, methyl ethers, or sulfamates, see: K. W. Quasdorf et al., *J. Am. Chem. Soc.,* 2008, 130, 14422-14423; B.-T. Guan et al., *J. Am. Chem. Soc.,* 2008, 130, 14468-14470; B.-J. Li et al., *Angew. Chem. Int. Ed.,* 2008, 47, 10124-10127; M. Tobisu et al., *Angew. Chem. Int. Ed.,* 2008, 47, 4866-4869; J. W. Dankwardt, *Angew. Chem. Int. Ed.,* 2004, 43, 2428-2432; T. K. Macklin and V. Snieckus, *Org. Lett.,* 2005, 7, 2519-2522; P. M. Wehn and J. Du Bois, *Org. Lett.,* 2005, 7, 4685-4688). Specifically, during the course of our own studies, only a single example of carbamate amination was reported using the N,N-diethylcarbamate derivative of phenol. Considering the importance of transition metal-catalyzed amination reactions in modern synthetic chemistry, coupled with the salient features of carbamate electrophiles, we sought to develop a general method for carbamate amination. In this Example, we report the broad scope of carbamate amination methodology, as well as a computational study of the full catalytic cycle. In addition, we demonstrate the value of these reaction partners for the synthesis of polysubstituted aryl amines using sequential carbamate functionalization/site-selective cross-coupling methodologies.

Results and Discussion

Optimization and Substrate Scope

To initiate studies, we attempted the amination of diethylnaphthylcarbamates with morpholine under a variety of reaction conditions. Although Ni/$PCy_3$-based conditions have been useful for achieving C—C bond formation, it was not possible to achieve amination using related procedures. This finding is likely not surprising since C—N and C—C bond forming processes would proceed through fairly different mechanistic pathways (although the initial oxidative addition step would be common to both processes). After conducting an extensive survey of reaction parameters (e.g., nickel catalysts, ligands, solvents, bases, temperature, etc.) it was observed that combinations of Ni catalysts and N-heterocyclic carbene ligands promoted the desired amination. Our laboratory and Chatani's have previously noted analogous findings in couplings of sulfamates and pivalates, respectively. For the amination of aryl pivalates, see: T. Shimasaki et al., *Angew. Chem. Int. Ed.,* 2010, 49, 2929-2932. For sulfamate amination, see: S. D. Ramgren et al., *Angew. Chem. Int. Ed.,* 2011, 50, 2171-2173; L. Ackermann, R. Sandmann and W. Song, *Org. Lett.,* 2011, 13, 1784-1786.

Figure 7C:
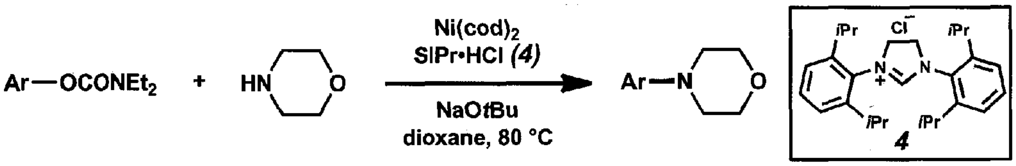
Figure 7C:
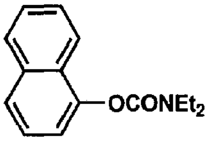
Figure 7C:
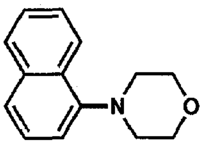
Figure 7C:
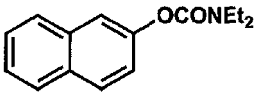
Figure 7C:
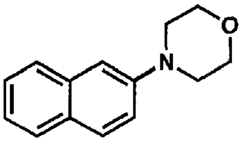
Figure 7C:
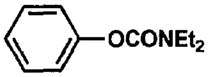
Figure 7C:
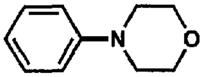
Figure 7C:
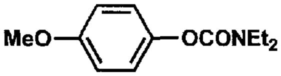
Figure 7C:
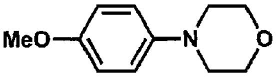
Figure 7C:
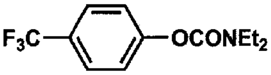
Figure 7C:
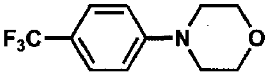
Figure 7C:
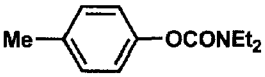
Figure 7C:
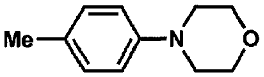
Figure 7C:
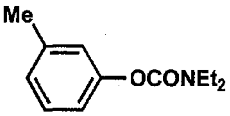
Figure 7C:
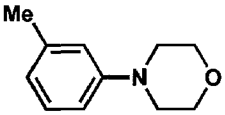

We identified the use of catalytic $Ni(cod)_2$, SIPr.HCl (4), (SIPr.HCl (4), which is commercially available (CAS#258278-25-0)) and NaOtBu, in dioxane at 80° C. as optimal reaction conditions for amination and investigated the carbamate substrate scope (Table 3, FIG. 7C). Although these conditions are broadly useful, aminations of certain substrates proceed even at ambient temperature. For example, N,N-diethylphenylcarbamate undergoes coupling with morpholine in 24 h at 23° C. using 5 mol % catalyst (–90% conversion based on $^1$H NMR analysis with internal standard). For certain substrates, the use of standard reaction conditions led to slow conversion to aminated product. In these cases, higher catalyst, ligand, and/or amine loadings could be used to expedite reaction progress as indicated in Tables 3-5. The formation of undesired byproducts is not typically observed). Naphthyl carbamates, which typically function well in the Suzuki-Miyaura coupling, were excellent substrates for the amination (entries 1 and 2). Non-fused aromatics were also tolerated by the methodology (entries 3-7). The electron-donating methoxy group (entry 4) and the electron-withdrawing trifluoromethyl group (entry 5) were suitable substrates. Methyl substituents at the para and meta positions were tolerated as well (entries 6 and 7).

Figure 7D:
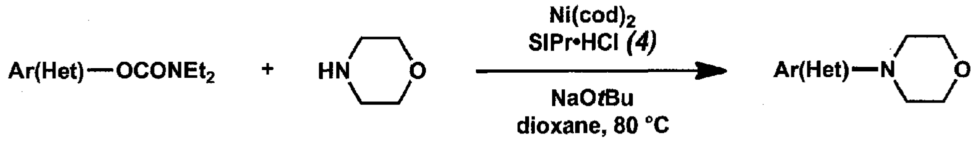
Figure 7D:
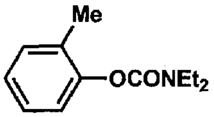
Figure 7D:
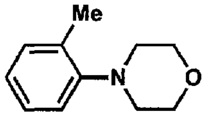
Figure 7D:
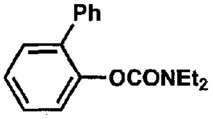
Figure 7D:
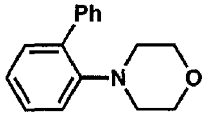
Figure 7D:
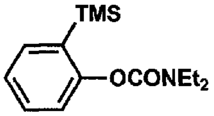
Figure 7D:
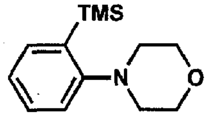
Figure 7D:
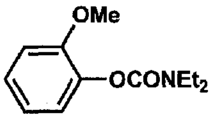
Figure 7D:
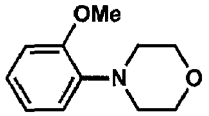
Figure 7D:
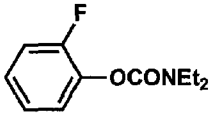
Figure 7D:
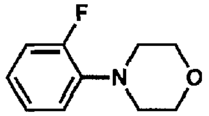
Figure 7D:
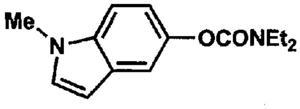
Figure 7D:
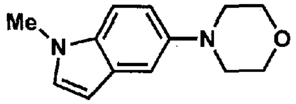
Figure 7D:
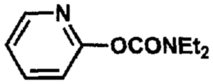
Figure 7D:
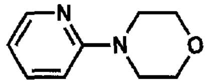

The feasibility of coupling o-substituted carbamates, in addition to heterocyclic substrates, was examined (Table 4, FIG. 7D). For certain substrates, the use of standard reaction conditions led to slow conversion to aminated product. In these cases, higher catalyst, ligand, and/or amine loadings could be used to expedite reaction progress as indicated in Tables 3-5. The formation of undesired byproducts is not typically observed. Of note, o-substituted aryl carbamates are readily accessible by functionalization of the parent carbamate using directed metallation (V. Snieckus, *Chem. Rev.,* 1990, 90, 879-933; C. G. Hartung and V. Snieckus, in *Modern Arene Chemistry* (Ed.: D. Astruc), Wiley-VCH, New York, 2002, pp 330-367; T. Macklin and V. Snieckus, in *Handbook of C—H Transformations* (Ed.: G. Dyker), Wiley-VCH, New York, 2005, pp 106-119) or transition metal-catalyzed processes (R. B. Bedford et al., *Org. Biomol. Chem.,* 2009, 7, 4853-4857; X. Zhao et al., *J. Am. Chem. Soc.,* 2010, 132, 5837-5844; T. Nishikata et al., *J. Am. Chem. Soc.,* 2010, 132, 4978-4979; K. Yamazaki et al., *Org. Lett.,* 2010, 12, 3978-3981), but have proven to be exceptionally challenging substrates in the recently discovered nickel-catalyzed Suzuki-Miyaura coupling. For the use of aryl carbamates in C—C bond forming processes, see: K. W. Quasdorf et al., *Am. Chem. Soc.,* 2009, 131, 17748-17749; A. Antoft-Finch et al., *J. Am. Chem. Soc.,* 2009, 131, 17750-17752; L. Xi et al., *Org. Lett.,* 2010, 12, 884-887. We were delighted to find that a range of o-substituted phenylcarbamates could be employed in our amination methodology. Candidate compounds can be easily tested using the methods disclosed herein. Using such tests, we determined that the carbamate derived from 2,6-dimethylphenol fails to undergo amination under our reaction conditions. Carbon substituents were well-tolerated (entries 1 and 2), as were heteroatoms (entries 3-5). Furthermore, heterocyclic substrates containing indole or pyridine underwent coupling with morpholine under nickel catalysis (entries 6 and 7).

Figure 7E:
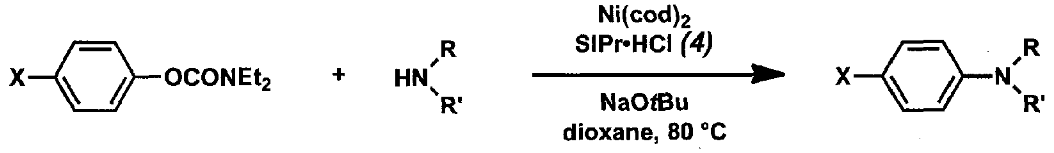
Figure 7E:
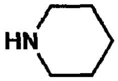
Figure 7E:
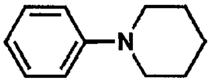
Figure 7E:
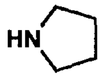
Figure 7E:
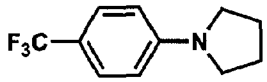
Figure 7E:
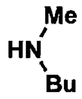
Figure 7E:
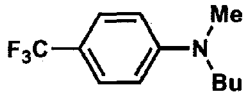
Figure 7E:
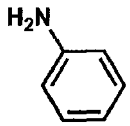
Figure 7E:
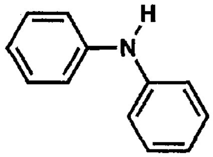
Figure 7E:
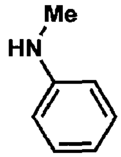
Figure 7E:
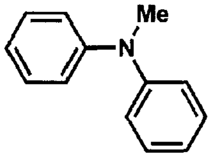
Figure 7E:
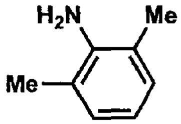
Figure 7E:
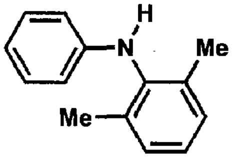
Figure 7E:
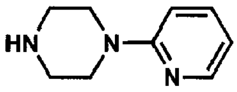
Figure 7E:
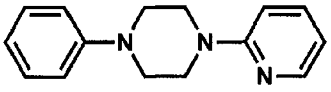
Figure 7E:
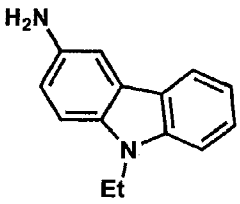
Figure 7E:
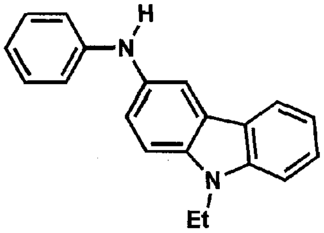

As shown in Table 5 (FIG. 7E), a variety of amines can be employed in the carbamate amination. For certain substrates, the use of standard reaction conditions led to slow conversion to aminated product. In these cases, higher catalyst, ligand, and/or amine loadings could be used to expedite reaction progress as indicated in Tables 3-5. The formation of undesired byproducts is not typically observed. Attempts to effect the amination of primary aliphatic amines, such as benzyl amine and n-butylamine, led to the recovery of starting material, albeit with some non-specific decomposition). Both cyclic and acyclic secondary amines were tolerated (entries 1-3), in addition to anilines (entries 4-6). Of note, use of the sterically congested 2,6-dimethylaniline delivered the corresponding aminated product in 92% yield (entry 6). The methodology also allows for the coupling of amines with appended heterocycles (entries 7 and 8).

Computational Studies

Although the mechanism of palladium-based aminations has been studied computationally. No theoretical studies of nickel-catalyzed aminations have been reported. Furthermore, computational studies involving unconventional phenol-based electrophiles (e.g., esters, carbamates, sulfamates) are rare and have only been examined in the context of C—C bond formation (Z. Li et al., *J. Am. Chem. Soc.,* 2009, 131, 8815-8823; K. W. Quasdorf et al., *J. Am. Chem. Soc.,* 2011, 133, 6352-6363). Accordingly, we conducted a DFT study of the nickel-catalyzed carbamate amination, using N,N-dimethylphenylcarbamate and dimethylamine as substrates (all geometries were optimized using the B3LYP functional and a mixed basis set of SDD for Ni and 6-31G(d) for other atoms. A larger base set, SDD for Ni and 6-311+G(2d,p) for other atoms was used for single point energy calculations and solvation energy corrections using the CPCM model. Single point calculations using the B3P86 and B3PW91 functionals were also performed and give comparable results to the B3LYP calculations. The isopropyl groups on the SIPr ligand were replaced with methyls in the calculations to reduce computational cost. All calculations were performed using Gaussian 09. Gaussian 09, revision B.01, M. J. Frisch et al. Gaussian, Inc., Wallingford Conn., 2010.

Attempts to effect the amination of primary aliphatic amines, such as benzyl amine and n-butylamine, led to the recovery of starting material, albeit with some non-specific decomposition. For a pertinent review, see: L. Xue and Z. Lin, *Chem. Soc. Rev.,* 2010, 39, 1692-1705. For a theoretical study on the Pd-catalyzed amination of bromobenzenes, see: J. N. Harvey, N. Fey and C. L. McMullin, *J. Mol. Catal. A,* 2010, 324, 48-55. For theoretical studies on Pd-mediated reductive elimination, see: V. P. Ananikov et al., *Am. Chem. Soc.,* 2002, 124, 2839-2852; V. P. Ananikov et al., *Organometallics,* 2005, 24, 715-723; E. Zuidema et al., *Organometallics,* 2005, 24, 3703-3710; V. P. Ananikov, D. G. Musaev and K. Morokuma, *Eur. J. Inorg. Chem.,* 2007, 5390-5399; T. E. Barder and S. L. Buchwald, *J. Am. Chem. Soc.,* 2007, 129, 12003-12010; T. Koizumi, A. Yamazaki and T. Yamamoto, *Dalton Trans.,* 2008, 3949-3952; A. Ariafard and B. F. Yates, *J. Organomet. Chem.,* 2009, 694, 2075-2084. For theoretical studies on Pd-mediated reductive elimination, see: V. P. Ananikov et al., *Am. Chem. Soc.,* 2002, 124, 2839-2852; V. P. Ananikov et al., *Organometallics,* 2005, 24, 715-723; E. Zuidema et al., *Organometallics,* 2005, 24, 3703-3710; V. P. Ananikov, D. G. Musaev and K. Morokuma, *Eur. J. Inorg. Chem.,* 2007, 5390-5399; T. E. Barder and S. L. Buchwald, *J. Am. Chem. Soc.,* 2007, 129, 12003-12010; T. Koizumi, A. Yamazaki and T. Yamamoto, *Dalton Trans.,* 2008, 3949-3952; A. Ariafard and B. F. Yates, *J. Organomet. Chem.,* 2009, 694, 2075-2084).

Figure 4:
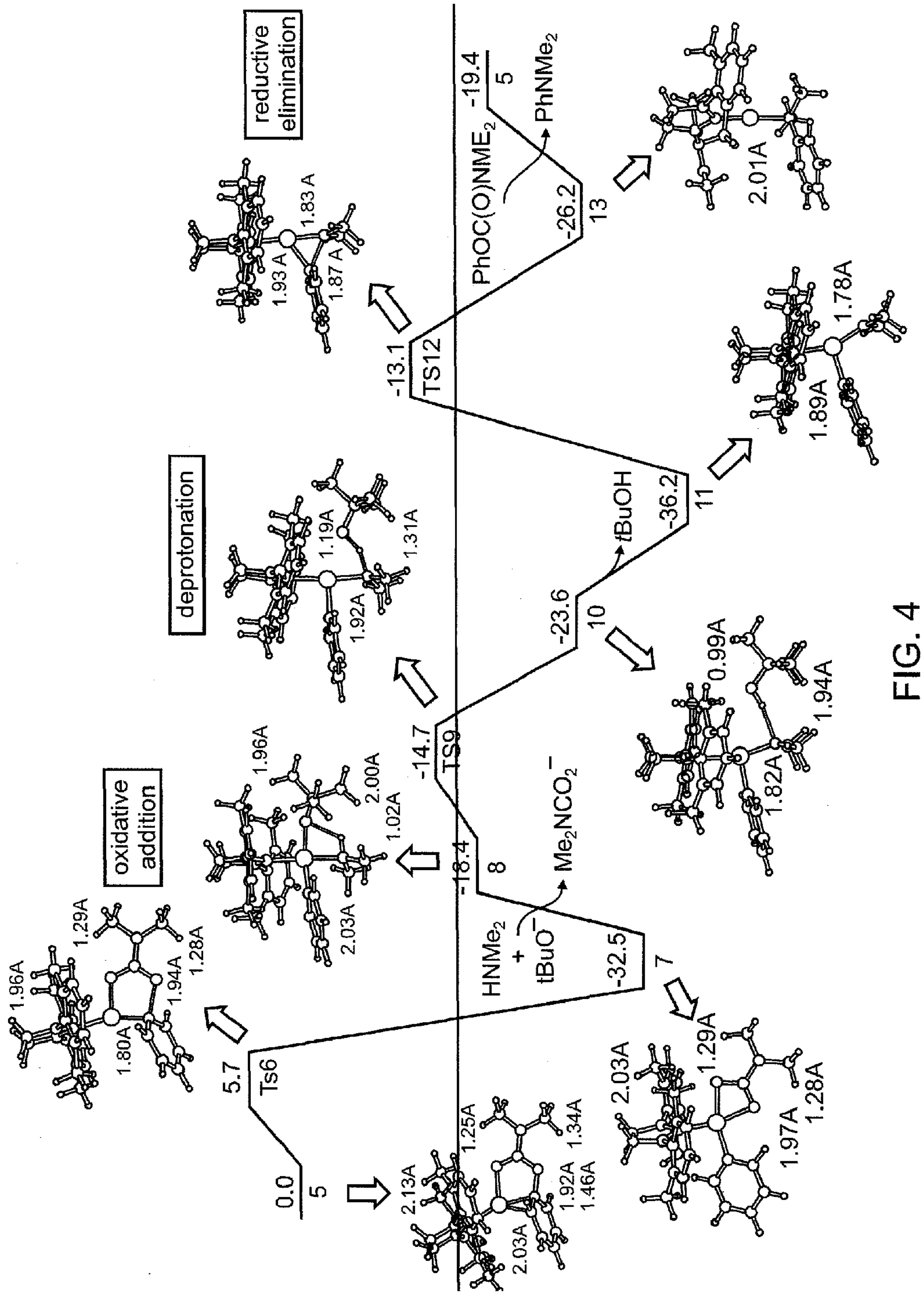
FIG. 4 provides a schematic showing a Gibbs free energy diagram of Ni-catalyzed amination of N,N-dimethylphenylcarbamate and dimethylamine. Energies are given in kcal/mol.

The results of this computational study are shown in FIG. 4 in the form of a Gibbs free energy diagram, which in turn, provides the full catalytic cycle for carbamate amination. Analogous to Pd-catalyzed amination, three fundamental steps occur: oxidative addition, deprotonation, and reductive elimination (Z. Li et al., *J. Am. Chem. Soc.,* 2009, 131, 8815-8823; K. W. Quasdorf et al., *J. Am. Chem. Soc.,* 2011, 133, 6352-6363). Previous mechanistic and theoretical studies on similar Pd- and Ni-catalyzed reactions suggested that the oxidative addition initiates via a monoligated $\eta^2$ complex 5. For a pertinent review, see: L. Xue and Z. Lin, *Chem. Soc. Rev.,* 2010, 39, 1692-1705). For a theoretical study on the Pd-catalyzed amination of bromobenzenes, see: J. N. Harvey, N. Fey and C. L. McMullin, *J. Mol. Catal. A,* 2010, 324, 48-55).

For theoretical studies on Pd-mediated oxidative addition, see: M. Ahlquist et al., 2006, 25, 2066-2073; M. Ahlquist and P. O, Norrby, *Organometallics,* 2007, 26, 550-553; Z. Li, Y. Fu, Q. X. Guo and L. Liu, *Organometallics,* 2008, 27, 4043-4049; J. N. Harvey, N. Fey and J. Jover, *J. Mol. Catal. A,* 2010, 324, 39-47; C. L. McMullin et al., *Dalton Trans.,* 2010, 39, 10833-10836. The mono ligated oxidative addition is suggested as a preferred pathway in most Pd- and Ni-catalyzed oxidative additions with phosphine and NHC ligands: J. P. Stambuli et al., *Angew. Chem. Int. Ed.,* 2002, 41, 4746-4748; J. P. Stambuli et al., *J. Am. Chem. Soc.,* 2002, 124, 9346-9347; J. P. Stambuli, C. D. Incarvito, M. Buehl and J. F. Hartwig, *J. Am. Chem. Soc.,* 2004, 126, 1184-1194; M. Yamashita and J. F. Hartwig, *J. Am. Chem. Soc.,* 2004, 126, 5344-5345; J. C. Green and B. J. Herbert, *J. Organomet. Chem.,* 2005, 690, 6054-6067; L. J. Goossen et al., *Organometallics,* 2006, 25, 54-67; A. G. Sergeev, A. Zapf, A. Spannenberg and M. Beller, *Organometallics,* 2008, 27, 297-300; F. Barrios-Landeros et al., *Am. Chem. Soc.,* 2009, 131, 8141-8154; V. P. W. Böhm et al., *Angew. Chem. Int. Ed.,* 2001, 40, 3387-3389. We calculate that $Ni(NHC)_2$ is 22.6 kcal/mol more stable in solution compared to 5. However, increasing the concentration of the NHC ligand does not suppress the amination reaction, suggesting that $Ni(NHC)_2$ is not the catalyst resting state. Although not presently well-understood, it is likely that the dissociation of one NHC ligand from $Ni(NHC)_2$ is facilitated by other species in the reaction mixture. For similar hypotheses involving NHC dissociation from $Ni(NHC)_2$ complexes, see: P. M. Zimmerman et al., *Chem. Int. Ed.,* 2009, 48, 2201-2205; P. M. Zimmerman et al., *Inorg. Chem.* 2009, 48, 5418-5433). The oxidative addition occurs through a five-centered transition state TS6, in which the carbonyl oxygen in the carbamate is coordinated with Ni (an alternative pathway involving three-centered oxidative addition transition state requires much higher activation energy than the five-centered pathway via TS6. Similar effects are observed in oxidative additions of carbamates and sulfamates with $Ni(PR_3)$). The electron-rich NHC ligand facilitates the oxidative addition, which requires only 5.7 kcal/mol with respect to the $\eta^2$ complex 5 (similar effects of ligands have been reported previously J. P. Corbet and G. Mignani, *Chem. Rev.,* 2006, 106, 2651-2710; M. Ahlquist and P. Norrby, *Organometallics,* 2007, 26, 550-553; N. Marion and S. P. Nolan, *Acc. Chem. Res.,* 2008, 41, 1440-1449; Q. Shen et al., *J. Am. Chem. Soc.,* 2008, 130, 6586-6596). Similar oxidative additions with phosphine ligands require much higher activation energies ($\Delta G^{\ddagger=13.5}$ kcal/mol when $PCy_3$ ligand is used) ((b) K. W. Quasdorf et al., *J. Am. Chem. Soc.,* 2011, 133, 6352-6363).

The oxidative addition leads to a stable intermediate (phenyl)nickel(II) carbamate intermediate 7 (−32.5 kcal/mol). Complex 7 undergoes ligand exchange with dimethylamine and tert-butoxide to liberate carbamate anion and form intermediate 8 (−18.4 kcal/mol). This ligand exchange process is endergonic, mainly due to entropic effects. The proton transfer from the coordinated amine to tert-butoxide (TS9) requires only 3.7 kcal/mol activation energy from complex 8. Since the mechanism involves charged species, the energetics of the deprotonation step is expected to be strongly affected by solvation effects. We have tested a number of DFT methods and basis sets with the CPCM solvation model. These results all indicate that deprotonation is not the rate-limiting step. This also agrees with the experimental observations that the choice of bases does not affect the rate of the reaction. For a related study of effects of bases in Pd-catalyzed aminations, see: S. Shekhar and J. F. Hartwig, *Organometallics,* 2006, 26, 340-351). Subsequent dissociation of tert-butanol gives the (phenyl)(amino) nickel(II) complex 11 (−36.2 kcal/mol). Reductive elimination then occurs through TS12 (−13.1 kcal/mol), which gives the product complex 13 (−26.2 kcal/mol). The reductive elimination from 11 to TS12 requires 23.1 kcal/mol and is the rate-limiting step in the catalytic cycle. Thus, the overall energy span (S. Kozuch and S. Shaik, *Acc. Chem. Res.,* 2011, 44, 101-110) of the catalytic cycle is 23.1 kcal/mol, is in agreement with the experimental observations that the amination reaction readily occurs under slightly elevated temperatures. The barrier for reductive elimination with the Ni(NHC) catalyst is much higher compared to that of Pd-phosphine catalysts. For a theoretical study on the Pd-catalyzed amination of bromobenzenes, see: J. N. Harvey, N. Fey and C. L. McMullin, *J. Mol. Catal. A,* 2010, 324, 48-55; T. E. Barder and S. L. Buchwald, *J. Am. Chem. Soc.,* 2007, 129, 12003-12010. Following the reductive elimination, the reactant complex 5 can be regenerated by ligand exchange from the product complex 13 to initiate another catalytic cycle. The whole catalytic cycle is exergonic by 19.4 kcal/mol. The energy difference (−19.4 kcal/mol) between complex 5 at the beginning and end of the FIG. 4 plot represents the energy released in the catalytic cycle.

Site-Selective Cross-Couplings and Synthetic Applications

Figure 5:
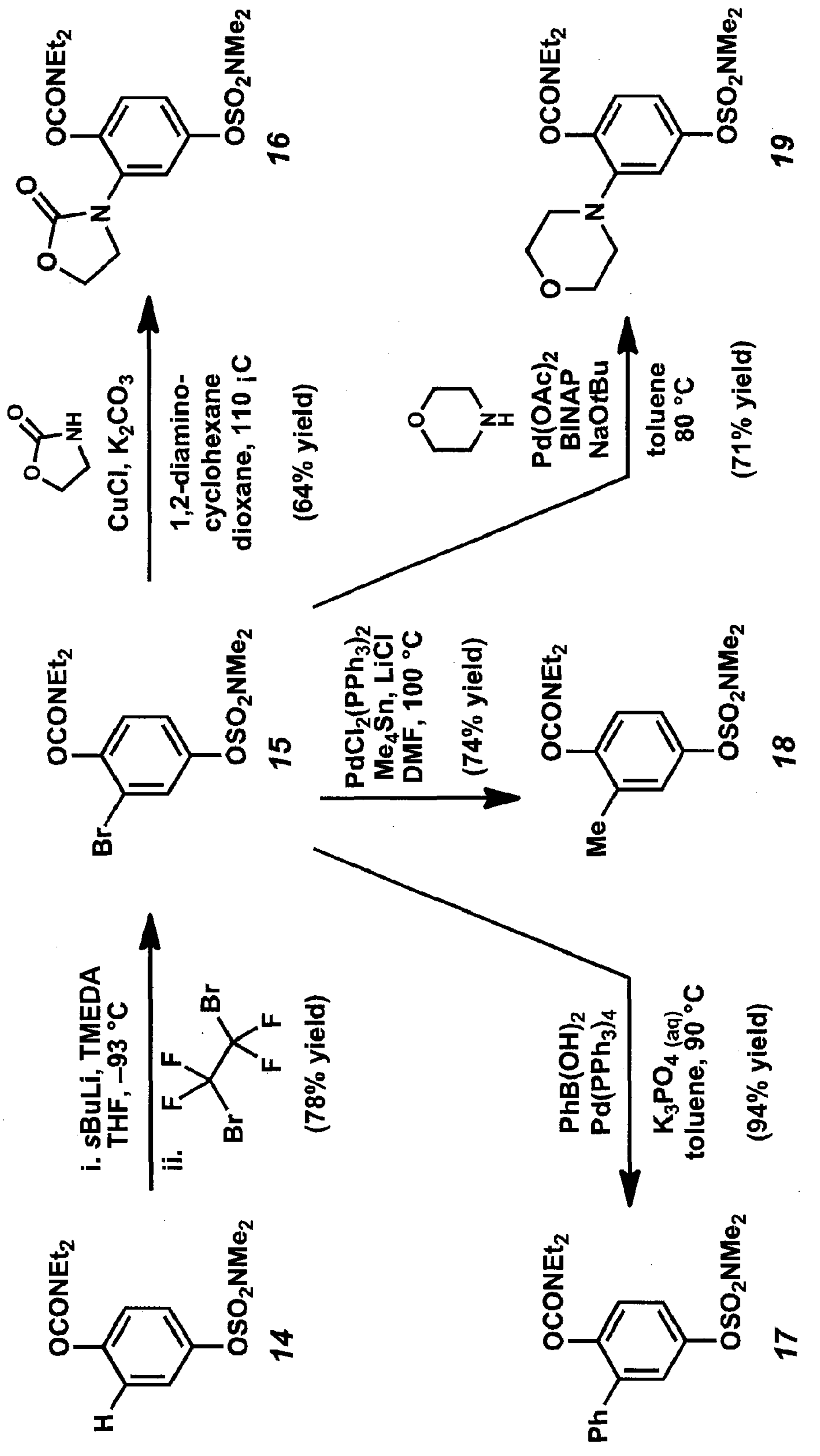
FIG. 5 provides a schematic showing carbamate functionalization and low reactivity of carbamates and sulfamates toward conventional Pd- and Cu-catalyzed couplings.

FIG. 5 highlights a series of experiments that were undertaken to explore carbamate directing group ability and the low reactivity of these substrates to conventional catalytic transformations. The key substrate for our studies, dihydroquinone derivative 14, was selected with the aim of simultaneously probing the reactivity of aryl sulfamates, which have also proven to be extremely useful electrophiles in nickel-catalyzed couplings. Lithiation/bromination of substrate 14 provided trisubstituted arene 15. In accord with literature precedent by Snieckus, the lithiation proceeded selectively adjacent to the carbamate with the sulfamate remaining intact. Bromoarene 15 was subsequently employed in a series of C—C and C-heteroatom bond constructions. Pd-catalyzed arylation (15→17), alkylation (15→18), and amination (15→19) proceeded smoothly, as did Cu-catalyzed C—N bond formation (15→16). In all cases, the sulfamate and carbamate were not disturbed.

Figure 6:
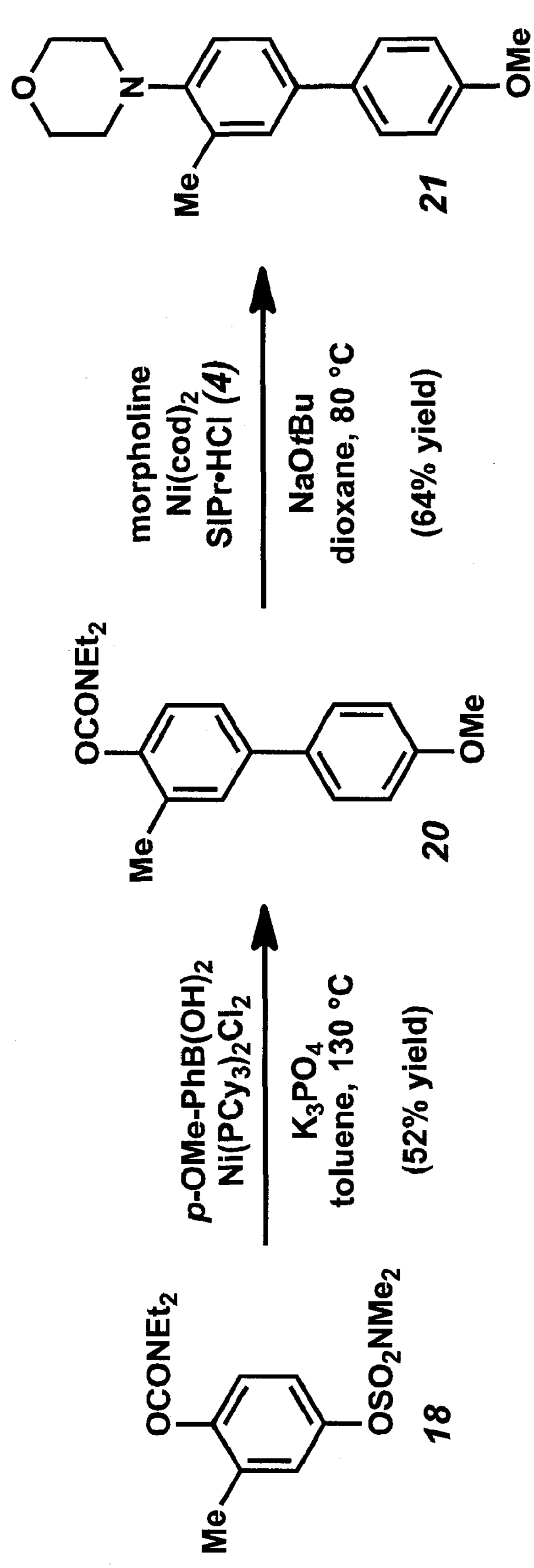
FIG. 6 provides a schematic showing a synthesis of polysubstituted arenes using sequential sulfamate/carbamate couplings.

Having demonstrated the robust nature of carbamates and sulfamates to a variety of conditions, we examined the subsequent cross-couplings of these functional groups (FIG. 6). O-Methylated derivative 18, prepared by either o-bromination/Stille coupling (see FIG. 5) or direct o-methylation of 14, was used in this study. We have found that the sulfamate of 18 is more reactive compared to the carbamate, and that high degrees of selectivity can be obtained in arylation. Competition experiments between phenol-derived carbamates and sulfamates indicate that sulfamates are inherently more reactive than carbamates in both the nickel-catalyzed Suzuki-Miyaura coupling and amination. The preference for sulfamate coupling seen in the conversion of 18→20 is likely heightened because of the carbamate's ortho substituent. Suzuki-Miyaura coupling of 18 furnished carbamate 20 in 52% yield. Subsequently, carbamate 20 was employed in our nickel-catalyzed amination to furnish poly-substituted aryl amine 21. We expect that the ability to consecutively cross-couple bromides, sulfamates, and carbamates will be useful in the synthesis of complex molecules.

Conclusions

In summary, we have found that aryl carbamates are excellent substrates for the nickel-catalyzed amination reaction. The scope of the methodology is broad with respect to both coupling partners, and includes the coupling of electron-rich, heterocyclic, and sterically congested carbamates. DFT calculations reveal the full catalytic cycle of the nickel-catalyzed carbamate amination and suggest that reductive elimination (23.1 kcal/mol barrier) is the rate-determining step. Moreover, we have demonstrated that aryl carbamates are outstanding precursors for the synthesis of polysubstituted aryl amines using sequential carbamate functionalization/site-selective coupling processes. The use of this methodology in natural product synthesis will be reported in due course.

Illustrative Embodiments

A large number of working examples are provides as follows in order to illustrate the versatility and scope of embodiments of the instant invention.

Materials and Methods.

Unless stated otherwise, reactions were conducted in flame-dried glassware under an atmosphere of nitrogen using anhydrous solvents (either freshly distilled or passed through activated alumina columns). Unless otherwise stated, commercially obtained reagents were used as received. Amines were purified by filtration over basic Brockman Grade 158 Å $Al_2O_3$ (Activity 1), followed by distillation over calcium hydride, prior to use. $Ni(cod)_2$ was obtained from Strem Chemicals and SIPr.HCl was obtained from Sigma Aldrich. Dioxane was purified by distillation over sodium benzophenone ketyl radical and degassed by the freeze-pump-thaw method. Reaction temperatures were controlled using an IKAmag temperature modulator, and unless stated otherwise, reactions were performed at room temperature (rt, approximately 23° C.). Thin-layer chromatography (TLC) was conducted with EMD gel 60 F254 pre-coated plates (0.25 mm) and visualized using a combination of UV, anisaldehyde, ceric ammonium molybdate, iodine, vanillin, and potassium permanganate staining Silicycle Siliaflash P60 (particle size 0.040-0.063 mm) was used for flash column chromatography. $^1H$ NMR spectra were recorded on Bruker spectrometers (at 300, 400, 500, 600 MHz) and are reported relative to deuterated solvent signals. Data for $^1H$ NMR spectra are reported as follows: chemical shift (δ ppm), multiplicity, coupling constant (Hz) and integration. $^{13}C$ NMR spectra were recorded on Bruker Spectrometers (at 125 MHz). Data for $^{13}C$ NMR spectra are reported in terms of chemical shift. $^{19}F$ NMR (at 300, 400 MHz) spectra are reported in terms of chemical shift. IR spectra were recorded on a Perkin-Elmer 100 spectrometer and are reported in terms of frequency of absorption ($cm^{-1}$). Melting points are uncorrected and were obtained on a Laboratory Devices Mel-Temp II instrument. High resolution mass spectra were obtained from the UC Irvine Mass Spectrometry Facility.

Illustrative Experimental Procedures.

Please note that the "SI" designations that follow are specific to Example 2.

A. Synthesis of Aryl Carbamate Substrates

Note: information for the synthesis of the aryl carbamates shown in Tables 3-5 have previously been reported (see, e.g. Yamazaki et al., *M. Org. Lett.* 2010, 12, 3978-3981; Quasdorf et al., *J. Am. Chem. Soc.* 2009, 131, 17748-17749; Sengupta et al., *J. Org. Chem.* 1992, 57, 4066-4068; Zhao, Z.; Snieckus, V. *Org. Lett.* 2005, 7, 2523-2526; Kamila et al., *Tetrahedron* 2003, 59 1339-1348; Bedford et al., *J. Org. Biomol. Chem.* 2009, 7, 4853-4857; Azzena et al., *Appl. Organolmetal. Chem.* 2008, 22, 523-528) with the exception of the carbamate SI-2, carbamate SI-4, and carbamate SI-6.

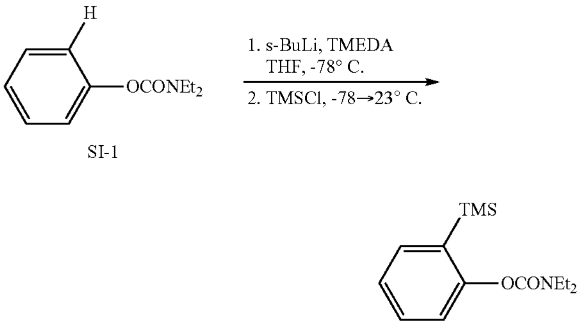

SI-1

SI-2

SI-2 (Table 4, Entry 3).

To the phenyl carbamate (SI-1) (1.0 g, 4.82 mmol, 1 equiv) in THF (24 mL) was added TMEDA (0.79 mL, 5.31 mmol, 1.1 equiv) at 0° C. The solution was cooled to −78° C. and s-BuLi (1.04 M in Hexanes, 5.11 mL, 5.31 mmol, 1.1 equiv) was added over 15 min. The mixture was stirred at −78° C. for 1 h and then TMSCl (0.80 ml, 6.3 mmol, 1.3 equiv) was added over 10 min. The resulting mixture was stirred at −78° C. for 45 min and then allowed to warm to 23° C. The reaction was quenched with saturated aqueous $NH_4Cl$ (10 mL). The layers were separated and the aqueous layer was extracted with $Et_2O$ (5×25 mL). The combined organic layers were washed with brine (10 mL), dried over $MgSO_4$, and then evaporated to dryness. The crude residue was purified by flash chromatography (5:1 Hexanes:EtOAc) to furnish 2-(trimethylsilyl)phenyl carbamate SI-2 as a colorless solid (1.17 g, 85% yield). $R_f$ 0.41 (5:1 Hexanes: EtOAc); $^1H$ NMR (400 MHz, $CDCl_3$): δ 7.46 (dd, J=7.5, 1.5 Hz, 1H), 7.37 (ddd, J=7.5, 1.5, 1.0 Hz, 1H), 7.18 (td, J=7.0, 1.0 Hz, 1H), 7.04 (dd, J=8.0, 0.5 Hz, 1H), 3.49 (q, J=7.5 Hz, 2H), 3.49 (q, J=7.5 Hz, 2H), 3.40 (q, J=7.5 Hz, 2H), 1.26 (t, J=7.5 Hz, 3H), 1.20 (t, J=7.5 Hz, 3H), 0.29 (s, 9H); $^{13}C$NMR (125 MHz, $CDCl_3$): δ 156.5, 154.6, 135.0, 131.7, 130.5, 124.9, 122.4, 42.1, 41.7, 14.3, 13.4, −0.7; IR (film): 2972, 1714, 1412, 1258, 1152 $cm^{-1}$; HRMS-ESI (m/z) $[M+Na]^+$ calcd for $C_{14}H_{23}NO_2SiNa$, 288.1396. found, 288.1393.

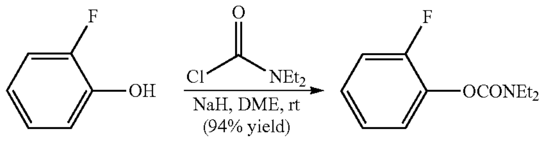

SI-3 SI-4

SI-4 (Table 4, Entry 5).

A round bottom flask was charged with NaH (0.85 g, 21.4 mmol, 1.2 equiv, 60% dispersion in oil). A solution of 2-fluorophenol (SI-3) (2.0 g, 17.8 mmol, 1 equiv) in DME (71 mL) was added dropwise via cannula to the NaH. A solution of diethylcarbamoyl chloride (2.15 mL, 16.9 mmol, 0.95 equiv) in DME (10 mL) was then added dropwise via cannula to the reaction vessel. The reaction was allowed to stir for 15 h and then quenched with $H_2O$ (10 mL). The volatiles were removed under reduced pressure, and then $Et_2O$ (50 mL) and $H_2O$ (20 mL) were added. The layers were separated, and the organic layer was washed successively with 1 M KOH (20 mL) and $H_2O$ (20 mL). The combined aqueous layers were extracted with $Et_2O$ (3×25 mL). The combined organic layers were then washed with brine (10 mL), dried over $MgSO_4$, and concentrated under reduced pressure. The crude residue was purified by flash chromatography (5:1 Hexanes:EtOAc) to yield 2-fluorophenylsulfamate SI-4 as a clear oil (3.35 g, 94% yield). $R_f$ 0.27 (5:1 Hexanes:EtOAc); $^1H$ NMR (500 MHz, $CDCl_3$): δ 7.21-7.09 (m, 4H), 3.46 (q, J=6.5, 2H), 3.39 (q, J=6.5, 2H), 1.27 (t, J=6.5, 3H) 1.21 (t, J=7.0, 3H); $^{13}C$ NMR (125 MHz, $CDCl_3$): δ 154.6 (d, J=246.5), 153.2, 139.0 (d, J=12.1), 126.2 (d, J=7.0), 124.2, 124.1 (d, J=3.9), 116.3 (d, J=18.4), 42.4, 42.0, 13.9, 13.2; IR (film): 2977, 1720, 1600, 1502, 1417, 1255 $cm^{-1}$; HRMS-ESI (m/z) $[M+Na]^+$ calcd for $C_{11}H_{14}FNO_2Na$, 234.0906. found, 234.0912.

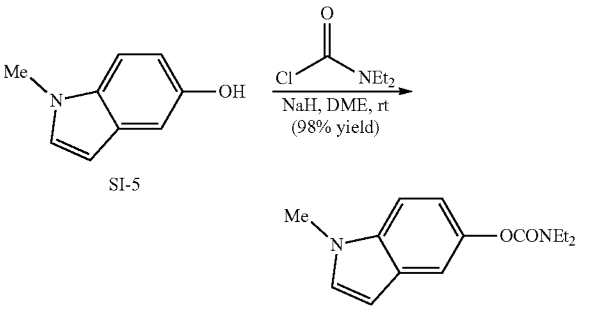

SI-5

SI-6

SI-6 (Table 4, Entry 6).

A round bottom flask was charged with NaH (0.33 g, 8.15 mmol, 1.2 equiv, 60% dispersion in oil). A solution of N-methyl-5-hydroxyindole (SI-5) (1.0 g, 6.79 mmol, 1 equiv) in DME (27 mL) was added dropwise via cannula to the NaH. A solution of diethylcarbamoyl chloride (0.875 mL, 6.45 mmol, 0.95 equiv) in DME (15 mL) was then added dropwise via cannula to the reaction vessel. The reaction was allowed to stir for 3.5 d, and then quenched with $H_2O$ (10 mL). The volatiles were removed under reduced pressure, and then $Et_2O$ (50 mL) and $H_2O$ (15 mL) were added. The layers were separated, and the organic layer was washed successively with 1 M KOH (20 mL) and $H_2O$ (20 mL). The combined aqueous layers were extracted with $Et_2O$ (3×20 mL). The combined organic layers were then washed with brine (20 mL), dried over $MgSO_4$, and concentrated under reduced pressure. The crude residue was purified by flash chromatography (9:1 Benzene:$Et_2O$) to yield N-methylindole-5-carbamate SI-6 as a white solid (1.55 g, 98% yield). $R_f$ 0.44 (9:1 Benzene:$Et_2O$); $^1H$ NMR (500 MHz, $CDCl_3$): δ 7.33 (d, J=2.5, 1H), 7.26 (d, J=9.0, 1H), 7.05 (d, J=3.0, 1H), 6.98 (dd, J=8.5, 2.3, 1H), 6.43 (dd, J=3.0, 0.5, 1H), 3.78 (s, 3H), 3.47 (bs, 2H), 3.41 (bs, 2H), 1.27 (bs, 3H), 1.21 (bs, 3H); $^{13}C$ NMR (125 MHz, $CDCl_3$): δ 155.4, 145.1, 134.5, 129.8, 128.7, 116.3, 113.2, 109.4, 101.1, 42.3, 41.9, 33.1, 14.4, 13.6; IR (film): 2972, 1708, 1467, 1418, 1218, 1159 $cm^{-1}$; HRMS-ESI (m/z) $[M+Na]^+$ calcd for $C_{14}H_{18}N_2O_2Na$, 269.1266. found, 269.1267.

B. Aminations of Aryl Carbamates

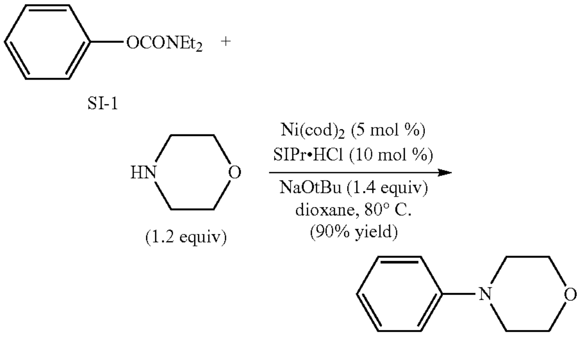

SI-1

SI-7

Representative Procedure (Coupling of Phenylcarbamate SI-1, Table 3, Entry 3) is Used as an Example). SI-7.

A 20 mL reaction vial was charged with $Ni(cod)_2$ (6.8 mg, 0.025 mmol, 5 mol %), SIPr.HCl (21.2 mg, 0.05 mmol, 10 mol %), anhydrous powdered NaOtBu (67.2 mg, 0.7 mmol, 1.4 equiv), and a magnetic stir bar, all in a glove box. Subsequently, a solution of carbamate substrate SI-1 (96.6 mg, 0.50 mmol, 1 equiv) and morpholine (52.4 μL, 0.60 mmol, 1.2 equiv) in dioxane (2.5 mL) was added. The vessel was removed from the glove box, and then heated to 80° C. for 3 h. After cooling the reaction vessel to 23° C. and concentrating under reduced pressure, the crude residue was loaded onto a silica gel column (2.5×10 cm) and purified by flash chromatography (9:1 Hexanes:EtOAc) to yield aminated product SI-7 (73.4 mg, 90% yield) as a white solid. $R_f$ 0.29 (9:1 Hexanes:EtOAc). Spectral data match those previously reported (Barker, T. J.; Jarvo, E. R. *J. Am. Chem. Soc.* 2009, 131, 15598-15599).

Any modifications of the conditions shown in this representative procedure are specified in the following schemes, which depict all of the results shown in Tables 3, 4, and 5.

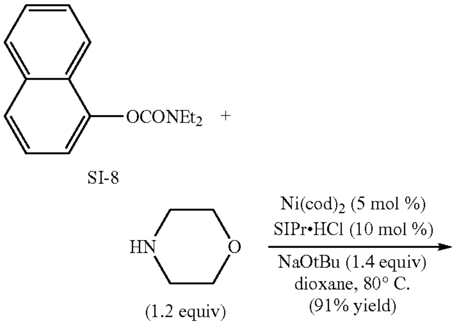

SI-8

-continued

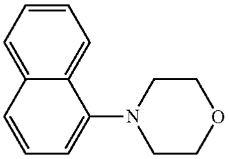

SI-9

SI-9 (Table 3, Entry 1).

Purification by flash chromatography (9:1 Hexanes:EtOAc) afforded aminated product SI-9 (91% yield) as a white solid. $R_f$ 0.38 (9:1 Hexanes:EtOAc). Spectral data match those previously reported (Desmarets, C.; Champagne, B.; Walcarius, A.; Bellouard, C.; Omar-Amrani, R.; Ahajji, A.; Fort, Y.; Schneider, R. *J. Org. Chem.* 2006, 71, 1351-1361).

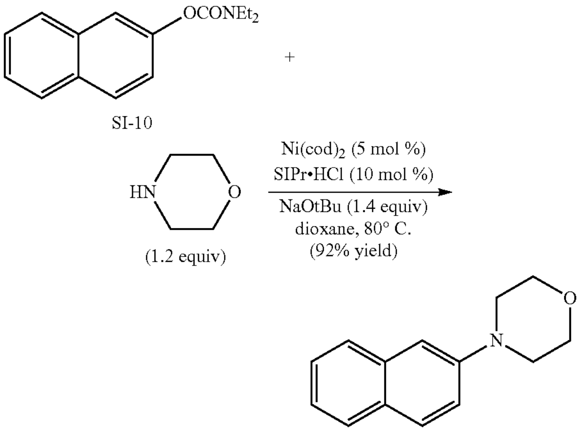

SI-10

SI-11

SI-11 (Table 3, Entry 2).

Purification by flash chromatography (9:1 Hexanes:EtOAc) afforded aminated product SI-11 (92% yield) as a white solid. $R_f$ 0.32 (9:1 Hexanes:EtOAc). Spectral data match those previously reported (Gao, C.; Yang, L. *J. Org. Chem.* 2008, 73, 1624-1627).

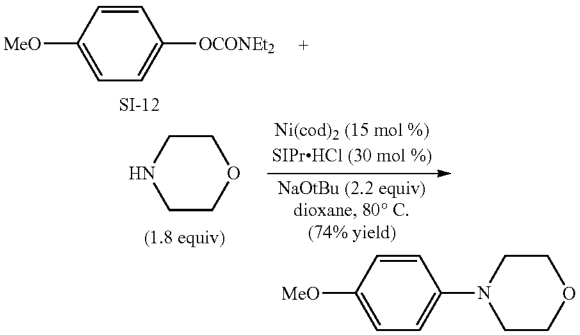

SI-12

SI-13

SI-13 (Table 3, Entry 4).

Purification by flash chromatography (10:1:1 Benzene:$Et_2O$:$CH_2Cl_2$) afforded aminated product SI-13 (74% yield) as a white solid. $R_f$ 0.18 (10:1:1 Benzene:$Et_2O$:$CH_2Cl_2$). Spectral data match those previously reported (Wolfe, J. P.; Buchwald, S. L. *J. Org. Chem.* 1996, 61, 1133-1135).

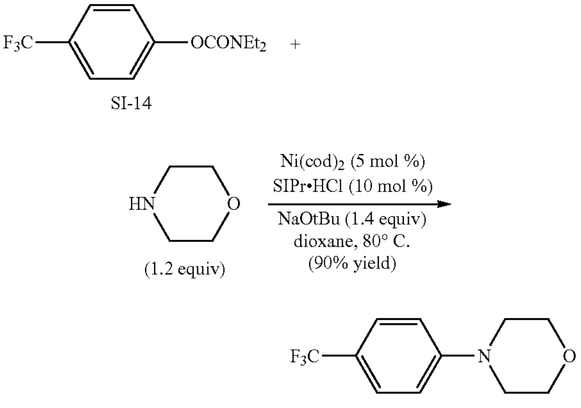

SI-14

SI-15

SI-15 (Table 3, Entry 5).

Purification by flash chromatography (30:1 Benzene:$Et_2O$) afforded aminated product SI-15 (90% yield) as a white solid. $R_f$ 0.30 (30:1 Benzene:$Et_2O$). Spectral data match those previously reported (Guo, D.; Huang, H.; Xu, J.; Jiang, H.; Liu, H. *Org. Lett.* 2008, 10, 4513-4516).

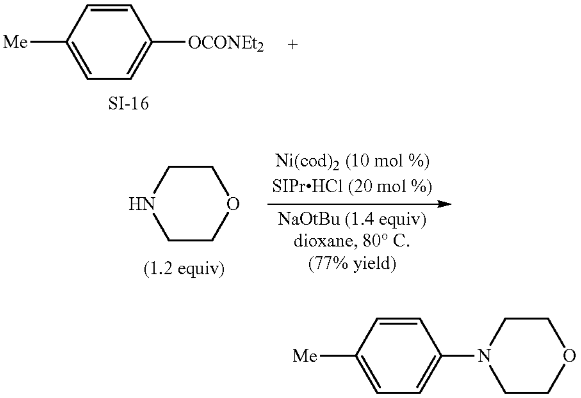

SI-16

SI-17

SI-17 (Table 3, Entry 6).

Purification by flash chromatography (19:1 Benzene:$Et_2O$) afforded aminated product SI-17 (77% yield) as a white solid. $R_f$ 0.53 (19:1 Benzene:$Et_2O$). Spectral data match those previously reported (Desmarets, C.; Schneider, R.; Fort, Y. *J. Org. Chem.* 2002, 67, 3029-3036).

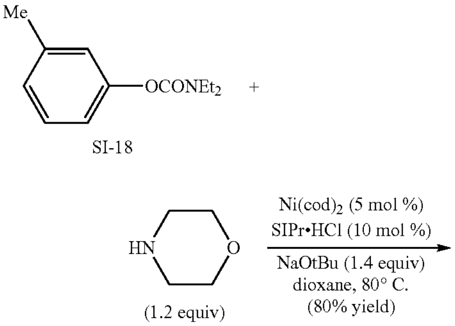

SI-18

-continued

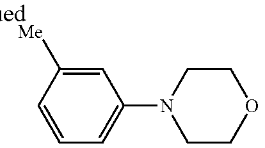

SI-19

SI-19 (Table 3, Entry 7).

Purification by flash chromatography (19:1 Benzene: $Et_2O$) afforded aminated product SI-19 (80% yield) as a yellow oil. $R_f$ 0.49 (19:1 Benzene:$Et_2O$). Spectral data match those previously reported (Desmarets, C.; Schneider, R.; Fort, Y. *J. Org. Chem.* 2002, 67, 3029-3036).

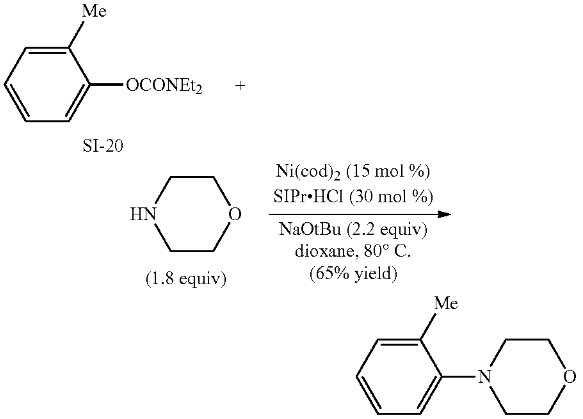

SI-20

SI-21

SI-21 (Table 4, Entry 1).

Purification by flash chromatography (19:1 Hexanes:EtOAc) afforded aminated product SI-21 (65% yield) as a yellow oil. $R_f$ 0.37 (19:1 Hexanes:EtOAc). Spectral data match those previously reported (Desmarets, C.; Schneider, R.; Fort, Y. *J. Org. Chem.* 2002, 67, 3029-3036).

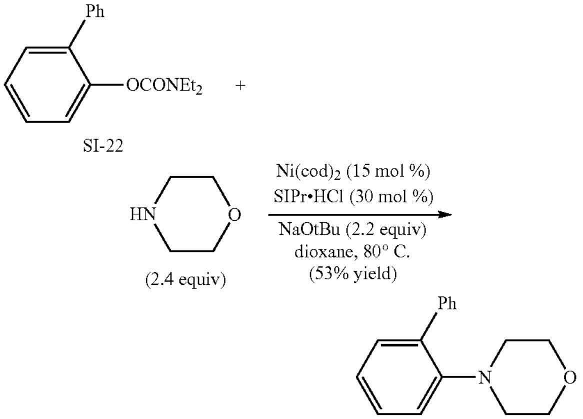

SI-22

SI-23

SI-23 (Table 4, Entry 2).

Purification by flash chromatography (100% Benzene) afforded aminated product SI-23 (53% yield) as an off-white solid. $R_f$ 0.53 (100% Benzene); $^1H$ NMR (500 MHz, $CDCl_3$): δ 7.66 (dd, J=8.2, 1.2, 2H), 7.42 (t, J=7.6, 2H), 7.35-7.30 (m, 2H), 7.28 (dd, J=7.6, 1.6, 1H), 7.12 (td, J=7.5, 1.1, 1H), 7.05 (dd, J=8.1, 0.8, 1H), 3.62 (t, J=4.6, 4H), 2.84 (t, J=4.6, 4H); $^{13}C$ NMR (125 MHz, $CDCl_3$): δ 150.1, 141.1, 135.1, 131.7, 128.9, 128.5, 128.3, 127.0, 123.0, 118.1, 67.1, 51.6; IR (film): 2950, 2815, 1593, 1480, 1439, 1221, 1110 $cm^{-1}$; HRMS-ESI (m/z) $[M+H]^+$ calcd for $C_{16}H_{17}NOH$, 240.1388. found, 240.1394.

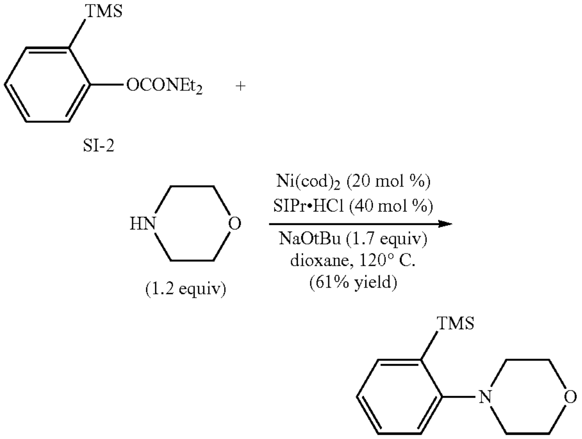

SI-2

SI-24

SI-24 (Table 4, Entry 3).

Purification by flash chromatography (5:1 Benzene: Hexanes) afforded aminated product SI-24 (61% yield) as a white solid. $R_f$ 0.31 (100% Benzene); $^1H$ NMR (500 MHz, $CDCl_3$): δ 7.50 (d, J=7.3, 1H), 7.41 (t, J=7.1, 1H), 7.33 (d, J=7.9, 1H), 7.22 (t, J=7.2, 1H), 3.85 (t, J=4.3, 4H), 2.89 (bs, 4H), 0.31 (s, 9H); $^{13}C$ NMR (125 MHz, $CDCl_3$): δ 159.5, 138.8, 135.6, 130.5, 125.9, 122.8, 67.4, 54.5, 0.2; IR (film): 2852, 1583, 1473, 1258, 1109 $cm^{-1}$; HRMS-ESI (m/z) $[M+H]^+$ calcd for $C_{13}H_{21}NOSiH$, 236.1471. found, 236.1466.

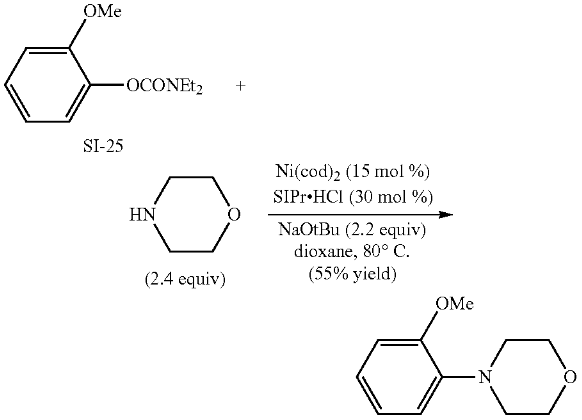

SI-25

SI-26

SI-26 (Table 4, Entry 4).

Purification by flash chromatography (9:1 Benzene:$Et_2O$) afforded aminated product SI-26 (55% yield) as a yellow oil. $R_f$ 0.23 (9:1 Benzene:$Et_2O$). Spectral data match those previously reported (Li, J.; Cui, M.; Yu, A.; Wu, Y. *J. Organomet. Chem.* 2007, 692, 3732-3742).

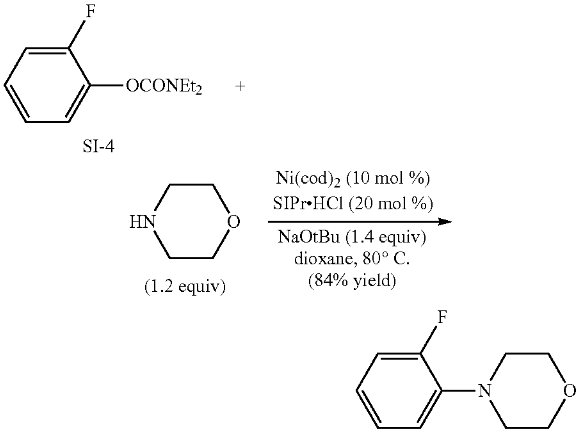

SI-4

SI-27

SI-27 (Table 4, Entry 5).

Purification by flash chromatography (40:1 Benzene: $Et_2O$) afforded aminated product SI-27 (84% yield) as an off-white solid. $R_f$ 0.22 (40:1 Benzene:$Et_2O$). Spectral data match those previously reported (Fasani, E.; Tilocca, F.; Protti, S.; Merli, D.; Albini, A. Org. Biomol. Chem. 2008, 6, 4634-4642).

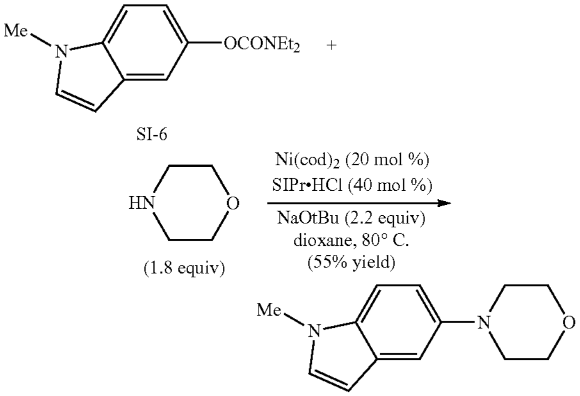

SI-6

SI-28

SI-28 (Table 4, Entry 6).

Purification by flash chromatography (6:1:1 Benzene: $Et_2O$:$CH_2Cl_2$) afforded aminated product SI-28 (55% yield) as a off-white solid. $R_f$ 0.21 (10:1:1 Benzene:$Et_2O$:$CH_2Cl_2$); $^1$H NMR (500 MHz, $CDCl_3$): δ 7.25 (d, J=8.8, 1H), 7.16 (d, J=2.2, 1H), 7.03-6.97 (m, 2H), 6.41 (d, J=3.0, 1H), 3.91 (t, J=4.7, 4H), 3.76 (s, 3H), 3.13 (t, J=4.7, 4H); $^{13}$C NMR (125 MHz, $CDCl_3$): δ 145.9, 132.9, 129.5, 129.2, 115.2, 110.1, 108.0, 100.8, 67.6, 52.4, 33.2; IR (film): 3093, 2968, 1616, 1490, 1231, 1115 $cm^{-1}$; HRMS-ESI (m/z) $[M+H]^+$ calcd for $C_{13}H_{16}N_2OH$, 217.1341. found, 217.1342.

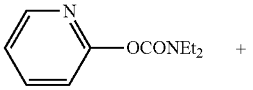

SI-29

-continued

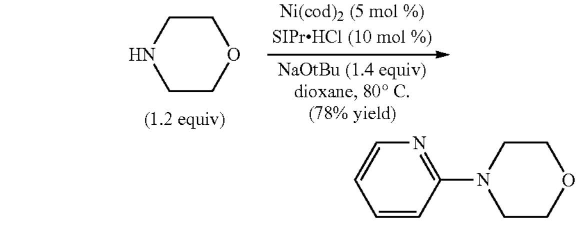

SI-30

SI-30 (Table 4, Entry 7).

Purification by flash chromatography (2:1 Hexanes:EtOAc) afforded aminated product SI-30 (78% yield) as a pale yellow oil. $R_f$ 0.28 (9:1 Benzene:$Et_2O$). Spectral data match those previously reported (Wagaw, S.; Buchwald, S. L. *J. Org. Chem.* 1996, 61, 7240-7241).

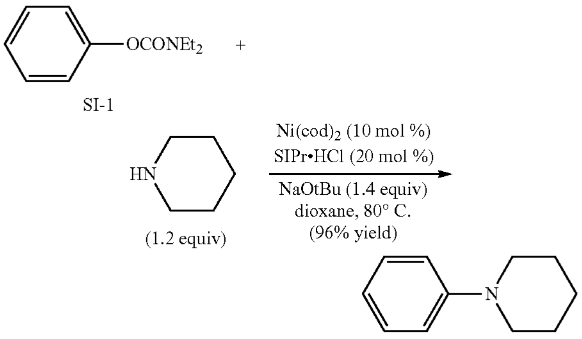

SI-1

SI-31

SI-31 (Table 5, Entry 1).

Purification by flash chromatography (50:1 Hexanes:EtOAc) afforded aminated product SI-31 (96% yield) as a clear oil. $R_f$ 0.29 (50:1 Hexanes:EtOAc). Spectral data match those previously reported (Shimasaki, T.; Tobisu, M.; Chatani, N. *Angew. Chem. Int. Ed.* 2010, 49, 2929-2932).

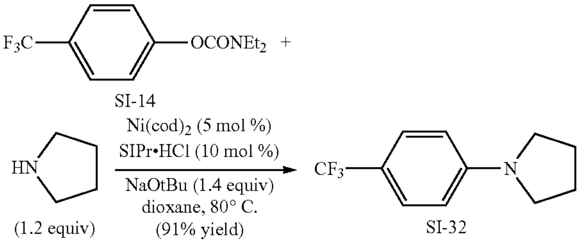

SI-14

SI-32

SI-32 (Table 5, Entry 2).

Purification by flash chromatography (50:1 Hexanes: $Et_2O$) afforded aminated product SI-32 (91% yield) as a white solid. $R_f$ 0.28 (50:1 Hexanes:$Et_2O$). Spectral data match those previously reported (Brenner, E.; Schneider, R.; Fort, Y. *Tetrahedron* 1999, 55, 12829-12842).

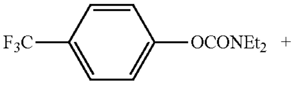

SI-14

-continued

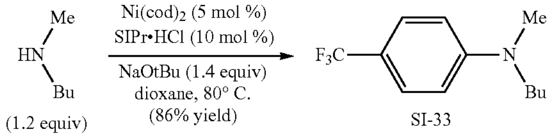

SI-33

SI-33 (Table 5, Entry 3).

Purification by flash chromatography (50:1 Hexanes: $Et_2O$) afforded aminated product SI-33 (86% yield) as a clear oil. $R_f$ 0.32 (50:1 Hexanes:$Et_2O$); $^1$H NMR (300 MHz, $CDCl_3$): δ 7.42 (d, J=9.0, 2H), 6.66 (d, J=8.7, 2H), 3.35 (t, J=7.3, 2H), 2.97 (s, 3H), 1.62-1.52 (m, 2H), 1.35 (sextet, J=7.2, 2H), 0.95 (t, J=7.4, 3H), $^{13}$C NMR (125 MHz, $CDCl_3$): δ 151.4, 126.6 (q, J=3.8), 125.4 (q, J=268.3), 117.0 (q, J=32.0), 110.9, 52.9, 38.4, 28.9, 20.4, 14.0; $^{19}$F NMR (300 MHz, $CDCl_3$): δ -60.8; IR (film): 2960, 2933, 2876, 1616, 1533, 1322, 1197, 1100, 1068 $cm^{-1}$; HRMS-ESI (m/z) $[M+H]^+$ calcd for $C_{12}H_{16}F_3H$, 232.1313. found 232.1307.

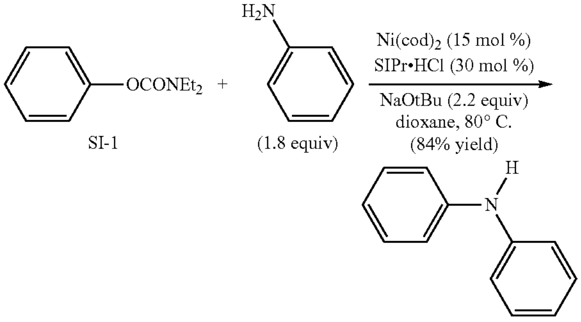

SI-34

SI-34 (Table 5, Entry 4).

Purification by flash chromatography (4:1 Hexanes: $CH_2Cl_2$) afforded aminated product SI-34 (84% yield) as a yellow solid. $R_f$ 0.28 (4:1 Hexanes:$CH_2Cl_2$). Spectral data match those previously reported (Desmarets, C.; Schneider, R.; Fort, Y. *J. Org. Chem.* 2002, 67, 3029-3036).

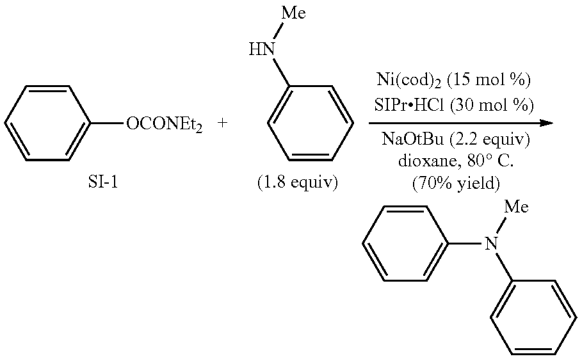

SI-35

SI-35 (Table 5, Entry 5).

Purification by flash chromatography (100:1 Hexanes: $Et_2O$) afforded aminated product SI-35 (70% yield) as a yellow oil. $R_f$ 0.12 (100:1 Hexanes:$Et_2O$). Spectral data match those previously reported (Desmarets, C.; Schneider, R.; Fort, Y. *J. Org. Chem.* 2002, 67, 3029-3036).

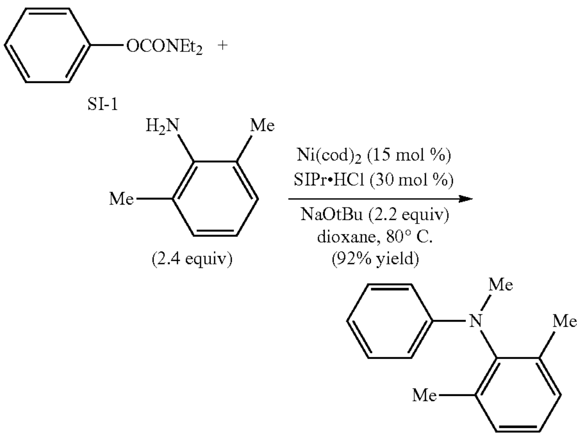

SI-36

SI-36 (Table 5, Entry 6).

Purification by flash chromatography (20:1 Hexanes: $Et_2O$) afforded aminated product SI-36 (92% yield) as a clear oil. $R_f$ 0.41 (20:1 Hexanes:$Et_2O$). Spectral data match those previously reported (Desmarets, C.; Schneider, R.; Fort, Y. *J. Org. Chem.* 2002, 67, 3029-3036).

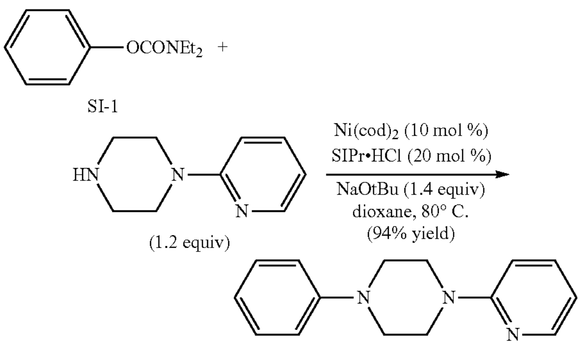

SI-37

SI-37 (Table 5, Entry 7).

Purification by flash chromatography (8:1 Hexanes:EtOAc) afforded aminated product SI-37 (94% yield) as a white solid. $R_f$ 0.30 (8:1 Hexanes:EtOAc). Spectral data match those previously reported (Shimasaki, T.; Tobisu, M.; Chatani, N. *Angew. Chem. Int. Ed.* 2010, 49, 2929-2932).

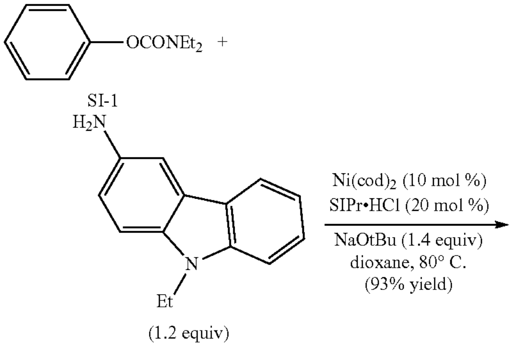

-continued

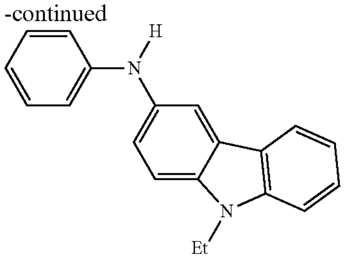

SI-38

SI-38 (Table 5, Entry 8).

Purification by flash chromatography (300:150:1 Hexanes:$CH_2Cl_2$:$Et_3N$) afforded aminated product SI-38 (93% yield) as a white solid. $R_f$ 0.30 (2:1 Hexanes:$CH_2Cl_2$); $^1$HNMR (500 MHz, $C_6D_6$): δ 7.94 (d, J=6.7, 1H), 7.74 (d, J=1.7, 1H), 7.39 (t, J=7.6, 1H), 7.21-7.16 (m, 4H), 7.07 (d, J=8.2, 1H), 6.95 (d, J=8.5, 1H), 6.91 (d, J=8.4, 2H), 6.82, (td, J=7.4, 0.8, 1H), 5.15 (s, 1H), 3.69 (q, J=7.2, 2H), 0.92 (t, J=7.3, 3H); $^{13}$C NMR (125 MHz, $C_6D_6$): δ 147.0, 140.9, 137.0, 134.9, 129.7, 126.0, 124.2, 123.3, 121.9, 121.0, 119.4, 119.1, 115.6, 114.4, 109.2, 108.8, 37.4, 13.6; IR (film): 3383, 3048, 2974, 1598, 1504, 1489, 1470, 1299, 1229, 1150 $cm^{-1}$; HRMS-ESI (m/z) $[M+H]^+$ calcd for $C_{20}H_{18}N_2H$, 287.1548. found 287.1551.

C. Experiments Involving Carbamate and Sulfamate Substrates

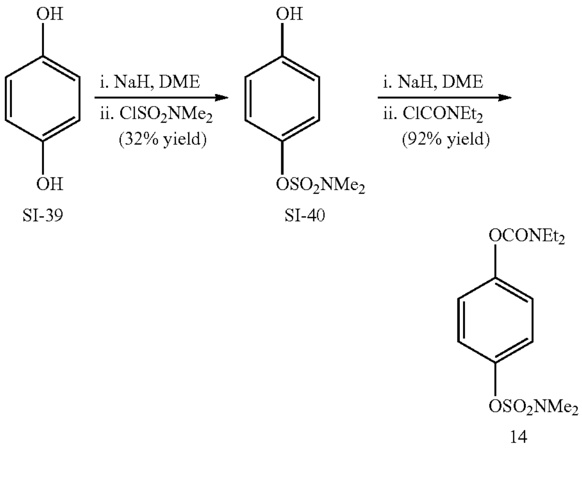

SI-39 SI-40 14

Carbamate Sulfamate 14.

To a charged round bottom flask was added NaH (0.308 g, 25.9 mmol, 1.2 equiv, 60% dispersion in oil). A solution of hydroquinone (SI-39) (3.0 g, 27.3 mmol, 1 equiv) in DME (60 mL) was added dropwise via cannula to the NaH. A solution of dimethylsulfamoyl chloride (2.76 mL, 25.9 mmol, 1.2 equiv) in DME (60 mL) was then added immediately via three cannulae to the reaction vessel. The reaction was allowed to stir for 12 h and the reaction was quenched with deionized $H_2O$ (20 mL). The volatiles were removed under reduced pressure, and then $Et_2O$ (50 mL) and $H_2O$ (20 mL) were added. The layers were separated and the organic phase was washed with $H_2O$ (3×30 mL). The combined aqueous layers were extracted with $Et_2O$ (3×50 mL). The combined organic layers were then washed with brine (20 mL), dried over $MgSO_4$, and concentrated under reduced pressure. The crude residue was purified by flash chromatography (7:1:1 Benzene:$CH_2Cl_2$:$Et_2O$) to yield sulfamate phenol SI-40 as a white solid (1.77 g, 32% yield).

A round bottom flask was charged with NaH (0.560 g, 14.0 mmol, 1.2 equiv, 60% dispersion in oil). A solution of the sulfamate phenol (SI-40) (2.53 g, 11.7 mmol, 1 equiv) in DME (23 mL) was added dropwise to the NaH. A solution of diethylcarbamoyl chloride (1.45 mL, 11.0 mmol, 0.95 equiv) in DME (23 mL) was then added dropwise to the reaction vessel. The reaction was allowed to stir for 12 h and the reaction was quenched with deionized $H_2O$ (9 mL). The solvent was removed under reduced pressure and then $Et_2O$ (22 mL) was added. The organic layer was washed with $H_2O$ (3×9 mL). The combined aqueous layers were extracted with $Et_2O$ (3×22 mL). The combined organic layers were washed with brine (9 mL), dried over $MgSO_4$, and concentrated under reduced pressure. The crude residue was purified by flash chromatography (1:1 Hexanes:EtOAc) to yield carbamate sulfamate 14 as a white solid (3.39 g, 92% yield). $R_f$ 0.54 (7:1:1 Benzene:$Et_2O$:$CH_2Cl_2$); $^1$H NMR (500 MHz, $CDCl_3$): δ 7.27 (d, J=8.5, 2H), 7.14 (d, J=9, 2H), 3.41 (m, 4H), 2.69 (s, 6H), 1.25 (t, J=7, 3H), 1.20 (t, J=7, 3H); $^{13}$C NMR (125 MHz, $CDCl_3$): δ 153.9, 149.9, 147.1, 123.1, 122.7, 42.5, 42.1, 38.9, 14.4, 13.5; IR (film): 2983, 2939, 1721, 1474, 1357, 1273, 1156 $cm^{-1}$; HRMS-ESI (m/z) $[M+Na]^+$ calcd for $C_{13}H_{20}N_2O_5SNa$, 339.0991. found 339.0988.

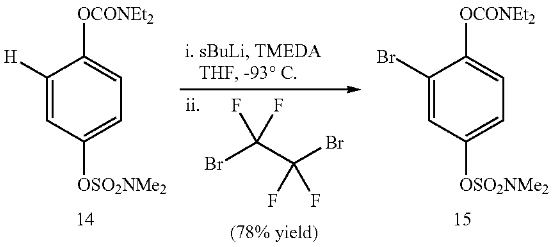

14 15

Bromide 15.

To a solution of carbamate 14 (280.7 mg, 0.887 mmol, 1.0 equiv) and TMEDA (0.145 mL, 0.976 mmol, 1.1 equiv) in THF (4.4 mL) at −93° C. was added s-BuLi (0.720 mL, 0.976 mmol, 1.1 equiv) dropwise. After stirring for 45 min, 1,2-dibromotetrafluoroethane (0.148 mL, 1.242 mmol, 1.4 equiv) was added dropwise. The reaction was allowed to warm to 23° C. over 15 min, and then quenched with saturated aqueous $NH_4Cl$ (3 mL) and stirred at 23° C. for 60 min. The layers were separated, and the aqueous layer was extracted with EtOAc (3×3 mL). The combined organic layers were washed with brine (1×5 mL), dried over silica and concentrated under reduced pressure. The crude residue was purified by flash chromatography (3:1:1 Hexanes: $CH_2Cl_2$:$Et_2O$) to yield brominated product 15 (272.0 mg, 78% yield) as an off-white solid. $R_f$ 0.17 (3:1:1 Hexanes: $CH_2Cl_2$:$Et_2O$); $^1$H NMR (500 MHz, $CDCl_3$): δ 7.54 (t, J=1.5, 1H), 7.26 (d, J=1.5, 2H), 3.50 (q, J=7.0, 2H), 3.40 (q, J=7.0, 2H), 2.99 (s, 6H), 1.31 (t, J=7.0, 3H), 1.23 (t, J=7.0, 3H); $^{D}$C NMR (125 MHz, $CDCl_3$): δ 152.9, 147.6, 147.3, 126.5, 124.8, 121.7, 116.9, 42.6, 42.3, 38.9, 14.4, 13.4; IR (film): 2977, 1724, 1592, 1472, 1372, 1148 $cm^{-1}$; HRMS-ESI (m/z) $[M+Na]^+$ calcd for $C_{13}H_{19}BrN_2O_5SNa$, 417.0096. found 417.0107.

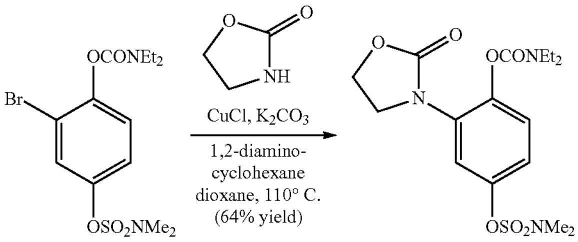

15 16

Oxazolidinone 16.

A 1 mL vial was charged with $K_2CO_3$ (55.7 mg, 0.404 mmol, 2 equiv) and a magnetic stir bar. The vial and contents were flame-dried under reduced pressure, then allowed to cool under $N_2$. Bromide 15 (80.0 mg, 0.202 mmol, 1 equiv) and 2-oxazolidinone (17.6 mg, 0.202 mmol, 1 equiv) were added. The vial was then evacuated and backfilled with $N_2$ three times and brought into a glove box. CuCl (2.0 mg, 0.020 mmol, 10 mol %) was added and the reaction vessel was removed from the glove box and placed under an atmosphere of $N_2$. (±)-trans-1,2-diaminocyclohexane (4.8 μL, 0.040 mmol, 20 mol %) was then added, followed by anhydrous dioxane (110 μL). The reaction vessel was shielded from light, sealed with a Teflon-coated cap, and heated to 110° C. After 13 h, the reaction was allowed to cool to 23° C. The residue was diluted in EtOAc (1 mL) and filtered over a pad of celite (EtOAc eluent, 7 mL). Concentrated under reduced pressure afforded the crude product, which was further purified by flash chromatography (1:1 Benzene:EtOAc) to yield oxazolidinone 16 as a yellow oil (51.9 mg, 64% yield). $R_f$ 0.28 (1:1 Benzene:EtOAc); $^1H$ NMR (500 MHz, $CDCl_3$): δ 7.32 (dd, J=2.0, 1.0, 1H), 7.23 (d, J=2.0, 2H), 4.44 (t, J=8.0, 2H), 3.98 (t, J=7.8, 2H), 3.44 (q, J=7.2, 2H), 3.36 (q, J=7.0, 2H), 2.96 (s, 6H), 1.23 (t, J=7.0, 3H), 1.19 (t, J=7.3, 3H); $^{13}C$ NMR (125 MHz, $CDCl_3$): δ 156.1, 153.2, 147.2, 145.4, 131.1, 124.9, 121.9, 120.7, 62.8, 47.2, 42.5, 42.2, 38.9, 14.2, 13.4; IR (film): 2977, 1753, 1717, 1611, 1504, 1367, 1146 $cm^{-1}$; HRMS-ESI (m/z) $[M+Na]^+$ calcd for $C_{16}H_{23}N_3O_7SNa$, 424.1154. found 424.1150.

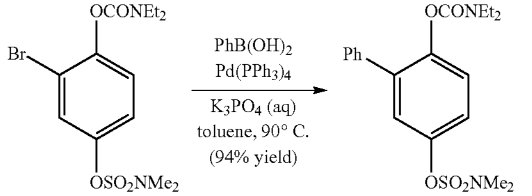

15 17

Biphenyl 17.

A 20 mL scintillation vial was charged with magnetic stir bar, $K_3PO_4$ (1 mL, 2 M aqueous) and toluene (1.7 mL) and the biphasic solution sparged with $N_2$ for 1 h. To the solution were added bromide 15 (150 mg, 0.379 mmol, 1 equiv), phenylboronic acid (56 mg, 0.455 mmol, 1.2 equiv) and $Pd(PPh_3)_4$ (66 mg, 0.057 mmol, 15 mol %) and the resulting mixture sparged with $N_2$ for 10 min. The vial was sealed with a Teflon-coated screw-cap and heated at 90° C. for 14 h. After cooling to 23° C., dichloromethane (10 mL) and $Na_2SO_4$ were added and the mixture allowed to stand for 30 min. The crude mixture was then filtered over silica and concentrated under reduced pressure. The crude residue was purified by flash chromatography (3:1:1 Hexanes:$CH_2Cl_2$:$Et_2O$) to yield biphenyl 17 as a yellow oil (140 mg, 94% yield). $R_f$ 0.22 3:1:1 Hexanes:$CH_2Cl_2$:$Et_2O$); $^1H$ NMR (500 MHz, $CDCl_3$): δ 7.40-7.22 (m, 8H), 3.23 (m, 4H), 2.99 (s, 6H), 1.04 (t, J=6.8, 3H), 0.99 (t, J=6.8, 3H); $^{13}C$ NMR (125 MHz, $CDCl_3$): δ 153.8, 147.2, 146.9, 137.0, 136.7, 129.1, 128.3, 127.8, 124.6, 123.8, 121.5, 42.2, 41.8, 38.9, 14.0, 13.2; IR (film): 2976, 1714, 1471, 1367, 1141 $cm^{-1}$; HRMS-ESI (m/z) $[M+Na]^+$ calcd for $C_{19}H_{24}N_2O_5SNa$, 415.1304. found 415.1297.

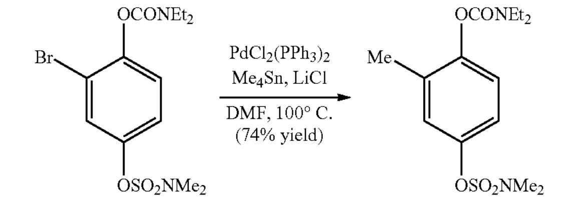

15 18

Sulfamate 18.

To a 4 mL vial charged with anhydrous lithium chloride (53.6 mg, 1.265 mmol, 5 equiv) was added a solution of bromide 15 (100.0 mg, 0.253 mmol, 1 equiv) in N,N-dimethylformamide (2.5 mL) that had been rigorously sparged with $N_2$, all in a glove box. Next, $PdCl_2(PPh_3)_2$ (4.2 mg, 0.006 mmol, 2.5 mol %) was added and the mixture stirred until a yellow solution resulted. To this solution was added neat tetramethyltin (87.7 μL, 0.633 mmol, 2.5 equiv) dropwise, still in a glove box. The reaction vial was sealed under an atmosphere of argon, removed from the glove box and heated to 100° C. for 16 h. The reaction was allowed to cool to 23° C. and then quenched by the addition of $H_2O$ (2.5 mL). The aqueous layer was extracted with EtOAc (5×6 mL). The combined organic layers were washed with brine (2×15 mL), dried over $MgSO_4$, and concentrated under reduced pressure. The crude oil was redissolved in EtOAc (5 mL) and then washed sequentially with aqueous 1 M KF (3×5 mL), saturated aqueous $NH_4Cl$ (1×5 mL), and $H_2O$ (1×5 mL). The organic layer was dried over $MgSO_4$ and concentrated under reduced pressure to yield sulfamate 18 as a white solid (62.1 mg, 74% yield). $R_f$ 0.39 (5:1 Benzene: $Et_2O$); $^1H$ NMR (500 MHz, $CDCl_3$): δ 7.14 (bs, 1H), 7.10-7.05 (m, 2H), 3.45 (q, J=7.0, 2H), 3.37 (q, J=6.5, 2H), 2.94 (s, 6H), 2.21 (s, 3H), 1.26 (t, J=6.5, 3H), 1.19 (t, J=6.8, 3H); $^{13}C$ NMR (125 MHz, $CDCl_3$): δ 153.7, 148.4, 147.0, 132.4, 124.0, 123.3, 119.9, 42.4, 42.0, 38.8, 16.5, 14.3, 13.4; IR (film): 2976, 1714, 1416, 1367, 1273, 1134 $cm^{-1}$; HRMS-ESI (m/z) $[M+Na]^+$ calcd for $C_{14}H_{22}N_2O_5SNa$, 353.1147. found 353.1142.

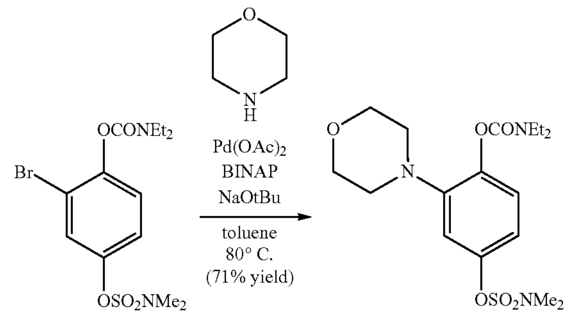

15 19

Amine 19.

A 4 mL reaction vial was charged with $Pd(OAc)_2$ (5.7 mg, 0.025 mmol, 10 mol %), BINAP (17.4 mg, 0.028 mmol, 11 mol %), anhydrous powdered NaOtBu (34.0 mg, 0.354 mmol, 1.4 equiv), bromide 15 (100.0 mg, 0.253 mmol, 1 equiv), morpholine (26.6 μL, 0.304 mmol, 1.2 equiv) and a magnetic stir bar, all in a glove box. Subsequently, toluene (1.0 mL) that had been rigorously sparged with $N_2$ was added. The vessel was sealed under an atmosphere of argon, and then heated to 80° C. for 16 h. After cooling the reaction vessel to 23° C., the crude mixture was diluted with $Et_2O$, filtered over a plug of celite with additional $Et_2O$ (10 mL) and concentrated under reduced pressure. The crude residue was purified by flash chromatography (1:1 Benzene:$Et_2O$) to yield aminated product 19 (72.1 mg, 71% yield) as a yellow oil. $R_f$ 0.33 (1:1 Benzene:$Et_2O$); $^1$H NMR (500 MHz, $CDCl_3$): δ 7.06 (d, J=8.0, 1H), 6.96-6.92 (m, 2H), 3.79 (t, J=4.8, 4H), 3.45 (q, J=7.0, 2H), 3.38 (q, J=7.0, 2H), 3.00 (t, J=4.5, 4H), 2.95 (s, 6H), 1.25 (t, J=7.0, 3H), 1.21 (t, J=7.0, 3H); $^{13}$C NMR (125 MHz, $CDCl_3$): δ 153.6, 147.8, 145.9, 143.5, 124.5, 116.2, 113.7, 67.2, 51.6, 42.3, 41.8, 38.9, 14.4, 13.5; IR (film): 2972, 1716, 1608, 1584, 1498, 1413, 1367, 1139 $cm^{-1}$; HRMS-ESI (m/z) $[M+Na]^+$ calcd for $C_{17}H_{27}N_3O_6SNa$, 424.1518. found 424.1508.

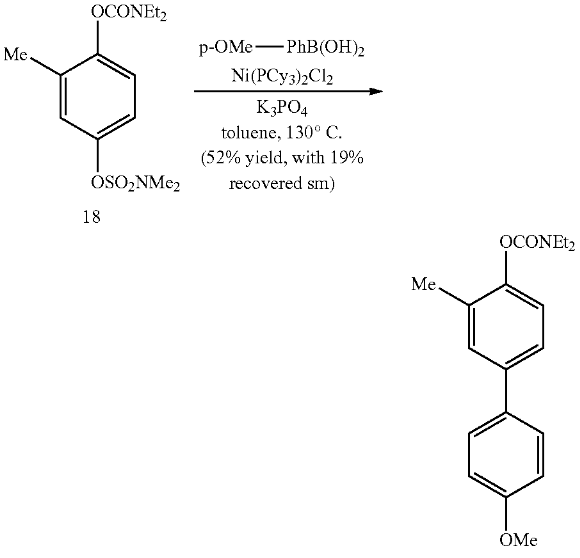

18

20

Carbamate 20.

A 4 mL vial containing potassium phosphate (0.324 g, 1.53 mmol, 7.2 equiv) was flame dried and cooled to 23° C. The $Ni(PCy_3)_2Cl_2$ (25.3 mg, 0.042 mmol, 20 mol %), boronic acid (0.161 g, 1.06 mmol, 5 equiv) and sulfamate 18 (70 mg, 0.212 mmol, 1 equiv) were added to the vial. Toluene (0.7 mL) was added to the solids and the resulting mixture was stirred at 23° C. for 1 h. The reaction was then stirred at 130° C. for 8 h. The reaction was then cooled to 23° C. and purified by flash chromatography (9:1 Benzene: $CH_2Cl_2$→8:1:1 Hexanes:EtOAc:$CH_2Cl_2$) to produce sulfamate 18 (13.3 mg, 19% yield) and carbamate 20 (34.7 mg, 52% yield) as a white solid. $R_f$ 0.24 (8:1:1 Hexanes:EtOAc: $CH_2Cl_2$); $^1$HNMR (600 MHz, $CDCl_3$): δ 7.48 (d, J=9, 2H), 7.37 (s, 1H), 7.35 (d, J=9.6, 1H), 7.10 (d, J=8.4, 1H) 6.95 (d, J=8.4, 2H), 3.85 (s, 3H), 3.49 (m, 2H), 3.41 (m, 2H), 2.27 (s, 3H), 1.25 (m, 6H); $^{13}$C NMR (125 MHz, $CDCl_3$): δ 159.1, 154.1, 149.2, 138.2, 133.5, 130.7, 129.4, 128.2, 125.2, 122.5, 114.2, 55.4, 42.4, 42.0, 16.6, 14.4, 13.5; IR (film): 2973, 2931, 1711, 1608, 1416, 1213, 1153 $cm^{-1}$; HRMS-ESI (m/z) $[M+Na]^+$ calcd for $C_{19}H_{23}NO_3Na$, 336.1576. found 336.1567.

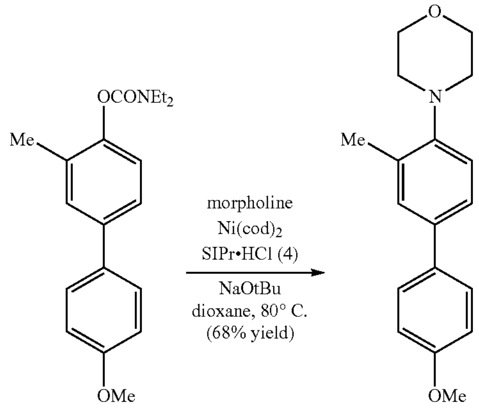

20

21

Amine 21.

A 4 mL vial was charged with carbamate 20 (45.5 mg, 0.145 mmol, 1 equiv), $Ni(cod)_2$ (4.1 mg, 0.015 mmol, 10 mol %), SIPr.HCl (12.8 mg, 0.03 mmol, 20 mol %), anhydrous powdered NaOtBu (30.6 mg, 0.319 mmol, 2.2 equiv), and a magnetic stir bar, all in a glove box. Subsequently, morpholine (30.5 μL, 0.348 mmol, 2.4 equiv) and dioxane (0.73 mL) were added. The vessel was sealed and removed from the glove box, and then heated to 80° C. for 3 h. After cooling the reaction vessel to 23° C., the reaction mixture was filtered over a pad of silica, washed with EtOAc (10 mL) and evaporated to dryness. To the crude residue was added $CH_2Cl_2$ (0.5 mL), benzene (0.1 mL) and hexanes (1.5 mL) the solvents were layered. The hexane and benzene layers were mixed and then placed in the refrigerator overnight. The crystals were washed with dry ice cold hexanes (4 mL) to yield amine 21 (27.8 mg, 68% yield) as a yellow solid. $R_f$ 0.39 (8:1:1 Hexanes:EtOAc:$CH_2Cl_2$); $^1$H NMR (600 MHz, $CDCl_3$): δ 7.49 (d, J=7.8, 2H), 7.39 (s, 1H), 7.36 (d, J=7.8, 1H), 7.07 (d, J=7.8, 1H) 6.96 (d, J=7.8, 2H), 3.87 (bs, 4H), 3.85 (bs, 3H), 2.95 (bs, 4H), 2.37 (bs, 3H); $^{13}$C NMR (125 MHz, $CDCl_3$): δ 158.9, 150.3, 136.0, 133.7, 133.0, 130.0, 128.0, 125.0, 119.3, 114.3, 67.6, 55.5, 52.4, 18.2; IR (film): 2990, 2963, 2854, 2836, 1718, 1605, 1581, 1496, 1224, 1116, 1023 $cm^{-1}$; HRMS-ESI (m/z) $[M+H]^+$ calcd for $C_{18}H_{21}NO_2H$, 284.1650. found 284.1648.

All patent and non-patent publications cited in this disclosure are incorporated herein in to the extent as if each of those patent and non-patent publications was incorporated herein by reference in its entirety. Further, even though the invention herein has been described with reference to particular examples and embodiments, it is to be understood that these examples and embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A method for making a cross-coupled compound comprising: combining together:

an aryl alcohol compound, wherein the aryl alcohol compound comprises an aryl sulfamate compound;

an amine; and a transition metal catalyst, wherein the transition metal catalyst comprises nickel or palladium;

wherein the aryl alcohol compound, the amine and the transition metal catalyst are combined so as to allow a cross-coupling reaction between the amine, the aryl alcohol compound and the transition metal catalyst that results in the formation of a cross-coupled compound that comprises a C—N bond between a carbon atom present in the aryl alcohol compound and a nitrogen atom present in the amine, in a yield of at least 25% and wherein the transition metal catalyst is regenerated simultaneously with formation of the cross-coupled compound;

so that the cross-coupled compound is made.

2. The method of claim 1, wherein the cross-coupling reaction results in the formation of the cross-coupled compound in a yield of at least 50%.

3. The method of claim 1, wherein the aryl alcohol compound comprises an aryl sulfamate compound.

4. The method of claim 1, wherein the amine comprises a secondary amine.

5. The method of claim 1, wherein the aryl alcohol compound comprises a heteroatom.

6. The method of claim 1, wherein the transition metal catalyst comprises nickel.

7. The method of claim 1, wherein the transition metal catalyst comprises an air stable Ni(II) precatalyst complex prior to its combination with the amine and the aryl alcohol derivative.

8. The method of claim 1, wherein the method is used in the synthesis of linezolid.

9. A method for performing a cross-coupling reaction comprising: combining together:

an amine;

an aryl alcohol compound, wherein the aryl alcohol compound comprises an aryl sulfamate compound; and a transition metal catalyst, wherein the transition metal catalyst comprises nickel or palladium;

wherein the amine, the aryl alcohol compound and the transition metal catalyst are combined so as to allow:

oxidative addition of the transition metal catalyst and generation of a first organo-transition metal species;

reaction between the first organo-transition metal species and the amine and generation of a second organo-transition metal species; and reductive elimination of the second organo-transition metal species, regeneration of the transition metal catalyst and generation of a cross-coupled compound in a yield of at least 25%;

so that a cross-coupling reaction is performed.

10. The method of claim 9, wherein the reaction produces the cross-coupled compound in a yield of at least 50%.

11. The method of claim 9, wherein the amine comprises a secondary amine.

12. The method of claim 9, wherein the cross coupled compound is an intermediate in a process for the synthesis of linezolid.

13. The method of claim 9, wherein the transition metal catalyst comprises nickel and the organo-transition metal species comprises an organo-nickel species.

14. The method of claim 9, wherein the aryl alcohol compound comprises a heteroatom.

15. The method of claim 9, wherein the reaction is performed as a one-pot synthesis.

16. The method of claim 9, wherein the coupling reaction is not performed in a glovebox.

17. The method of claim 9, wherein the transition metal catalyst comprises an air stable Ni(II) precatalyst complex immediately prior to its combination with the amine and the aryl alcohol compound.

18. The method of claim 9, wherein the method results in the formation of linezolid.

19. A cross-coupled compound made by a process comprising combining together:

an amine;

an aryl alcohol compound, wherein the aryl alcohol compound comprises an aryl sulfamate compound; and a transition metal catalyst, wherein the transition metal catalyst comprises nickel or palladium;

wherein the amine the aryl alcohol compound and the transition metal catalyst are combined so as to allow chemical reaction between the amine, the aryl alcohol compound and the transition metal catalyst, wherein the reaction results in the formation of a cross-coupled compound in a yield of at least 25% and wherein the transition metal catalyst is regenerated simultaneously with formation of the cross-coupled compound;

so that the cross-coupled compound is made.

20. A method for making a cross-coupled compound comprising: combining together:

an aryl alcohol compound with a chemical structure:

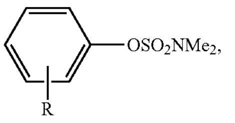

wherein R is a functional group;

an amine with a structure:

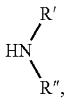

wherein R' and R" are functional groups; and a transition metal catalyst, wherein the transition metal catalyst comprises nickel or palladium;

wherein the aryl alcohol compound, the amine and the transition metal catalyst are combined so as to allow a cross-coupling reaction between the amine, the aryl alcohol compound and the transition metal catalyst that results in the formation of a cross-coupled compound with a structure:

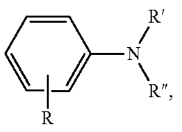

in a yield of at least 25% and wherein the transition metal catalyst is regenerated simultaneously with formation of the cross-coupled compound;

so that the cross-coupled compound is made.

* * * * *